US011603411B2

(12) United States Patent
Duerr et al.

(10) Patent No.: US 11,603,411 B2
(45) Date of Patent: Mar. 14, 2023

(54) BISPECIFIC ANTI-HUMAN CD20/HUMAN TRANSFERRIN RECEPTOR ANTIBODIES AND METHODS OF USE

(71) Applicant: Hoffmann-La Roche Inc., Little Falls, NJ (US)

(72) Inventors: Harald Duerr, Starnberg (DE); Sebastian Fenn, Achmuehle/Eurasburg (DE); Ulrich Goepfert, Penzberg (DE); Sabine Imhof-Jung, Planegg (DE); Christian Klein, Bonstetten (CH); Laurent Lariviere, Munich (DE); Michael Molhoj, Munich (DE); Joerg Thomas Regula, Munich (DE); Petra Rueger, Penzberg (DE); Wolfgang Schaefer, Mannheim (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/941,524

(22) Filed: Mar. 30, 2018

(65) Prior Publication Data
US 2018/0222993 A1  Aug. 9, 2018

Related U.S. Application Data

(63) Continuation of application No. PCT/EP2016/073413, filed on Sep. 30, 2016.

(30) Foreign Application Priority Data

Oct. 2, 2015  (EP) .................... 15188067

(51) Int. Cl.
*C07K 16/28* (2006.01)
*A61P 25/00* (2006.01)

(52) U.S. Cl.
CPC .......... *C07K 16/2887* (2013.01); *A61P 25/00* (2018.01); *C07K 16/2881* (2013.01); *C07K 2317/31* (2013.01); *C07K 2317/515* (2013.01); *C07K 2317/522* (2013.01); *C07K 2317/55* (2013.01); *C07K 2317/66* (2013.01); *C07K 2317/92* (2013.01); *C07K 2317/94* (2013.01)

(58) Field of Classification Search
CPC ............ C07K 16/2887; C07K 16/2881; C07K 2317/94; C07K 2317/92; C07K 2317/66; C07K 2317/55; C07K 2317/522; C07K 2317/515; C07K 2317/31; C07K 16/18; C07K 16/468; A61P 25/00; A61P 35/00; A61P 37/02; A61K 2039/505; A61K 39/695

See application file for complete search history.

(56) References Cited

U.S. PATENT DOCUMENTS

| | | |
|---|---|---|
| 3,773,919 A | 11/1973 | Boswell et al. |
| 4,120,649 A | 10/1978 | Schechter |
| 4,665,077 A | 5/1987 | Stringfellow et al. |
| 4,737,456 A | 4/1988 | Weng et al. |
| 4,816,567 A | 3/1989 | Cabilly et al. |
| 4,861,579 A | 8/1989 | Meyer, Jr. et al. |
| 4,892,538 A | 1/1990 | Aebischer et al. |
| 5,114,721 A | 5/1992 | Cohen et al. |
| 5,154,924 A | 10/1992 | Friden |
| 5,195,317 A | 3/1993 | Nobue et al. |
| 5,208,020 A | 5/1993 | Chari et al. |
| 5,231,000 A | 7/1993 | Majocha et al. |
| 5,283,187 A | 2/1994 | Aebischer et al. |
| 5,416,064 A | 5/1995 | Chari et al. |
| 5,427,927 A | 6/1995 | Meyer et al. |
| 5,500,362 A | 3/1996 | Robinson et al. |
| 5,595,721 A | 1/1997 | Kaminski et al. |
| 5,624,821 A | 4/1997 | Winter et al. |
| 5,635,483 A | 6/1997 | Pettit et al. |
| 5,648,237 A | 7/1997 | Carter |
| 5,648,260 A | 7/1997 | Winter et al. |
| 5,677,180 A | 10/1997 | Robinson et al. |
| 5,688,651 A | 11/1997 | Solomon et al. |
| 5,712,374 A | 1/1998 | Kuntsmann et al. |
| 5,714,586 A | 2/1998 | Kunstmann et al. |
| 5,721,108 A | 2/1998 | Robinson et al. |
| 5,736,137 A | 4/1998 | Anderson et al. |
| 5,739,116 A | 4/1998 | Hamann et al. |
| 5,767,285 A | 6/1998 | Hamann et al. |
| 5,770,429 A | 6/1998 | Lonberg et al. |
| 5,770,701 A | 6/1998 | McGahren et al. |
| 5,770,710 A | 6/1998 | McGahren et al. |
| 5,773,001 A | 6/1998 | Hamann et al. |
| 5,776,456 A | 7/1998 | Anderson et al. |
| 5,780,588 A | 7/1998 | Pettit et al. |
| 5,789,199 A | 8/1998 | Joly et al. |

(Continued)

FOREIGN PATENT DOCUMENTS

| | | |
|---|---|---|
| CL | 2014-03161 | 11/2014 |
| CL | 201503406 | 11/2015 |

(Continued)

OTHER PUBLICATIONS

Lloyd et al. Protein Engineering, Design & Selection 22:159-168 (Year: 2009).*
Edwards et al.,J Mol Biol. 334(1): 103-118 (Year: 2003).*
Rudikoff et al., Proc. Natl. Acad. Sci. USA 79:1979-1983 (Year: 1982).*
Hawker et al., "Rituximab in patients with primary progressive multiple sclerosis: results of a randomized double-blind placebo-controlled multicenter trial" American Neurological Association 66:460-471 (2009).

(Continued)

*Primary Examiner* — Phuong Huynh
(74) *Attorney, Agent, or Firm* — Yan Qi

(57) ABSTRACT

Herein are provided bispecific anti-human CD20/human transferrin receptor antibodies and methods of using the same.

5 Claims, No Drawings
Specification includes a Sequence Listing.

(56) References Cited

U.S. PATENT DOCUMENTS

| | | | |
|---|---|---|---|
| 5,821,337 | A | 10/1998 | Carter et al. |
| 5,840,523 | A | 11/1998 | Simmons et al. |
| 5,843,398 | A | 12/1998 | Kaminski et al. |
| 5,843,439 | A | 12/1998 | Anderson et al. |
| 5,849,898 | A | 12/1998 | Seed et al. |
| 5,877,296 | A | 3/1999 | Hamann et al. |
| 5,955,317 | A | 9/1999 | Suzuki et al. |
| 5,959,177 | A | 9/1999 | Hein et al. |
| 6,015,542 | A | 1/2000 | Kaminski et al. |
| 6,015,555 | A | 1/2000 | Friden |
| 6,040,498 | A | 3/2000 | Stomp et al. |
| 6,066,652 | A | 5/2000 | Zenner et al. |
| 6,075,181 | A | 6/2000 | Kucherlapati et al. |
| 6,083,747 | A | 7/2000 | Wong et al. |
| 6,090,365 | A | 7/2000 | Kaminski et al. |
| 6,120,767 | A | 9/2000 | Robinson et al. |
| 6,150,584 | A | 11/2000 | Kucherlapati et al. |
| 6,171,586 | B1 | 1/2001 | Lam et al. |
| 6,194,551 | B1 | 2/2001 | Idusogie et al. |
| 6,224,866 | B1 | 5/2001 | Barbera-Guillem |
| 6,242,195 | B1 | 6/2001 | Idusogie et al. |
| 6,267,958 | B1 | 7/2001 | Andya et al. |
| 6,287,537 | B1 | 9/2001 | Kaminski et al. |
| 6,306,393 | B1 | 10/2001 | Goldenberg |
| 6,368,596 | B1 | 4/2002 | Ghetie et al. |
| 6,399,061 | B1 | 6/2002 | Anderson et al. |
| 6,410,391 | B1 | 6/2002 | Zelsacher |
| 6,417,429 | B1 | 7/2002 | Hein et al. |
| 6,420,548 | B1 | 7/2002 | Vezina et al. |
| 6,455,043 | B1 | 9/2002 | Grillo-Lopez |
| 6,528,624 | B1 | 3/2003 | Idusogie et al. |
| 6,538,124 | B1 | 3/2003 | Idusogie et al. |
| 6,565,827 | B1 | 5/2003 | Kaminski et al. |
| 6,602,684 | B1 | 8/2003 | Umana et al. |
| 6,630,579 | B2 | 10/2003 | Chari et al. |
| 6,652,852 | B1 | 11/2003 | Robinson et al. |
| 6,682,734 | B1 | 1/2004 | Anderson et al. |
| 6,737,056 | B1 | 5/2004 | Presta |
| 6,982,321 | B2 | 1/2006 | Winter |
| 7,041,870 | B2 | 5/2006 | Tomizuka et al. |
| 7,087,409 | B2 | 8/2006 | Barbas et al. |
| 7,125,978 | B1 | 10/2006 | Vezina et al. |
| 7,189,826 | B2 | 3/2007 | Rodman |
| 7,332,581 | B2 | 2/2008 | Presta |
| 7,371,826 | B2 | 5/2008 | Presta |
| 7,498,298 | B2 | 3/2009 | Doronina et al. |
| 7,521,541 | B2 | 4/2009 | Eigenbrot et al. |
| 7,527,791 | B2 | 5/2009 | Adams et al. |
| 7,794,719 | B2 | 9/2010 | Bardroff |
| 8,883,980 | B2 | 11/2014 | Umana et al. |
| 8,945,867 | B2 | 2/2015 | Ogawa et al. |
| 9,598,496 | B2 | 3/2017 | Kurosawa et al. |
| 9,714,292 | B2 | 7/2017 | Auer et al. |
| 10,323,089 | B2 | 6/2019 | Dengl et al. |
| 10,323,099 | B2 | 6/2019 | Bruenker et al. |
| 10,364,292 | B2 | 7/2019 | Rueger et al. |
| 10,370,692 | B2 | 8/2019 | Kopetzki |
| 10,941,205 | B2 * | 3/2021 | Duerr ............... C07K 16/18 |
| 11,098,338 | B2 | 8/2021 | Kopetzki et al. |
| 2001/0018041 | A1 | 8/2001 | Hanna et al. |
| 2001/0056066 | A1 | 12/2001 | Bugelski et al. |
| 2002/0004587 | A1 | 1/2002 | Miller et al. |
| 2002/0006404 | A1 | 1/2002 | Hanna et al. |
| 2002/0009427 | A1 | 1/2002 | Wolin et al. |
| 2002/0009444 | A1 | 1/2002 | Grillo-Lopez |
| 2002/0012665 | A1 | 1/2002 | Hanna |
| 2002/0025313 | A1 | 2/2002 | Micklus et al. |
| 2002/0041847 | A1 | 4/2002 | Goldenberg |
| 2002/0058029 | A1 | 5/2002 | Hanna |
| 2002/0127652 | A1 | 9/2002 | Schambye et al. |
| 2002/0128488 | A1 | 9/2002 | Yamakawa et al. |
| 2002/0136719 | A1 | 9/2002 | Shenoy et al. |
| 2002/0164328 | A1 | 11/2002 | Shinkawa et al. |
| 2002/0197255 | A1 | 12/2002 | Anderson et al. |
| 2002/0197256 | A1 | 12/2002 | Grewal |
| 2003/0003097 | A1 | 1/2003 | Reff et al. |
| 2003/0021781 | A1 | 1/2003 | Anderson et al. |
| 2003/0026801 | A1 | 2/2003 | Weiner et al. |
| 2003/0068664 | A1 | 4/2003 | Albitar et al. |
| 2003/0082172 | A1 | 5/2003 | Anderson et al. |
| 2003/0095963 | A1 | 5/2003 | Anderson et al. |
| 2003/0103971 | A1 | 6/2003 | Hariharan et al. |
| 2003/0115614 | A1 | 6/2003 | Kanda et al. |
| 2003/0133930 | A1 | 7/2003 | Goldenberg et al. |
| 2003/0147885 | A1 | 8/2003 | Anderson et al. |
| 2003/0148404 | A1 | 8/2003 | Michaelson |
| 2003/0157108 | A1 | 8/2003 | Presta |
| 2003/0180292 | A1 | 9/2003 | Hanna et al. |
| 2003/0185796 | A1 | 10/2003 | Wolin et al. |
| 2003/0202972 | A1 | 10/2003 | Andya et al. |
| 2003/0219433 | A1 | 11/2003 | Hansen et al. |
| 2003/0219818 | A1 | 11/2003 | Bohen et al. |
| 2004/0082762 | A1 | 4/2004 | Basi et al. |
| 2004/0093621 | A1 | 5/2004 | Shitara et al. |
| 2004/0109865 | A1 | 6/2004 | Niwa et al. |
| 2004/0110282 | A1 | 6/2004 | Kanda et al. |
| 2004/0110704 | A1 | 6/2004 | Yamane et al. |
| 2004/0131692 | A1 | 7/2004 | Kreuter et al. |
| 2004/0132140 | A1 | 7/2004 | Satoh et al. |
| 2004/0180417 | A1 | 9/2004 | Seidah |
| 2004/0192898 | A1 | 9/2004 | Jia et al. |
| 2004/0197324 | A1 | 10/2004 | Liu et al. |
| 2004/0204354 | A1 | 10/2004 | Nelson et al. |
| 2004/0248197 | A1 | 12/2004 | Holtzman et al. |
| 2005/0014934 | A1 | 1/2005 | Hinton et al. |
| 2005/0058644 | A1 | 3/2005 | Engleman |
| 2005/0123546 | A1 | 6/2005 | Umana et al. |
| 2005/0142133 | A1 | 6/2005 | Lazar et al. |
| 2005/0147613 | A1 | 7/2005 | Raso |
| 2005/0169925 | A1 | 8/2005 | Bardroff et al. |
| 2005/0180972 | A1 | 8/2005 | Wahl et al. |
| 2005/0260186 | A1 | 11/2005 | Bookbinder et al. |
| 2006/0008883 | A1 | 1/2006 | Lazar et al. |
| 2006/0104968 | A1 | 5/2006 | Bookbinder et al. |
| 2006/0210557 | A1 | 9/2006 | Luisi et al. |
| 2006/0251652 | A1 | 11/2006 | Watkins et al. |
| 2007/0061900 | A1 | 3/2007 | Murphy et al. |
| 2007/0098721 | A1 | 5/2007 | Heinz et al. |
| 2008/0167449 | A1 | 7/2008 | Lazar et al. |
| 2008/0275220 | A1 | 11/2008 | Friess et al. |
| 2009/0162359 | A1 | 6/2009 | Klein et al. |
| 2009/0252724 | A1 | 10/2009 | Loetscher et al. |
| 2009/0263491 | A1 | 10/2009 | Kreuter et al. |
| 2009/0297436 | A1 | 12/2009 | Garcia-Martinez et al. |
| 2010/0016786 | A1 | 1/2010 | Drews et al. |
| 2010/0077498 | A1 | 3/2010 | Pardridge et al. |
| 2010/0081796 | A1 | 4/2010 | Brinkmann et al. |
| 2010/0121036 | A1 | 5/2010 | Fischer et al. |
| 2010/0129357 | A1 | 5/2010 | Garcia-Martinez et al. |
| 2010/0172907 | A1 | 7/2010 | Bardroff et al. |
| 2010/0190247 | A1 | 7/2010 | Lazar et al. |
| 2010/0256338 | A1 | 10/2010 | Brinkmann et al. |
| 2011/0070225 | A1 | 3/2011 | Goldbach et al. |
| 2012/0034160 | A1 * | 2/2012 | Ghayur ............... C07K 16/244 424/1.49 |
| 2012/0141484 | A1 | 7/2012 | Garcia-Martinez et al. |
| 2012/0171120 | A1 | 7/2012 | Dennis et al. |
| 2012/0244577 | A1 | 9/2012 | Dixit et al. |
| 2013/0034554 | A1 | 2/2013 | Garcia-Martinez et al. |
| 2013/0039925 | A1 | 2/2013 | Bansal |
| 2013/0045206 | A1 | 2/2013 | Poul et al. |
| 2013/0078249 | A1 * | 3/2013 | Ast ............... C07K 16/468 424/136.1 |
| 2013/0090457 | A1 | 4/2013 | Cunningham et al. |
| 2013/0136747 | A1 | 5/2013 | Bardroff et al. |
| 2013/0315901 | A1 | 11/2013 | Derosier et al. |
| 2014/0154254 | A1 * | 6/2014 | Kannan ............... C07K 16/18 424/136.1 |
| 2014/0212423 | A1 | 7/2014 | Karaoglu-Hanzatian et al. |
| 2014/0271459 | A1 | 9/2014 | Dutzar |
| 2014/0271464 | A1 | 9/2014 | Garcia-Martinez et al. |
| 2014/0271661 | A1 | 9/2014 | Ye et al. |
| 2015/0030589 | A1 | 1/2015 | Goldbach et al. |
| 2015/0125446 | A1 | 5/2015 | Klein et al. |

(56) References Cited

U.S. PATENT DOCUMENTS

| | | | |
|---|---|---|---|
| 2015/0132217 A1 | 5/2015 | Chang et al. | |
| 2015/0140003 A1 | 5/2015 | Kaluza et al. | |
| 2015/0196663 A1 | 7/2015 | Shusta et al. | |
| 2015/0266947 A1 | 9/2015 | Sierks | |
| 2015/0315296 A1 | 11/2015 | Schaefer et al. | |
| 2015/0322149 A1 | 11/2015 | Bohrmann et al. | |
| 2015/0353639 A1 | 12/2015 | Watts et al. | |
| 2016/0145348 A1 | 5/2016 | Stephan | |
| 2018/0171012 A1 | 6/2018 | Sonoda et al. | |
| 2018/0222992 A1 | 8/2018 | Duerr et al. | |
| 2018/0222993 A1 | 8/2018 | Duerr et al. | |
| 2018/0282408 A1 | 10/2018 | Dengl et al. | |
| 2018/0291110 A1 | 10/2018 | Klein et al. | |
| 2019/0276530 A1 | 9/2019 | Bohrmann et al. | |
| 2020/0055931 A1 | 2/2020 | Dengl et al. | |
| 2020/0216553 A1* | 7/2020 | Seeber | C07K 16/2878 |
| 2020/0216554 A1* | 7/2020 | Duerr | C07K 16/2881 |
| 2022/0144963 A9 | 5/2022 | Duerr et al. | |

FOREIGN PATENT DOCUMENTS

| | | |
|---|---|---|
| CL | 201703207 | 12/2017 |
| CL | 201703351 | 12/2017 |
| CL | 201800819 | 3/2018 |
| CN | 102740888 A | 10/2012 |
| CN | 102741282 A | 10/2012 |
| CO | 2017012416 A2 | 2/2018 |
| CO | 2018000235 A2 | 3/2018 |
| CO | 2018003452 A2 | 6/2018 |
| EP | 0332865 A2 | 9/1989 |
| EP | 0307434 B1 | 9/1993 |
| EP | 0683234 | 1/1994 |
| EP | 0425235 B1 | 9/1996 |
| EP | 0330191 B1 | 10/1996 |
| EP | 0340109 B1 | 5/1997 |
| EP | 1125905 | 8/2001 |
| EP | 2343086 A1 | 7/2011 |
| EP | 2 668 901 A1 | 12/2013 |
| EP | 2708560 A1 | 3/2014 |
| EP | 2787078 A1 | 10/2014 |
| FR | 2953841 | 12/2009 |
| FR | 2 953 841 A1 | 6/2011 |
| JP | 2014-506258 A | 3/2014 |
| JP | 2015-528452 A | 9/2015 |
| JP | 2017187722 | 12/2017 |
| JP | 2018516811 A | 6/2018 |
| RU | 2 439 160 C1 | 1/2012 |
| UA | a201002186 | 5/2010 |
| WO | 90/08187 A1 | 7/1990 |
| WO | 90/11294 A1 | 10/1990 |
| WO | 91/01133 A1 | 2/1991 |
| WO | WO91/11520 | 8/1991 |
| WO | 93/10819 A1 | 6/1993 |
| WO | 93/21232 A1 | 10/1993 |
| WO | 93/25673 A1 | 12/1993 |
| WO | 94/11026 A2 | 5/1994 |
| WO | 94/29351 A2 | 12/1994 |
| WO | 95/03770 A1 | 2/1995 |
| WO | 95/15769 | 6/1995 |
| WO | 96/07321 A1 | 3/1996 |
| WO | 96/20218 | 7/1996 |
| WO | 96/25088 | 8/1996 |
| WO | 96/39628 | 12/1996 |
| WO | 97/04801 A1 | 2/1997 |
| WO | 97/08320 | 3/1997 |
| WO | 97/30087 A1 | 8/1997 |
| WO | 98/56418 A1 | 12/1998 |
| WO | 98/58964 A1 | 12/1998 |
| WO | 99/22764 A1 | 5/1999 |
| WO | 99/27944 | 6/1999 |
| WO | 99/51642 A1 | 10/1999 |
| WO | 00/09160 A1 | 2/2000 |
| WO | 00/20864 A1 | 4/2000 |
| WO | 2000/23472 A2 | 4/2000 |
| WO | 00/27428 A1 | 5/2000 |
| WO | 00/27433 A1 | 5/2000 |
| WO | 00/42072 A2 | 7/2000 |
| WO | 00/44788 A1 | 8/2000 |
| WO | 00/61739 A1 | 10/2000 |
| WO | 00/61768 | 10/2000 |
| WO | 00/64482 A1 | 11/2000 |
| WO | 00/67795 A1 | 11/2000 |
| WO | 00/67796 A1 | 11/2000 |
| WO | 00/72880 | 12/2000 |
| WO | 00/74718 A1 | 12/2000 |
| WO | 00/76542 A1 | 12/2000 |
| WO | 00/77178 | 12/2000 |
| WO | 01/03734 A1 | 1/2001 |
| WO | 01/10460 A1 | 2/2001 |
| WO | 01/10461 A1 | 2/2001 |
| WO | 01/10462 A1 | 2/2001 |
| WO | 01/13945 A1 | 3/2001 |
| WO | 01/29246 A1 | 4/2001 |
| WO | 01/34194 A1 | 5/2001 |
| WO | 01/39796 | 6/2001 |
| WO | 01/72333 A1 | 10/2001 |
| WO | 01/74388 A1 | 10/2001 |
| WO | 01/77342 A1 | 10/2001 |
| WO | 01/80884 A1 | 11/2001 |
| WO | 01/97858 A2 | 12/2001 |
| WO | 02/02597 A2 | 1/2002 |
| WO | 02/04021 A1 | 1/2002 |
| WO | 02/031140 A1 | 4/2002 |
| WO | 02/34790 A1 | 5/2002 |
| WO | 02/46237 | 6/2002 |
| WO | 02/060955 A2 | 8/2002 |
| WO | 02/064734 | 8/2002 |
| WO | 02/079255 A1 | 10/2002 |
| WO | 02/088306 | 11/2002 |
| WO | 02/088307 | 11/2002 |
| WO | 02/096937 | 12/2002 |
| WO | 02/096948 A2 | 12/2002 |
| WO | 02/102312 A2 | 12/2002 |
| WO | 03/002607 A1 | 1/2003 |
| WO | 03/009817 A2 | 2/2003 |
| WO | 03/011878 A2 | 2/2003 |
| WO | 03/016466 A2 | 2/2003 |
| WO | 03/049694 A2 | 6/2003 |
| WO | 03/061694 A1 | 7/2003 |
| WO | 03/068821 A2 | 8/2003 |
| WO | 03/070760 A2 | 8/2003 |
| WO | 03/084570 A1 | 10/2003 |
| WO | 03/085107 A1 | 10/2003 |
| WO | 03/085119 | 10/2003 |
| WO | 2004/014953 A3 | 2/2004 |
| WO | 2004/032828 A2 | 4/2004 |
| WO | 2004/032868 | 4/2004 |
| WO | 2004/035607 A2 | 4/2004 |
| WO | 2004/056312 A2 | 7/2004 |
| WO | 2004/103404 A1 | 12/2004 |
| WO | 2005/035586 A1 | 4/2005 |
| WO | 2005/035778 A1 | 4/2005 |
| WO | 2005/053742 A1 | 6/2005 |
| WO | 2005/100402 A1 | 10/2005 |
| WO | 2005092925 A3 | 10/2005 |
| WO | 2005/116220 A1 | 12/2005 |
| WO | 2006/029879 A2 | 3/2006 |
| WO | 2006/044908 A2 | 4/2006 |
| WO | 2006/081587 A2 | 8/2006 |
| WO | 2006/083689 A2 | 8/2006 |
| WO | 2006/131013 A2 | 12/2006 |
| WO | 2007/044323 A2 | 4/2007 |
| WO | 2007/044323 A3 | 4/2007 |
| WO | 2007/068429 A1 | 6/2007 |
| WO | 07/110152 | 10/2007 |
| WO | 2007/110339 A1 | 10/2007 |
| WO | 2008/005847 A2 | 1/2008 |
| WO | 2008/022349 A2 | 2/2008 |
| WO | 2008/022349 A3 | 2/2008 |
| WO | 2008/025527 A1 | 3/2008 |
| WO | 2008/039944 A2 | 3/2008 |
| WO | 2008/063771 | 5/2008 |
| WO | 2008/071394 A1 | 6/2008 |
| WO | 2008/077546 A1 | 7/2008 |

(56) References Cited

FOREIGN PATENT DOCUMENTS

| | | |
|---|---|---|
| WO | 2009/018411 | 2/2009 |
| WO | 2010/033587 A2 | 3/2010 |
| WO | 2010/102251 A2 | 9/2010 |
| WO | 2010/115551 A1 | 10/2010 |
| WO | 2010/115553 A1 | 10/2010 |
| WO | 2011/066369 A2 | 6/2011 |
| WO | 2011/066371 A2 | 6/2011 |
| WO | 2011/073943 A1 | 6/2011 |
| WO | 2011/116387 A1 | 9/2011 |
| WO | 2015/063339 | 5/2012 |
| WO | 2012/075037 A1 | 6/2012 |
| WO | 2012/087835 A2 | 6/2012 |
| WO | 2012/075037 A1 | 7/2012 |
| WO | 2012/093125 A1 | 7/2012 |
| WO | 2012/096924 A1 | 7/2012 |
| WO | 2012/130831 A1 | 10/2012 |
| WO | 2012/143379 A1 | 10/2012 |
| WO | 2012/153707 A1 | 11/2012 |
| WO | 2013012733 A1 | 1/2013 |
| WO | 2013/025853 A1 | 2/2013 |
| WO | 2013/026831 A1 | 2/2013 |
| WO | 2013/09471 A1 | 3/2013 |
| WO | 2013/038156 1 | 3/2013 |
| WO | 2013/079174 A1 | 6/2013 |
| WO | 2013/113615 A1 | 8/2013 |
| WO | 2013/127816 | 9/2013 |
| WO | 2013/131866 A1 | 9/2013 |
| WO | 2013/177062 A2 | 11/2013 |
| WO | 2014/033074 A1 | 3/2014 |
| WO | 2014/039855 | 3/2014 |
| WO | 2014/047231 A1 | 3/2014 |
| WO | 2014/052188 A1 | 4/2014 |
| WO | 2014/081955 A1 | 5/2014 |
| WO | WO2014081955 A1 | 5/2014 |
| WO | 2014/082179 A1 | 6/2014 |
| WO | 2014/089209 A1 | 6/2014 |
| WO | 2014/089209 A3 | 6/2014 |
| WO | 2014/11694 A1 | 9/2014 |
| WO | 2014/131711 A1 | 9/2014 |
| WO | 2014/153114 A1 | 9/2014 |
| WO | 2014153114 A1 | 9/2014 |
| WO | 2014/183973 | 11/2014 |
| WO | 2014/189973 A2 | 11/2014 |
| WO | 2015/014884 A1 | 2/2015 |
| WO | 2015095392 A1 | 6/2015 |
| WO | 2015/101588 A1 | 7/2015 |
| WO | 2016/020309 A1 | 2/2016 |
| WO | 2016/086189 | 6/2016 |
| WO | 2016/160032 A1 | 10/2016 |
| WO | 2016/207091 | 12/2016 |
| WO | 2016/207091 A1 | 12/2016 |
| WO | 2016/207240 A1 | 12/2016 |
| WO | 2016/208695 A1 | 12/2016 |
| WO | 2017/055540 A1 | 4/2017 |
| WO | 2017/055542 A1 | 4/2017 |
| WO | 2009/126616 A2 | 10/2019 |

OTHER PUBLICATIONS

International Preliminary Report on Patentability (IPRP) for PCT/EP2016/073413 dated Apr. 3, 2018.
International Search Report for PCT/EP 2016/073413 dated 9 Jan. 9, 2017.
Pardridge et al., "Blood—brain barrier drug delivery of IgG fusion proteins with a transferrin receptor monoclonal antibody" Expert Opin. Drug Deliv. 12(2):207-222 ( 2015).
Schaefer et al., "Immunoglobulin domain crossover as a generic approach for the production of bispecific IgG antibodies" Proceedings of the National Academy of Sciences 108(27):11187-11192 (2011).
Sumbria et al., "Disaggregation of Amyloid Plaque in Brain of Alzheimer's Disease Transgenic Mice with Daily Subcutaneous Administration of a Tetravalent Bispecific Antibody That Targets the Transferrin Receptor and the Abeta Amyloid Peptide" Mole Pharm 10(9):3507-3513 ( 2013).
Von Budingen et al., "B cells in multiple sclerosis: connecting the dots" Current Opinion in Immunology 23:713-720 ( 2011).
Yu et al., "Therapeutic bispecific antibodies cross the blood-brain barrier in nonhuman primates" Science Translational Medicine 6(261):1-11 (2014).
"ACTI™ Non-radioactive cytotoxicity assay for flow cytometry (Cell Technology, Inc. Mountain View, CA)":6.
Almagro, J., et al., "Humanization of antibodies" Front Biosci 13:1619-1633 (Jan. 1, 2008).
Anderson, K. et al., "Expression of Human B Cell-Associated Antigens on Leukemias and Lymphomas: A Model of Human B Cell Differentiation" Blood 63(6): (Jun 1, 1984).
Anderson, W. et al., "Human Gene Therapy" Science 256(5058):808-813 (May 8, 1992).
Armour, K. et al., "Recombinant Human IgG Molecules Lacking Fcγ Receptor I Binding and Monocyte Triggering Activities" Eur J Immunol 29(8):2613-2624 (May 10, 1999).
Arnon, R. et al. Monoclonal Antibodies and Cancer Therapy "Chapter 3: Immunotherapy-Monoclonal Antibodies for Immunotargeting of Drugs in Cancer Therapy" (Proceedings of the Roche-UCLA Symposium; Park City, Utah-US, Jan. 26-Feb. 2, 1985), Reisfeld, R., and Sell, S., eds, New York, NY-US:Alan R. Liss, Inc.,:243-256 ( 1985).
Arzoo, K., et al., "Treatment of refractory antibody mediated autoimmune disorders with an anti-CD20 monoclonal antibody (rituximab)" Ann Rheum Dis 61(10):922-924 (Oct. 1, 2002).
Auner, H., et al., "Restoration of erythropoiesis by rituximab in an adult patient with primary acquired pure red cell aplasia refractory to conventional treatment" BR J Haematol 116(3):727-728 (Mar 1, 2002).
Baca, M., et al., "Antibody humanization using monovalent phage display" J Biol Chem 272(16):10678-10684 (Apr. 18, 1997).
Bauduer, F., et al., "Rituximab: a very efficient therapy in cold agglutinins and refractory autoimmune haemolytic anaemia associated with CD20-positive, low-grade non-Hodgkin's lymphoma" BR J Haematol 112(4):1085-1086 (Mar 2001).
Berentsen, S., et al., "Favourable response to therapy with the anti-CD20 monoclonal antibody rituximab in primary chronic cold agglutinin disease" BR J Haematol 115(1):79-83 (Oct 1, 2001).
Berentsen, S., et al., "Rituximab for primary chronic cold agglutinin disease: a prospective study of 37 courses of therapy in 27 patients" Blood 103(8):2925-2928 (Apr. 15, 2004).
Boerner, P., et al., "Production of antigen-specific human monoclonal antibodies from in vitro-primed human splenocytes" J Immunol 147(1):86-95 (Jul. 1, 1991).
Bonifacino, "Commonly J., et al., Used Techniques: Molecular Biology Techniques" Curr Protocols in Cell Biol 8(1):1-4 (Oct 2000).
Brodeur et al. Monoclonal Antibody Production Techniques and Applications New York:Marcel Dekker, Inc.,:51-63 (1987).
Bruggemann et al., "Comparison of the effector functions of human immunoglobulins using a matched set of chimeric antibodies" J Exp Med 166(5):1351-61 (Nov. 1987).
Brunhouse, R., et al., "Isotypes of IgG: comparison of the primary structures of three pairs of isotypes which differ in their ability to activate complement" Mol Immunol 16(11):907-917 (Nov 1, 1979).
Burton, D.R. et al., "The C1q receptor site on immunoglobulin G" Nature 288(5789):338-344 (Nov. 27, 1980).
Cambridge, G. et al., "B lymphocyte depletion in patients with rheumatoid arthritis: serial studies of immunological parameters" Arthritis Rheum (Abstract #1350), 46(9):5506 (Sep. 1, 2002).
Capel, P., et al., "Heterogeneity of human IgG Fc receptors" Immunomethods 4(1):25-34 (Feb. 1, 1994).
Carter, P., et al., "'Knobs-into-holes' provides a rational design strategy for engineering antibody CH3 domains for heavy chain heterodimerization" Immunotechnology 2(1):73 (Jan. 1996).
Carter, P., et al., "Humanization of an Anti-p185$^{HER2}$Antibody For Human Cancer Therapy" PNAS USA 89(10):4285-4289 (May 15, 1992).
Chari, R., et al., "Immunoconjugates containing novel maytansinoids: Promising anticancer drugs" Cancer Res 52(1):127-131 (Jan. 1, 1992).

(56) References Cited

OTHER PUBLICATIONS

Charlton, K.A., "Expression and isolation of recombinant antibody fragments in E. coli" Methods Mol Biol 248:245-254 (2003).
Chowdhury, P., "Engineering hot spots for affinity enhancement of antibodies" Methods Mol Biol 207:179-196 (2008).
Clackson et al., "Making antibody fragments using phage display libraries" Nature 352(6336):624-628 (Aug. 15, 1991).
Clark, E., et al., "Role of Bp35 Cell Surface Polypeptide in Human B-cell Activation" PNAS USA 82(6): 1766-1770 (Mar. 1, 1985).
Clynes, R., et al., "Fc receptors are required in passive and active immunity to melanoma" PNAS USA 95(2):652-656 (Jan. 1, 1998).
Coll, A., et al., "Rituximab therapy for the type B syndrome of severe insulin resistance" New Engl J Med 350(3):310-311 (Jan. 15, 2004).
Cragg, M., et al., "Antibody Specificity Controls in Vivo Effector Mechanisms of Anti-CD20 Regents" Blood 103(7):2738-2743 (Apr. 1, 2004).
Cragg, M., et al., "Complement-mediated lysis by anti-CD20 mAb correlates with segregation into lipid rafts" Blood 101(3):1045-1052 (Feb. 1, 2003).
Cross, A., et al., "Preliminary Results from a Phase II trial of Rituximab in MS" Abstract 8th Ann. Meeting of the Americas Committee, for Research and Treatment in Multiple Sclerosis, San Francisco, CA-US, pp. 20-21 (Oct. 19, 2003).
Cunningham, B., et al., "High-resolution epitope mapping of hGH-receptor interactions by alanine-seaming mutagenesis" Science 244:1081-1085 (Jun. 2, 1989).
"CytoTox 96® non-radioactive cytotoxicity assay (Promega, Madison, WI)":21.
Dall'Acqua, W., et al., "Antibody humanization by framework shuffling" Methods 36(1):43-60 (Jan. 17, 2005).
D'Arena, G., et al., "Late and long-lasting response in an adult chronic idiopathic thromboeytopenie purpura after extended course of rituximab" Leuk Lymphoma 44(3):561-562 (Mar. 1, 2003).
De Haas, M., et al., "Fcγ receptors of phagocytes" J Lab Clin Med 126(4):330-341 (Oct. 1, 1995).
De Vita, S., et al., "Efficacy and Safety of Rituximab Treatment in Type 11 Mixed Cryoglobulinemia" Abstract (Arthritis & Rheum, Abstract #469,) ACR Concurrent Session Vaculitis: Novel Treatment and Pathogenesis, New Orleans, LA-US, pp. S206 (Oct. 26,2002).
De Vita, S., et al., "Efficacy of Selective B Cell Blockade in the Treatment of Rheumatoid Arthritis" Arthritus Rheum 46(8):2029-2033 (Aug. 2002).
Deyev, S., et al., "Modern Technologies for Creating Synthetic Antibodies for Clinical Application" Acta Naturae 11(l):32-50 (Apr. 1, 2009).
Dubowchik, G., et a., "Doxorubicin immunoconjugates containing bivalent, lysosomally-cleavable dipeptide linkages" Bioorg Med Chem Lett 12(11):1529-1532 (Jun. 3, 2002).
Duncan, A., et al., "The Binding Site for Clq on IgG" Nature 332(6166):738-740 (Apr. 21, 1988).
Dupuy, A., et al., "Treatment of refractory pemphigus vulgaris with rituximab (anti-CD20 monoclonal antibody)" Arch Dermatol 140(1):91-96 (Jan. 1, 2004).
Edwards, J., et al., "B-lymphoeyte depletion therapy in rheumatoid arthritis and other autoimmune disorders" Biochem Soc Trans 30(4):824-828 (Aug. 1. 2002).
Edwards, J., et al., "Efficacy and safety of Rituximab, a B-cell targeted chimeric monoclonal antibody: A randomized, placebo-controlled trial in patients with rheumatoid arthritis" Arthritis Rheum (Abstract #446), 46(9):S197 ( 2002).
Edwards, J., et al, "Sustained Improvement in Rheumatoid Arthritis Following a Protocol Designed to Deplete 3B Lymphocytes" Rheumatology 40(2):205-211 (Feb. 1, 2001).
Einfeld, D., et al, "Molecular Cloning of the Human B Cell CD20 Receptor Predicts a Hydrophobic Protein with Multiple Transmembrane Domains" EMBO J 7(3):711-717 (Mar. 1, 1988).
Eisenberg R., "SLE—Rituximab in lupus" Arthritis Res Ther 5(4):157-159 (2003).
Emery et al., "Sustained Efficacy at 48 Weeks after Single treatment Course of Rituximab in patients with Rheumatoid Arthritis" Arthritis Rheum ((Abstract #1095)), 48(9 SUPPL S439) (2003).
English translation of Japanese Office Action (Notification of Reasons for Rejection), dated May 28, 2019, in the related Jananese Patent Application No. 2018-516702.
Eriksson, "Short-term outcome and safety in 5 patients with ANCA-positive vasculitis treated with rituximab" Kidney Blood Press R (Abstract P87), 26:294 (2003).
Flatman, S., et al., "Process analytics for purification of monoclonal antibodies" J Chromatogr 848(1):79-87 (Mar. 15, 2007).
Gazzano-Santoro, H., et al., "A non-radioactive complement-dependent cytotoxicity assay for anti-CD20 monoclonal antibody" J Immunol Methods 202(2): 163-171 (Mar. 28, 1997).
Gerngross, T. U., et al., "Advances in the production of human therapeutic proteins in yeasts and filamentous fungi" NAT BIO-TECH 22(11):1409-1414 (Nov. 1, 2004).
Gessner, J., et al., "The IgG Fc Receptor Family" Ann Hematol 76(6):231-248 (Jun. 1, 1998).
Gorman, C. et al, "Does B cell depletion have a role to play in the treatment of systemic lupus erythematosus?" Lupus 13(5):312-316 (2004).
Graham, F., et al., "Characteristics of a Human Cell Line Transformed by DNA from Human Adenovirus Type 5" J Gen Virol 36(1):59-72 (Jul. 1, 1977).
Guyer, R., et al, "Immuno globulin binding by mouse intestinal epithelial cell receptors" J Immunol 117(2):587-593 (Aug. 1, 1976).
Hellstrom, I et al., "Strong antitumor activities of IgG3 antibodies to a human melanoma-associated ganglioside" PNAS USA 82(5):1499-1502 (Mar. 1, 1985).
Hellstrom, I., et al, "Antitumor effects of L6, an lgG3 antibody that reacts with most human carcinomas" PNAS US 83(18):7059-7063 (Sep. 1, 1986).
Hellstrom, K., et al. Controlled Drug Delivery: Fundamentals and Applications "Chapter 15: Antibodies for Drug Delivery" Robinson, J., and Lee, V., eds., Second edition, Basel, CH and New York, NY-US:Mareel Dekker, Inc., vol. 29:623-642 (1987).
Hezareh, M., et al., "Effector function activities of a panel of mutants of a broadly neutralizing abtibody against human immunodeficiency virus type 1." J Virol 75(24):12161-12168 (Dec. 1, 2001).
Higashida, J., et al., "Treatment of DMARD-Refractory Rheumatoid Arthritis With Rituximab" Poster (Abstract #LB11) Annual Scientific Meeting of the American College of Rheumatology, New Orleans, LA-US, (Oct. 24-29, 2002).
Hinman, L., et al., "Preparation and characterization of monoclonal antibody conjugates of the calicheamicins: A novel and potent family of antitumor antibiotics" Cancer Res 53(14):3336-3342 (Jul. 15, 1993).
Hoogenboom, H., et al., "Overview of antibody phage-display technology and its applications" Methods Mol Biol 178:1-37 (2002).
Idusogie, E. et al., "Mapping of the Clq Binding Site on Rituxan, A Chimeric Antibody with a Human IgG1 Fc" J Immunol 164(8):4178-4184 (Apr. 15, 2000).
Janeway, C., "Autoimmune disease: immunotherapy by peptides?" Nature 341(6242):482-483 (Oct. 12, 1989).
Jayne, D., "Current attitudes to the therapy of vasculitis" Kidney Blood Press R 26(4):231-239 (2003).
Jayne, D., et al., "B-cell depletion with rituxirnab for refractory vasculitis" Kidney Blood Press R (Abstract P88), 26:294-295 (2003).
Jeffrey, S., et al., "Dipeptide-based highly potent doxorubicin antibody conjugates" Bioorg Med Chem Lett 16(2):358-362 (Jan. 15, 2006).
Kabat, E. et al., "Sequences of Proteins of Immunological Interest" 1(Fifth Edition):647-660 (1991).
Kabat, E. et al., "Sequences of Proteins of Immunological Interest" 1(Fifth Edition):661-723 (1991).
Kabat, E., et al. Sequences of Proteins of Immunological Interest 5th edition,NIH,:2 pages (1991).
Kam, N. et al., "Carbon nanotubes as multifunctional biological transporters and near-infrared agents for selective cancer cell destruction" PNAS USA 102(33): 11600-11605 (Aug. 16, 2005).

(56) References Cited

OTHER PUBLICATIONS

Kanda, Y., et al, "Compatison of cell lines for stable production of fucose-negative antibodies with enhanced ADCC" Biotechnol Bioeng 94(4):680-688 (Jul. 5, 2006).
Kashmiri, S., et al., "SDR grafting—a new approach to antibody humanization" Methods 36:25-34 (Jan. 1, 2005).
Kazkaz H., et al., "Anti B cell Therapy (rituximab) in the treatment of autoimmune diseases" Curr Opin Pharmacol 4(4):398-402 (Aug. 1, 2004).
Keogh, K. et al., "Rituximab for Remission Induction in Severe ANCA-Associated Vasculities. A Report of a Prospective Open-Label Pilot Trial in 10 Patients"Abstract (Abstract 605) American College of Rheumatology, Session title: Vasculitis, Orlando, Florida-US, pp. 1 (Oct. 18, 2004).
Kim, J., et al, "Localization of the site of the murine IgG1 molecule that is involved in binding to the murine intestinal Fc receptor" Eur J Immunol 24(10):2429-2434 (Oct. 1, 1994).
Kindt et al. Kuby Immunol Sixth edition, New York: W. H. Freeman and Company,:91 (2007).
King, H., et al., "Monoclonal antibody conjugates of doxorubicin prepared with branched peptide linkers: Inhibition of aggregation by methoxytriethyleneglycol chains" J Med Chem 45(19):4336-4343 (Sep. 12, 2002).
Klemmer, N., et al., "Treatment of antibody mediated autoimmune disorders with a Anti-CD20 monoclonal antibody Rituximab" Arthritis Rheum (Abstract #1623), 48(Suppl Suppl 9):S624 (Sep. 1, 2003).
Klimka, A., et al., "Human anti-CD30 recombinant antibodies by guided phage antibody selection using cell panning" Br J Cancer 83(2):252-260 (Mar. 1, 2000).
Kneitz, C., et al., "Effective B cell depletion with rituximab in the treatment of autoimmune diseases" Immunobiology 206(5):519-527 (Dec. 1, 2002).
Kozbor, D., et al., "A Human Hybrid Myeloma for Production of Human Monoclonal Antibodies" J Immunol 133(6):3001-3005 (Dec. 1, 1984).
Kratz, F., et al., "Prodrugs of anthracyclines in cancer chemotherapy" Curr Med Chem 13(5):477-523 (2006).
Lake and Dionne et al. Burger's Medicinal Chemistry and Drug Discovery "6" Abraham, 6th edition, Hoboken: John Wiley & Sons, Inc., vol. 5:223-247 (2003).
Layios, N., et al., "Remission of severe cold agglutinin disease after Rituximab therapy" Leukemia 15(1):187-188 (Jan. 1, 2001).
Leandro, M., et al, "An open study of B lymphocyte depletion in systemic lupus erythematosus" Arthritis Rheum 46(10):2673-2677 (Oct. 1, 2002).
Leandro, M., et al., "B cell repopulation occurs mainly from naive B cells in patients with rheumatoid arthritis and systemic lupus erythematosus treated with rituximab" Arthritis Rheum (Abstract #1160), 48( Suppl Suppl 9):S464 (Oct. 27, 2003).
Leandro, M., et al., "Clinical outcome in 22 patients with rheumatoid arthritis treated with B lymphocyte idepletion" Ann Rheum Dis 61(10):883-888 (Oct. 1. 2002).
Leandro, M., et al., "Clinical outcome in 22 patients with rheumatoid arthritis treated with B lymphocyte depletion" Ann Rheum Dis 61(10):883-888 (Oct. 1. 2002).
Levine, "A Pilot Study of RituXimab Therapy for RefractOIy Dermatomyositis" Arthritis Rheum (Abstract #1299), 46( Suppl Suppl 9):S488-S489 (2002).
Levine, T., et al., "IgM antibody-related polyneuropathies: B-cell depletion chemotherapy using Rituximab" Neurology 52(8):1701-1704 (May 12, 1999).
Li, H., et al., "Optimization of humanized IgGs in glycoengineered Pichia paston's" Nat Biotechnol 24(2):210-215 (Feb. 1, 2006).
Li, J., et al., "Human antibodies for immunotherapy development generated Via a human B cell hybridoma technology" PNAS USA 103(10):3557-3562 (Mar. 7, 2006).
Liang and Tedder et al. Wiley Encyclopedia of Molecular Medicine John Wiley & Sons, Inc, New York: John Wiley,:562-564 (Jan. 15, 2002).
Lode et al., "Targeted therapy with a novel enediyene antibiotic calicheamiein V11 effectively suppresses growth and dissemination of liver metastases in a syngeneie model of murine neuroblastoma" Cancer Res 58:2925-2928 (1998).
Lonberg, N., "Human antibodies from transgenic animals" Nat Biotechnol 23(9): 1117-11125 (2005).
Lonberg, N., "Fully human antibodies from transgenic mouse and phage display platforms" Current Opin Immunol 20(4):450-459 (Aug. 1, 2008).
Looney, R. J., "Treating human autoimmune disease by depleting B cells" Ann Rheum Dis 61(10):863-866 (Oct 1. 2002).
Lukas, T. J., et al., "Inhibition of C1-mediated immune hemolysis by monomeric and dimeric peptides from the second constant domain of human immunoglobulin G" J Immunol 127(6):2555-2560 (Dec. 1, 1981).
Lund, J., et al., "Oligosaeehatide-protein interactions in IgG can modulate recognition by Fc gamma receptors" FASEB J. 9(1):115-119(Jan. 1, 1995).
MacCallum, R., et al., "Antibody-antigen Interactions: Contact Analysis and Binding Site Topography" J Mol Biol 262(5):732-745 (Oct. 11, 1996).
Martin and Chan et al., "Pathogenic roles of B cells in human autoimmunity; insights from the clinic" Immunity 20(5):517-527 (May 2004).
Mather, J., et al, "Culture of Testicular Cells in Hormone-Supplemented Serum-Free Medium" Ann NY Acad Sci 383:44-68 (1982).
Mather, Jennie P., "Establishment and Characterization of Two Distinct Mouse Testicular Epithelial Cell Lines" Biol Reprod 23:243-252 (1980).
Merchant, A., et al., "An efficient route to human bispecific IgG" Nat Biotechnol 16(7):677-681 (Jul. 1, 1998).
Morgan, A, et al., "The N-terminal end of the CH2 domain of chimeric human IgG1 anti-HLA-DR is necessary for C1q, Fc gamma RI and Fc gamma RIII binding" Immunology 86(2):319-324 (Oct. 1, 1995).
Morrison, S., et al., "Chimeric human antibody molecules: Mouse antigen-binding domains with human constant region domains" PNAS 81(21):6851-6855 (Nov. 1, 1984).
Nagy, A., et al., "Stability of cytotoxic luteinizing hormone-releasing hormone conjugate (AN-152) containing doxorubicin 14-O-hemiglutarate in mouse and human serum in vitro: implications for the design of preclinical studies" PNAS USA 97(2):829-834 (Jan. 18, 2000).
Ni, "Research progress and future perspectives in antibodornies and antibodornie drugs" Xiandai Mianyixue ((Abstract only)), 26(4):265-268 (2006).
Niewoehner, J., et al., "Increased Brain Penetration and Potency of a Therapeutic Antibody Using a Monovalent Molecular Shuttle" Neuron 81(1):49-60 (Jan. 8, 2014).
Offner, H. et al, "T cell receptor peptide therapy triggers autoregulation of experimental eneephalomyelitis" Science 251(4992):430-432 (Jan. 25, 1991).
Okazaki et al., "Fueose depletion from human IgG1 oligosacchride enhances binding enthalpy and association rate between IgG1 and FcgammaRIIIa" J Mol Biol 336(5): 1239-1249 (Mar. 5, 2004).
Osbourn, J. et al., "From rodent reagents to human therapeutics using antibody guided selection" Methods 36(1):61-68 (May 1, 2005).
Osol, A. Remington's Pharmaceutical Sciences 16 edition, (1980).
Pace, C., et al., "How to measure and predict the molar absorption coefficient of a protein" Protein Sci 4(11):2411-2423 (Nov. 1, 1995).
Padlan, E., "A possible procedure for reducing the immunogenieity of antibody variable domains while preserving their ligand-binding properties" Mol Immunol 28(4-5):489-498 (Apr. 30, 1991).
Penichet and Morrison et al. Wiley Encyclopedia of Molecular Medicine (Section: Chimeric, Humanized and Human Antibodies), John Wiley & Sons Inc., New York: John Wiley,:214-216 (2002).
Perotta, A., et al., "Response of Chronic Relapsing ITP of 10 years duration to Rituximab" Blood (Abstract #3360 ;Part 1-2), 92(10 Suppl 1):88b (Nov. 15, 1998).
Perotta, A., et al., "Rituxan in the Treatment of Chronic Idiopathic Thrombocytopenic" Blood (Abstract #49), 94(14):4a(1999).

(56) References Cited

OTHER PUBLICATIONS

Pestronk, A., et al., "Treatment of IgM antibody associated polyneuropathies using rituximab" J Neurol Neurosurg Psychiatry 74(4):485-489 (Apr. 1, 2003).

Petkova, S., et al., "Enhanced half-life of genetically engineered human IgG1 antibodies in a humanized FcRn mouse model: potential application in humorally mediated autoimmune disease" Int Immunol 18(12):1759-1769 (Dec. 1, 2006).

Portolano, S., et al., "Lack of promiscuity in autoantigen-specific H and L chain combinations as revealed by human H and L chain 'roulette'" J Imunol 150(3):880-887 (Feb. 1, 1993).

Pranzatelli, M., et al., "CSF B-Cell Over-Expansion in Paraneoplastic Opsoclonus-Myoclonus: Effect of Rituximab, an Anti-B-Cell Monoclonal Antibody" Neurology (Abstract #P05.128), 60(5 Suppl 1):A395 (Mar. 2003).

Press, O., et al., "Monoclonal Antibody 1F5 (Anti-CD20) Serotherapy of Human B Cell Lymphomas" Blood 369(2):584-591 (Feb. 1, 1987).

Presta, L., et al., "Humanization of an Antibody Directed Against IgE" J Immunol 151(5):2623-2632 (Sep. 1, 1993).

Queen, C., et al., "A humanized antibody that binds to the interleukin 2 receptor" PNAS USA 86(24):10029-10033 (Dec. 1, 1989).

Ratanatharathorn, V., et al., "Anti-CD20 chimeric monoclonal antibody treatment of refractory immune-mediated thromboeytopenia in a patient with chronic graft-versus-host disease" Ann Intern Med 133(4):275-279 (Aug. 15, 2000).

Ravetch and Kinet, "Fc receptors" Ann Rev Immunol 9:457-492 (1991).

Ravetch. J. et al., "IgG Fc receptors" Ann Rev Immunol 19:275-290 (2001).

Reff, M., et al., "Depletion of B cells in Vivo by a chimeric mouse human monoclonal antibody to CD20" Blood 83(2):435-445 (Jan. 15, 1994).

Riechmann, L.,, "Reshaping human antibodies for therapy" Nature 332(6162):323-327 (Mar. 24, 1988).

Ripka, J., et al., "Two Chinese hamster ovary glyeosylation mutants affected in the conversion of GDP-mannose to GDP-fucose" Arch Biochem Biophys 249(2):533-545 (Sep. 1, 1986).

Rosok, M., et al., "A combinatorial library strategy for the rapid hurnarrization of anticarcinorna BR96 Fab" J Biol Chem 271(37):22611-22618 (Sep. 13, 1996).

Saleh, M., et al., "A pilot study of the anti-CD20 monoclonal antibody rituXimab in patients with refractory immune thrombocytopenia" Semin Oncol 27(6 Suppl Supp 12):99-103 (Dec. 1, 2000).

Sambrook et al. Molecular Cloning: A Laboratory Manual Second edition, New York: Cold Spring Harbor Laboratory Press, (1989).

Schneider et al., "Primary structure of human transferrin receptor deduced from the mRNA sequence" Nature 311:675-678 (Oct. 18, 1984).

Shields et al., "High Resolution Mapping of the Binding Site on Human IgG1 for FcγRI, FcγRII, FcγRIII, and FcRn and Design of IgG1 Vanants with Improved Binding to the FcγR" J Biol Chem 276(9):6591-6604 (2001).

Silverrnan and Weisrnan et al., "Rituximab therapy and autoimmune disorders: prospects for anti-B cell therapy" Arthritis Rheum 48(6): 1484-1492 (Jun. 2003).

Sims, M., et al, "A Humanized CD18 Antibody Can Block Function Without Cell Destruction" J Immunol 151(4):2296-2308 (Aug. 15, 1993).

Somer et al. et al., "Improvement in Sjogren's syndrome following therapy with rituximab for marginal zone lymphoma" Arthritis Rheum 49(3):394-398 (Jun. 15, 2003)

Specks, U., et al., "Response of Wegener's Granulomatosis to anti-CD20 chimeric monoclonal antibody therapy" Arthritis Rheum 44(12):2836-2840 (Dec. 2001)

Stahl, H., et al., "Rituximab in RA: Efficacy and safety from a randomised, controlled trial" Ann Rheum Dis 362(Suppl 1) ( 2003).

Stasi, R., et al., "Rituximab chimeric anti-CD20 monoclonal antibody treatment for adults with chronic idiopathic thrombocytopenic purpura" Blood 98(4):952-957 (Aug. 15, 2001)

Stockinger, H., et al. Current Protocols in Immunology "Appendix: Monoclonal Antibodies to Human Cell Surface Antigens" New York, NY-US: John Wiley & Sons, vol. 53(1):A.4A.1-A.4A.49 (May 15, 2003).

Stone, J., et al., "Rituximab Therapy For The Induction Of Remission and Tolerance In ANCA-Associated Vasculitis" Clinical Trial Research Sunnnary (Immune Tolerance Network),:1-2 (Sep. 28, 2004) https://web.archive.org/web/20080724222641/http://www.immunetolerance.org/research/autoimmune/trials/stone.html.

Tedder, T., et al., "The B Cell Surface Molecule B1 is Functionally Linked with B Cell Activation and Differentiation" J Immunol 135(2):973-979 (Aug. 1, 1985).

Tedder, T., et al., "The CD20 Surface Molecule of B Lymphocytes Functions as a Calcium Channel" J Cell Biochem (Abstract #M 023), 14D:195 (1990).

Teeling, J et al., "Characteiization of new human CD20 monoclonal antibodies with potent cytolytic activity against non-Hodgkin lymphomas" Blood 104(6):1793-1800 (Sep. 15, 2004).

Thommesen, J., et al., "Lysine 322 in the human IgG3 C(H)2 domain is crucial for antibody dependent complement activation" Mol Immunol 37(16):995-1004 (Nov. 1, 2000).

Thorpe, P., et al., "The Preparation and Cytotoxic Properties Of Antibody-Toxin Conjugates," Immunol. Rev. 62:119-158 (1982).

Thorpe, Monoclonal Antibodies 84: Biological and Clinical Applications A. Pinchera, G. Doria, F. Dammacco & Bargellesi, Editrice Kurtis S.R.L. (Publisher),:475-506 (1985).

Torgov, M., et al, "Generation of an intensely potent anthracycline by a monoclonal antibodyn—β-galactosidase conjugate" Bioconjugate Chem 16(3):7 17-21 (May 1, 2005).

Torres, M., et al., "The immunoglobulin constant region contributes to affinity and specificity" Trend Immunol 29(2):91-97 (Feb. 1, 2008).

Tuscano et al., "Successful treatment of Infliximab-refractory rheumatoid arthritis with rituximab" Poster (Presentation #LB11, Poster #444, from OASIS—Online Abstract Submission and Invitation System) Annual Scientific Meeting of the American College of Rheumatology, New Orleans, LA-US, ( Oct. 24-29, 2002).

Urlaub, G., et al., "Isolation of Chinese hamster cell mutants deficient in dihydrofolate reductase activity" PNAS USA 77(7):4216-4220 (Jul. 1980).

Valentine et al., "B3.9 Structure and function of the B-cell specific 35-37 kDa CD20 protein" Leukocyte Typing III (B-cell antigens—papers),:440-443 ( 1987).

Valentine, M., et al., "Phosphorylation of the CD20 Phosphoprotein in Resting B Lymphocytes" J Biol Chem 264(19):11282-11287 (Jul. 5, 1989).

van de Winkel Ct 211., "Biology og human immunogoblin G Fc receptors" J Leukocyte Biol 49(5):511-524 (May 1991).

van Dijk and van de Winkel, "Human antibodies as next generation therapeutics" Curr Opin Chem Biol 5(4):368-74 (Aug. 2001).

Virgolini, L., et al., "Rituximab in autoimmune diseases" Biomed Pharmacother 58(5):299-309 (Jun. 1, 2004).

Vitetta et al., "Redesigning nature's poisons to create anti-tumor reagents" Science 238: 1098-1104 ( 1987).

Vollmers, H., et al., "The 'early birds': Natural IgM antibodies and immune surveillance" Histol Histopathol 20(3):927-937 (Jul. 1, 2005).

Vollmers, H.,, "Death by stress: natural IgM-induced apoptosis" Methods Find Exp Clin Pharmacol 27(3):185-191 (Apr. 1, 2005).

Wagner, E., et al., "Transferrin-Polyeation Conjugates as Carriers for DNA Uptake Into Cells" PNAS USA 37(9):3410-3414 (May 1, 1990).

Weide, R., et al., "Successful long-term treatment of systemic lupus erythematosus with rituximab maintenano therapy" Lupus 12(10):779-782 ( 2003).

Wright, A., et al., "Effect of glycosylation on antibody function: Implications for genetic engineeting" Trends Biotechnol 15(1):26-32 (Jan. 1, 1997).

(56) References Cited

OTHER PUBLICATIONS

Wu, G.Y. and C. H. Wu, "Receptor-Mediated in Vitro Gene Transformation by a Soluble DNA Cartier System" J Biol Chem 262(10):4429-4432 (Apr. 5, 1987)
Wylam, M., et al., "Successful treatment of refractory myasthenia gravis using rituxirnab: a pediatric case report" J Pediatr 143(5):674-677 (Nov. 1, 2003).
Yamane-Ohnuki et al., "Establishment of FUT8 knockout Chinese hamster ovary cells: an ideal host cell line for producing completely defucosylated antibodies with enhanced antibody-dependent cellular cytotoxicity" Biotechnol Bioeng 87(5):614-622 (Sep. 5, 2004).
Yazaki et al. Methods in Molecular Biology "Expression of recombinant antibodies in mammalian cell lines" Lo, B.K.C. (ed.), Totowa, NJ: Humana Press, vol. 248:255-268 ( 2004).
Zaja, F., et al., "B-cell depletion with rituximab as treatment for immune hemolytie anemia and chronic thrombocytopenia" Haematologica 87(2):189-195 (Feb. 1, 2002).
Zaja, F., et al., "Efficacy and safety of rituximab in type II mixed cryoglobulinemja" Blood 101(10):3827-3834 (May 15, 2003).
Zaja, F., et al., "Rituximab for myasthenia gravis developing after bone marrow transplant" Neurology 55(7):1062-1063 (Oct. 10, 2000).
Zaja, F., et al., "Rituximab in a case of cold agglutinin disease" BR J Haematol 115(1):232-233 (Oct. 1, 2001).
English translation of Office Action issued by the Taiwan Patent Office in ROC (Taiwan) Patent Application No. 095146304, dated Aug. 20, 2012.
Pardridge, W.M., "Re-Engineering Biopharmaceuticals for Delivery to Brain with Molecular Trojan Horses" Bioconjugate Chemistry 19(7):1327-1338 ( 2008).
Zhang, J. et al., "Design and optimization Yes !Natural Science 19(10):1197-1200 of a linker for fusion protein construction" Progress in Natural Science 19(10):1197-1200 (2009).
GenBank_NCBI_Accession No. AGB75998, Zhai et al.
Pardridge et al., "Selective Transport of an Anti-Transferrin Receptor Antibody Through the Blood-Brain Barrier in Vivo" Journal of Pharmacology and Experimental Therapeutics 259(1):66-70 ( 1991)
Ulbrieh et al., "Transferrin- and transferrin-receptor-antibody-modified nanoparticles enable drug delivery across the blood-brain barrier (BBB)" European Journal of Pharmaceutics and Biopharmaceutics 71:251-256 ( 2009).
Yan et al., "Soluble expression and target study to brain of anti-TfRScFv" Chinese Journal of Biotechnology (English abstract), 20(3):342-347 ( 2004).
Zhao et al., "Expression, purification and activity analysis of anti-human transferrin receptor scFv" Chinese Journal of Biotechnology (English abstract), 22(3):488-491 ( 2006).
(Author Not Identified) Remington's Pharmaceutical Sciences (Table of Contents, total in 4 pages), OSOL et al., 16th edition, Easton, Pennsylvania:Mack Publishing Company, ( 1980).
(International Search Report on patentability for International Patent Application No. PCT/EP2014/079353).
(Written Opinion of the International Searching Authority for International Patent Application No. PCT/EP2014/079353).
Bien-Ly et al., "Transferrin receptor (TfR) trafficking determines brain uptake of TfR antibody affinity variants" J. Exp. Med. 211(2):233-244 ( 2014).
Boado et al., "Drug targeting of erythropoietin across the primate blood-brain barrier with an IgG molecular Trojan horse" J Pharm Exp Ther, Am Soc Pharm Exp Ther 333(3):961-969 (Jun. 1, 2010).
Boado, R., et al., "Engineering and expression of a chimeric transferrin receptor monoclonal antibody for blood-brain barrier delivery in the mouse" Biotechnol Bioeng 102(4):1251-1258 (Mar. 1, 2009).
Boado, R.J. et al., "Selective targeting of a TNFR decoy receptor pharmaceutical to the primate brain as a receptor-specific IgG fusion protein" J Biotechnol 146(1-2):84-91 (Mar. 1, 2010).

Chen, C., et al., "Enhancement and Destruction of Antibody Function by Somatic Mutation: Unequal Occurrence is Controlled by V Gene Combinatorial Associations" EMBO J 14(12):2784-2794 (Jun. 15, 1995).
Cheong et al., "Affinity enhancement of bispecific antibody against two different epitopes in the same antigen" Biochemical and Biophysical Research Communications 173(3):795-800 (Dec. 31, 1990).
Chothia et al., "Canonical structures for the hypervariable regions of immunoglobulins" J Mol Biol 196(4):901-917 (Apr. 23, 1987).
Coloma et al., "Position Effects of Variable Region Carbohydrate on the Affinity and In Vivo Behavior of an Anti-(1-6) Dextran Antibody" Journal of Immunology 162:2162-2170 ( 1999).
Communieation Pursuant to Article 94(3) EPC issued by the European Patent Office, dated Sep. 2, 2009, in related European Patent Appl. No. 06 829 502.1.
Comoglio, P. et al., "Drug development of MET inhibitors: targeting oncogene addiction and expedience" Nature 73:504-5 16 (Jun. 2008).
Cover page with English translation of Office Action issued by the Peruvian Patent Office, dated Feb. 10, 2010.
Cribbs et al., "Adjuvant-dependent modulation of Th1 and Th2 responses to immunization with b-amyloid" International Immunology 15(4):505-514 ( 2003).
Di Zenzo, G. et al., The Intracellular and Extracellular Domains of BP180 Antigen Comprise Novel Epitopes Targeted by Pemphigoid Gestationis Autoantibodies J. of Investigative Dermatology 127:864-873 (Mar. 19, 2006).
Endo et al., "Glycosylation of the variable region of immuno globulin G—site specific maturation of the sugar chains" Mol Immunol 32(13):931-940 ( 1995).
English translation Notice of the Result of Substantive Examination of a Patent Application issued by the Patents Office of the Cooperation Council for the Arab States of the Gulf GCC, dated Jan. 2, 2010, in related Appl. No. 7376.
English translation of Notice of Grounds for Rejection in Japanese Patent Application No. 2009-053951, dispatched on Aug. 11, 2011.
English translation of Notice of Preliminary Rejection and cited references issued by the Korean Patent Office, dated Jan. 13, 2011, in related Korean Patent Application No. 7012289/2008.
English translation of Office Action and Search Report issued by the Taiwanese Patent Office, dated Jul. 22, 2009, in related Patent Application No. 095146304.
English translation of Office Action issued by Israeli Patent Office dated Jul. 14, 2010, in related Israeli Patent Application No. 191004.
English translation of Office Action issued by the Mexican Patent Office, dated Mar. 18, 2011, in related Mexican Patent Appl. No. MX/a/2008/006948.
English translation of Office Action issued by the Pakistani Patent Office, dated Jul. 30, 2009, in related Pakistani Patent Appl. No. 162912006.
English translation of Office Action issued by the Russian Patent Office, dated Sep. 23, 2010, in related Russian Patent Application 2008 128 138.
English translation of Office Action issued by the Russian Patent Office, dated Mar. 23, 2011, in related Russian batent Application 2008 128 138.
English translation of Office Action issued by the State Intellectual Property Office of the PRC, dated Dec. 28, 2010, in related Chinese Application No: 200680046307.9.
English translation of Office Action—Preliminary Examination Report issued by the Ukrainian Patent Office, dated Jun. 14, 2011, in related Ukranian Patent Application No. a 20080879.
Examiner's First Report issued by the Australian Patent Office, dated Aug. 23, 2010, in related Australian patent application No. 2006326301.
Felgenhauer et al., "Protein size and cerebrospinal fluid composition"Klin. Wschr 52:1158-1164 ( 1974).
Frenkel et al., "High affinity binding of monoclonal antibodies to the sequential epitope EFRH of b-amyloid peptide is essential for modulation of fibIillaI aggregation" Journal of Immunology 95:136-142 (1999).

(56) References Cited

OTHER PUBLICATIONS

Frenkel et al., "N-terminal EFRH sequence of Alzheimer's b-amyloid epitope of its anti-aggregating antibodies" Journal of Neuroimmunology 88:85-90 ( 1998).

Ghoshal et al., "Tau-66: evidence for a novel tau conformation in Alzheimer's disease" Journal of Neurochemistry 77:1372-1385 (2001).

Glenner et al., "Alzheimer's Disease and Dowi\'s Syndrome: Sharing of a Unique Cerebrovascular Amyloid Fibril Protein" Biochem Biophys Res Commun. 122(3):1131-1135 ( 1984).

Hardy, "Amyloid, the presenjlins and Alzheimer's disease" Trends Neurosci. 20:154-159 ( 1997).

Harper et al., "Models of Amyloid Seeding in Alzheimer's Disease and Scrapie: Mechanistic Truths and Physiological Consequences of the Time-Dependent Solubility of Amyloid Proteins" Annu. Rev. Biochem. 66:385-407 ( 1997).

Hust, M., et al., "Single chain Fab (scFab) fragment" BMC Biotechnol 7(14):1-15 (Mar. 8, 2007).

International Search Report and Written Opinion (dated Mar. 6, 2014) for International Patent Application No. PCT/ EP2013/067595.

International Search Report and Written Opinion for PCT/EP 2016/73413 dated Jan. 9, 2017.

International Search Report and Written Opinion prepared by the European Patent Office dated Apr. 8, 2015, for International Application No. PCT/EP2014/079353.

International Search Report and Written Opinion prepared by the European Patent Offce dated Jan. 23, 2016, for International Application No.PCT/EP2016/064460.

International Search Report PCT/EP2016/073411 dated Dec. 14, 2016.

ISR and Written Opinion of PCT/EP2016/064460 (dated Sep. 13, 2016).

Jarrett et al., Cell 73:1055-1058 ( 1993).

Kabat et al, "Sequences of Proteins of Immunological Interest" NIH Publication NIH 91-3242 (Fifth Edition), I:647-669 ( 1991).

Kay et al. et al., "An M13 phage library displaying random 38-amino-aeid peptides as a source of novel sequences with affinity to selected targets" Gene 128:59-65 ( 1993).

Klein C. et al., "Progress in overcoming the chain association issue in bispecific heterodimeric IgG antibodies" MAbs 4(6):653-663 (Jan. 11, 2012).

Knappik et al., "Fully Synthetic Human Combinatorial Antibody Libraries (HuCAL) Based on Modular Consensus Frameworks and CDRs Randomized with Trinueleotides" J. Mol. Biol. 296(1):57-86 (Feb. 11, 2000).

Kontermann et al., "Dual targeting strategies with bispecific antibodies" MABS 4(2):182-197 ( 2012).

Koo et al., "Amyloid diseases: Abnormal protein aggregation in neurodegeneration" PNAS 96:9989-9990 ( 1999).

Kussie et al., "A Single Engineered Amino Acid Substitution Changes Antibody Fine Specificity" Journal of Immunology 152:146-152 ( 1994).

Leibiger et al., "Variable domain-linked oligosaccharides of a human monoclonal IgG : structure and influence on antigen binding" Biochem. J. 338:529-538 ( 1999).

Li et al., "Antibody conjugation Via one and two C-terminal selenocysteines" Methods 65:133-138 ( 2014).

Lu, D. et al., "Acquired antagonistic activity of a bispecific diabody directed against two different epitopes on vascular endothelial growth factor receptor 2" J. of Immunological Methods 230:159-171 ( 1999).

Nagy, A., et al., "Stability of cytotoxic luteinizing hormone-releasing hormone conjugate (AN-152) containing doxorubicin 14-O-hemiglutarate in mouse and human semm in vitro: Implications for the design of preclinical studies" PNAS USA 97 (2):829-834 (Jan. 18, 2000).

Office Action issued by Canadian Patent Office, dated Oct. 31, 2011, in related Canadian Patent Appl. No. 2632828.

Office Action issued by the Chilean Patent Office, dated Dec. 11, 2006, in related Chilean Appl. No. 3436-2006.

Office Action issued by the Colombian Patent Office in Application No. 2008 049920-A, dated Sep. 6, 2012.

Office Action issued by the Malaysian Patent Office in Application No. P1 20081349, dated Nov. 14, 2012

Office Action issued by the New Zealand Patent Office, dated Apr. 13, 2010, in related New Zealand Patent Appl. No. 068241.

O'Nuallain, B. et al., "Conformational Abs recognizing a genetic amyloid fibril epitope" PNAS 99(3):1485-1490 ( 2002).

Pakula, A. et al., "Genetic Analysis of Protein Stability and Function" Annu. Rev. Genet. 23:189-310 ( 1989).

Pardridge, W.M. et al., "Drug transport across the blood-brain barrier" J Cerebral Blood Flow Metab 32:1959-1972 ( 2012).

Paul, William E., "Fundamental Immunology" Raven Press( SUPPL Chpt. 8):292-295 ( 1993).

Polysorbate 80_Wikipedia_Mar. 28, 2011.

Press et al., "Monoclonal antibody 1F5 (Anti-CD20) serotherapy of human B cell lymphomas" Blood 69(2):584-591 ( 1987).

Price et al., "Genetic Neurodegenerative Diseases: The Human Illness and Transgenic Models" Science 282(5391):1079-1083 ( 1988).

Raju, T., "Glycosylation variations with expression systems and their impact on biological activity of therapeutic immunoglobulins" Bioprocess Intl 1:44-53 (Apr. 1, 2003).

Richards et al., "PS2APP Transgenic Mice, Coexpressing hPS2mut and hAPPswe, Show Age-Related Cognitive Deficits Associated with Discrete Brain Amyloid Deposition and Inflammation" Journal of Neuroscience 23(26):8989-9003 ( 2003).

Ridgway, J., et al., "Knobs-into-holes' engineeiing of antibody CH3 domains for heavy chain heterodimenzation" Protein Eng 9(7):617-621 (Jul. 1, 1996).

Routier, F., et al., "The glyeosylation pattern of a humanized IgGI antibody (D1.3) expressed in CHO cells" Glyconjugate J 14(2):201-207 (Feb. 1, 1997).

Rudikoff et al., "Single amino acid substitution altering antigen-binding specificity" P Natl Acad Sci USA 79:1979-1983 (Mar. 1982).

Schier et al., "Isolation of picomolar affinity anti-c-erbB-2 single-chain FV by molecular evolution of the complementarity determining regions in the center of the antibody binding site" Journal of Molecular Biology 263(4):551-567 (Nov. 8, 1996).

Selkoe, "Cell Biology of the Amyloid-Protein Precursor and the Mechanism of Alzheimer's Disease" Annual Rev. Cell Biol. 10:373-403 ( 1994).

Sheeley et al., "Characterization of Monoclonal Antibody Glycosylation: Comparison of Expression Systems and Identification of Terminal αLinked Galactose" Analytical Biochemistry 247:102-110 (1997).

Shen-Xin et al, "Study on in Vitro anti-tumor effect of anti-human transferrin receptor monoclonal antibody" Chin. J. Cell Mol Immunol (EN-Abstract), 24(2):144-146 ( 2008).

Singapore Examination Report issued by the Danish Patent Office, dated Jan. 13, 2011, in Appl. No. 200803302-9.

Singapore Written Opinion and Search Report issued by the Danish Patent Office, dated Feb. 10, 2010, in Appl. No. 200803302-9.

Sinha et al., "Cellular mechanisms of b-amyloid production and secretion" PNAS 96:11049-11053 ( 1999).

Sisodia, "B-Amyloid precursor protein cleavage by a membrane-bound protease" PNAS 589:6075-6079 ( 1992).

Solomon et al., "Activity of monoclonal antibodies in prevention of in vitro aggregation of their iantigens" Stability and Stabilization of Bioeatalysts:183-188 ( 1998).

Solomon et al., "Disaggregation of Alzheimer b-amyloid by site-directed mAb" PNAS 94:4109-4112 ( 1997).

Solomon et al., "Monoclonal antibodies inhibit in vitro fibiillar aggregation of the Alzheimei B-amyloid peptide" PNAS 93:452-455 ( 1996).

Solomon et al., "Vaccination for the Prevention and Treatment of Alzheimer's Disease" Drugs of Today 36(9):655-663 ( 2000).

Spiess, C., et al., "Alternative molecular formats and therapeutic applications for bispecific antibodies" Mol Immunol 67(SUPPL 2 Pt A):95-106 (Jan. 27, 2015).

(56) References Cited

OTHER PUBLICATIONS

The Brazilian Preliminary Office Action, dated Nov. 5, 2020, in the related Brazilian Appl. No. BR112018004828-3.
The Brazilian Preliminary Office Action, dated Nov. 5, 2020, in the counter-related Brazilian Appl. No. BR112018004733-3.
The English translation of the Chinese Office Action, dated Nov. 3, 2020, in the related Chinese Patent application No. 2016800371691.
The English translation of the Russian Office Action, dated Mar. 27, 2020, in the related Russian Patent Appl. No. 2018113507/10(021205).
The English translation of the Ukrainian Office Action, dated September 9, 2020, in the related Ukrainian Patent application No. a 201800597.
The European Office Action, dated Oct. 12, 2020, in the related European Patent Appl. No. 16 774 687.4.
Tobinai et al., "A Review of Obinutuzumab (GA101), a Novel Type II Anti-CD20 Monoclonal Antibody, for the Treatment of Patients with B-Cell Malignancies" Adv Ther 34:324-356 ( 2017).
Wagner et al., "Modulation of amyloid β protein precursor processing as a means of retarding progression of Alzheimer's disease" J. Clin. Invest. 104(10):1329-1332 ( 1999).
Weisser, N., et al., "Applications of single-chain valiable fragment antibodies in therapeutics" Biotechnol Adv 27 (4):502-520 (Jul. 31, 2009).
WHO Drug Information, vol. 26, No. 4, 2012 p. 401.
Written Opinion of the International Searching Authority PCT/EP2016/073411 dated Dec. 13, 2016.
Yu et al., "Boosting Brain Uptake of a Therapeutic Antibody by Reducing Its Affinity for a Transcytosis Target" Science Translational Medicine 3(84):8 pages ( 2011).
Yu et al., "Boosting brain uptake of a therapeutic antibody by reducing its affinity for a transcytosis target" Science Translat. Med. 3(84):84ra44 (May 25, 2011).
Yu, J. Y. et al., "Developing therapeutic antibodies for neurodegenerative disease" Neurotherapeutics 10(3):459-472 (Apr. 3, 2013).
Supreme People's Court of People's Republic of China Administrative Judgement (2019) Zui Gao Fa Zhi XingZhong No. 235.
Acton R & D Systems Glial Cell Line-Derived Neurotrophic Factors : Advances in Research and Application 2011 Edition (1996).
Ales Berlec et al., "Current state and recent advances in biopharmaceutical production in *Escherichia coli*, yeasts and mannnalian cells" Journal of Industrial Microbiology & Biotechnology 40:257-274 ( 2013).
Arai, R. et al., "Design of the linkers which effectively separate domains of a bifunetional fusion protein" Protein Engineeiing 14(8):529-532 ( 2001).
Biotechnology ((Russian)), 3:3-8 ( 2000).
Bulbarelli et al., Journal of Cell Science 115:1689-1702 (2002).
Chen, X. et al., "Fusion Protein Linkers: Property, Design and Functionality" Adv Drug Deliv Rev 65(10):1357-1369 (Oct. 15, 2013).
Gulko et al., Biotechnology 3:3-8 ( 2000).
Jost et al., The Journal of Biological Chemistry 269(42):26267-26273 ( 1994).
EKjeldsen et al., Gene 170:107-112 ( 1996).
Li et al., Acta Theriologica Sinica 26(1):38-43 ( 2006).
Lim, Y. et al., "Engineering mammalian cells in bioproeessing—current achievements and ifuture perspectives" Biotechnol. Appl. Biochem. 55:17 5-189 (2010).
Lo et al. et al.., "High level expression and secretion of Fc-X fusion proteins in mannnalian cell" Protein Eng 11(6):495-500 ( 1998).
Meder et al., Journal of Cell Biology 168(2):303-313 ( 2005).
NCBI_IGF-1_P01343.
Nestler et al., Molecular Neuropharmacology (Chapter 8),:199, 211-219 ( 2009).
Paul et al., Fundamental Immunology, 3rd ed. Raven Press, NY, Chap. 9, p. 292-295.
Perlman et al., The Journal of Clinical Endocrinology & Stimulating Hormone 88(7):3227-3235 ( 2003).
Seidah et al., Biochem. J. 314:951-960 ( 1996).
Weissmiller et al., Translational Neurodegeneration 1(14):1-9 (2012).
Chen et al., "Modern methods for delivery of drugs across the blood-brain barrier" Advanced Drug Delivery Reviews 64:640-665 ( 2012).
Zhai et al., "GenBank NCBI) Accesion No. AGB. 75998":1 (Sep. 23, 2021).
Tamura et al., "Structural Correlates of an Anticarcinoma Antibody: Identification of Specificity-Determining Residues Antibody Variant by Retention of (SDRs) and Development of a Minimally Immunogenic Antibody Variant by Retention of SDRs Only," J. Immunol., vol. 164, No. 3, pp. 1432-1441, Feb. 2000.

* cited by examiner

BISPECIFIC ANTI-HUMAN CD20/HUMAN TRANSFERRIN RECEPTOR ANTIBODIES AND METHODS OF USE

CROSS REFERENCE TO RELATED APPLICATIONS

This application is a continuation of International Patent Application No. PCT/EP2016/073413, filed Sep. 30, 2016, published as WO 2017/055542, which claims priority to European Patent Application No. 15188067.1, filed Oct. 2, 2015, the disclosures of which are incorporated herein by reference in their entirety.

SEQUENCE LISTING

The present application contains a Sequence Listing which has been submitted in ASCII format via EFS-Web and is hereby incorporated by reference in its entirety. Said ASCII copy, created on Mar. 28, 2018, is named P33110-US_ST25.txt and is 64,689 bytes in size.

FIELD OF THE INVENTION

The present invention relates to bispecific antibodies against human CD20 and human transferrin receptor, methods for their production, pharmaceutical compositions containing these antibodies, and uses thereof.

BACKGROUND

Lymphocytes are one of several populations of white blood cells. They specifically recognize and respond to foreign antigen. The three major classes of lymphocytes are B lymphocytes (B-cells), T lymphocytes (T-cells) and natural killer (NK) cells. B lymphocytes are the cells responsible for antibody production and provide humoral immunity. B-cells mature within the bone marrow and leave the marrow expressing an antigen-binding antibody on their cell surface. When a naive B-cell first encounters the antigen for which its membrane-bound antibody is specific, the cell begins to divide rapidly and its progeny differentiate into memory B-cells and effector cells called "plasma cells". Memory B-cells have a longer life span and continue to express membrane-bound antibody with the same specificity as the original parent cell. Plasma cells do not produce membrane-bound antibody but instead produce secreted form of the antibody. Secreted antibodies are the major effector molecules of humoral immunity.

The CD20 antigen (also called human B-lymphocyte-restricted differentiation antigen, Bp35) is a hydrophobic transmembrane protein with a molecular weight of approximately 35 kDa located on pre-B and mature B lymphocytes (Valentine et al., J. Biol. Chem. 264 (1989) 11282-11287; and Einfeld et al., EMBO J. 7 (1988) 711-717). The antigen is also expressed on greater than 90% of B-cell non-Hodgkin's lymphomas (NHL) (Anderson et al., Blood 63 (1984) 1424-1433), but is not found on hematopoietic stem cells, pro-B-cells, normal plasma cells or other normal tissues (Tedder et al., J. Immunol. 135 (1985) 973-979). CD20 is thought to regulate an early step(s) in the activation process for cell cycle initiation and differentiation (Tedder et al., supra) and possibly functions as a calcium ion channel (Tedder et al., J. Cell. Biochem. 14D (1990) 195).

Given the expression of CD20 in B-cell lymphomas, this antigen has been a useful therapeutic target to treat such lymphomas. Given the expression of CD20 in B-cell lymphomas, this antigen can serve as a candidate for "targeting" of such lymphomas. In essence, such targeting can be generalized as follows: antibodies specific to the CD20 surface antigen of B-cells are administered to a patient. These anti-CD20 antibodies specifically bind to the CD20 antigen of (ostensibly) both normal and malignant B-cells; the antibody bound to the CD20 surface antigen may lead to the destruction and depletion of neoplastic B-cells. Additionally, chemical agents or radioactive labels having the potential to destroy the tumor can be conjugated to the anti-CD20 antibody such that the agent is specifically "delivered" to the neoplastic B-cells. Irrespective of the approach, a primary goal is to destroy the tumor; the specific approach can be determined by the particular anti-CD20 antibody which is utilized and, thus, the available approaches to targeting the CD20 antigen can vary considerably. For example, the rituximab (RITUXAN®) antibody which is a genetically engineered chimeric murine/human monoclonal antibody directed against human CD20 antigen (commercially available from Genentech, Inc., South San Francisco, Calif., USA) is used for the treatment of patients with relapsed or refractory low-grade or follicular, CD20 positive, B-cell non-Hodgkin's lymphoma. Rituximab is the antibody referred to as "C2B8" in U.S. Pat. No. 5,736,137 and in U.S. Pat. No. 5,776,456. In vitro mechanism of action studies have demonstrated that RITUXAN® binds human complement and lyses lymphoid B-cell lines through complement-dependent cytotoxicity (CDC) (Reff et al., Blood 83 (1994) 435-445). Additionally, it has significant activity in assays for antibody-dependent cellular cytotoxicity (ADCC). In vivo preclinical studies have shown that RITUXAN® depletes B-cells from the peripheral blood, lymph nodes, and bone marrow of cynomolgus monkeys, presumably through complement and cell-mediated processes (Reff et al., Blood 83 (1994) 435-445). Other anti-CD20 antibodies indicated for the treatment of NHL include the murine antibody Zevalin™ which is linked to the radioisotope, Yttrium-90 (IDEC Pharmaceuticals, San Diego, Calif., USA), Bexxar™ which is a another fully murine antibody conjugated to I-131 (Corixa, WA, USA).

CD20 is also a useful target antigen for treating autoimmune diseases. Rituximab has also been studied in a variety of non-malignant autoimmune disorders, in which B-cells and autoantibodies appear to play a role in disease pathophysiology (see e.g. Edwards et al., Biochem. Soc. Trans. 30 (2002) 824-828). Rituximab has been reported to potentially relieve signs and symptoms of, for example, rheumatoid arthritis (RA) (Leandro et al., Ann. Rheum. Dis. 61 (2002) 883-888; Edwards et al., Arthritis Rheum. 46 (Suppl. 9) (2002) S46; Stahl et al., Ann. Rheum. Dis. 62 (Suppl. 1) (2003) OP004; Emery et al., Arthritis Rheum. 48 (2003) S439), lupus (Eisenberg, Arthritis. Res. Ther. 5 (2003) 157-159; Leandro et al., Arthritis Rheum. 46 (2002) 2673-2677; Gorman et al., Lupus, 13 (2004) 312-316), immune thrombocytopenic purpura (D'Arena et al., Leuk. Lymphoma 44 (2003) 561-562; Stasi et al., Blood 98 (2001) 952-957; Saleh et al., Semin. Oncol. 27 (Suppl. 12) (2000) 99-103; Zaia et al., Haematologica 87 (2002) 189-195; Ratanatharathorn et al., Ann. Int. Med. 133 (2000) 275-279), pure red cell aplasia (Auner et al., Br. J. Hematol. 116 (2002) 725-728); autoimmune anemia (Zaja et al., Haematologica 87 (2002) 189-195 (erratum appears in Haematologica 87 (2002) 336), cold agglutinin disease (Layios et al., Leukemia 15 (2001) 187-188; Berentsen et al., Blood 103 (2004) 2925-2928; Berentsen et al., Br. J. Hematol. 115 (2001) 79-83; Bauduer, Br. J. Hematol. 112 (2001) 1083-1090; Damiani et al., Br. J. Hematol. 114 (2001) 229-234), type B syndrome of severe insulin resistance (Coll et al., N. Engl. J. Med. 350 (2004) 310-311, mixed cryoglobulinemia (De Vita et al., Arthritis Rheum. 46 Suppl. 9 (2002) S206/S469), myasthenia gravis (Zaja et al., Neurology 55 (2000) 1062-1063; Wylam et al., J. Pediatr. 143 (2003) 674-677), Wegener's granulomatosis (Specks et al., Arthritis & Rheumatism 44 (2001) 2836-2840), refractory pemphigus vulgaris (Dupuy et al., Arch. Dermatol. 140 (2004) 91-96), dermatomyositis (Levine, Arthritis Rheum. 46 (Suppl. 9) (2002) S1299), Sjogren's syndrome (Somer et al., Arthritis & Rheumatism 49 (2003) 394-398), active type-II mixed cryoglobulinemia (Zaja et al., Blood 101 (2003) 3827-3834), pemphigus vulgaris (Dupay et al., Arch. Dermatol. 140 (2004) 91-95), autoimmune neuropathy (Pestronk et al., J. Neurol. Neurosurg. Psychiatry 74 (2003) 485-489), paraneoplastic opsoclonus-myoclonus syndrome (Pranzatelli et al. Neurology 60 (Suppl. 1) (2003) PO5.128:A395), and relapsing-remitting multiple sclerosis (RRMS) (Cross et al. (abstract) "Preliminary results from a phase II trial of Rituximab in MS" Eighth Annual Meeting of the Americas Committees for Research and Treatment in Multiple Sclerosis, (2003) 20-21).

Publications concerning therapy with rituximab include: Perotta and Abuel, Blood 10 (1998) (part 1-2) 88B; Perotta et al., Blood 94 (1999) 49 (abstract); Matthews, R., Ann. Rheum. Di's, supra; Leandro et al., Arthritis and Rheumatism 44(9): S370 (2001); Leandro et al., Arthritis and Rheumatism 46 (2002) 2673-2677; Weide et al., Lupus 12 (2003) 779-782; Edwards and Cambridge, Rheumatology 40 (2001) 205-211; Cambridge et al., Arthritis Rheum. 46 (Suppl. 9) (2002) S1350; Edwards et al., Arthritis and Rheumatism 46 (2002) S197; Levine and Pestronk, Neurology 52 (1999) 1701-1704; De Vita et al., Arthritis & Rheum. 46 (2002) 2029-2033; Hidashida et al., Annual Scientific Meeting of the American College of Rheumatology; October 24-29; New Orleans, La. 2002; Tuscano, J., Annual Scientific Meeting of the American College of Rheumatology; October 24-29; New Orleans, La. 2002; Martin and Chan, Immunity 20 (2004) 517-527; Silverman and Weisman, Arthritis and Rheumatism 48 (2003) 1484-1492; Kazkaz and Isenberg, Current opinion in pharmacology 4 (2004) 398-402; Virgolini and Vanda, Biomedicine & pharmacotherapy 58 (2004) 299-309; Klemmer et al., Arthritis and Rheumatism 48 (2003) 9,S (SEP) S624-S624; Kneitz et al., Immunobiology 206 (2002) 519-527; Arzoo et al., Annals of the Rheumatic Diseases 61 (2002) p 922-924; Comment in Ann. Rheum. Dis. 61 (2002) 863-866; "Future Strategies in Immunotherapy" by Lake and Dionne, in Burger's Medicinal Chemistry and Drug Discovery (2003 by John Wiley & Sons, Inc.); Liang and Tedder, Wiley Encyclopedia of Molecular Medicine, Section: CD20 as an Immunotherapy Target, 2002 entitled "CD20"; Appendix 4A entitled "Monoclonal Antibodies to Human Cell Surface Antigens" by Stockinger et al., Eds: Coligan et al., in Current Protocols in Immunology (2003 John Wiley & Sons, Inc.); Penichet and Morrison, "CD Antibodies/molecules: Definition; Antibody Engineering" in Wiley Encyclopedia of Molecular Medicine Section: Chimeric, Humanized and Human Antibodies; posted online 15 Jan. 2002; Specks et al., Arthritis & Rheumatism 44 (2001) 2836-2840; Koegh et al., "Rituximab for Remission Induction in Severe ANCA-Associated Vasculitis: Report of a Prospective Open-Label Pilot Trial in 10 Patients", American College of Rheumatology, Session Number: 28-100, Session Title: Vasculitis, Session Type: ACR Concurrent Session, Primary Category: 28 Vasculitis, Session Oct. 18, 2004 (http://www.abstractsonline.com/viewer/SearchResults.asp); Eriksson, Kidney and Blood Pressure Research 26 (2003) 294; Jayne et al., Kidney and Blood Pressure Research, 26 (2003) 294; Jayne, poster 88 (11th International Vasculitis and ANCA workshop), 2003 American Society of Nephrology; Stone and Specks in the Clinical Trial Research Summary of the 2002-2003 Immune Tolerance Network, http://www.immunetolerance.org/reseaTcIT/autoimmune/trial s/stone.html; Leandro et at, Arthritis Rheum. 48 (Suppl. 9) (2003) Sl 160.

Patents and patent publications concerning CD20 antibodies include U.S. Pat. Nos. 5,776,456, 5,736,137, 5,843,439, 6,399,061, 6,682,734, US 2002/0197255 A1, US 2003/0021781 A1, US 2003/0082172 A1, US 2003/0095963 A1, US 2003/0147885 A1; U.S. Pat. No. 6,455,043; WO 00/09160; WO 00/27428; WO 00/27433; WO 00/44788; WO 01/10462; WO 01/10461; WO 01/10460; US 2001/0018041 A1, US 2003/0180292 A1, WO 01/34194; US 2002/0006404; WO 02/04021; US 2002/0012665 A1; WO 01/74388; US 2002/0058029 A1; US 2003/0103971 A1; US 2002/0009444 A1; WO 01/80884; WO 01/97858; US 2002/0128488 A1; WO 02/34790; WO 02/060955; WO 02/096948; WO 02/079255; U.S. Pat. No. 6,171,586 B1; WO 98/56418; WO 98/58964; WO 99/22764; WO 99/51642; U.S. Pat. No. 6,194,551 B1; U.S. Pat. No. 6,242,195 B1; U.S. Pat. No. 6,528,624 B1; U.S. Pat. No. 6,538,124; WO 00/42072; WO 00/67796; WO 01/03734; US 2002/0004587 A1; WO01/77342; US 2002/0197256; US 2003/0157108 A1; U.S. Pat. No. 6,565,827 B1; U.S. Pat. No. 6,090,365 B1; U.S. Pat. No. 6,287,537 B1; U.S. Pat. Nos. 6,015,542; 5,843,398; 5,595,721; 5,500,362; 5,677,180; 5,721,108; 6,120,767; 6,652,852 B1; U.S. Pat. No. 6,410,391 B1; U.S. Pat. No. 6,224,866 B1; WO 00/20864; WO 01/13945; WO 00/67795; US 2003/0133930 A1; WO 00/74718; WO 00/76542; WO 01/72333; U.S. Pat. No. 6,368,596 B1; U.S. Pat. No. 6,306,393; US 2002/0041847 A1; US 2003/0026801 A1; WO 02/102312; US 2003/0068664; WO 03/002607; WO 03/049694; US 2002/0009427 A1; US 2003/0185796 A1; WO 03/061694; US 2003/0219818 A1; US 2003/0219433 A1; WO 03/068821; US 2002/0136719 A1; WO 2004/032828; WO 2004/035607; US 2004/0093621; U.S. Pat. No. 5,849,898; EP 0,330,191; U.S. Pat. No. 4,861,579; EP 0,332,865; WO 95/03770; US 2001/0056066; WO 2004/035607; WO 2004/056312; US 2004/0093621; WO 2004/103404. Publications concerning CD20 antibody include: Teeling, J., et al., Blood 10 (2004) 1182.

WO 2014/033074 relates to blood brain barrier shuttles that bind receptors on the blood brain barrier and methods of using the same. Low affinity blood brain barrier receptor antibodies and uses therefor are reported in WO 2012/075037. WO 2014/189973 relates to anti-transferrin receptor antibodies and methods of their use. A blood brain barrier shuttle module comprising a brain effector entity, a linker and one monovalent binding entity which binds to a blood brain barrier receptor was reported in WO 2015/101588. WO 2010/033587 concerns methods for treating progressive multiple sclerosis in a patient, and an article of manufacture with instructions for such use. A method of treating, arresting or preventing a disease responsive to treatment with an anti-CD20 antibody in a patient suffering therefrom, comprising administering to the patient at least one sub-depleting dose of antiCD20 antibody was reported in WO 2012/096924. Hawker, K., et al. (Ann. Neurol. 66 (2009) 460-471) reported about the results of a randomized double-blind placebo-controlled multicenter trial of Rituximab in patients with primary progressive multiple sclerosis.

SUMMARY

One aspect as reported herein is a bispecific antibody comprising a) one (full length) antibody comprising two pairs each of a (full length) antibody light chain and a (full length) antibody heavy chain, wherein the binding sites formed by each of the pairs of the (full length) heavy chain and the (full length) light chain specifically bind to a first antigen, and b) one additional Fab fragment, wherein the additional Fab fragment is fused to any C-terminus of one heavy chain of the (full length) antibody, wherein the binding site of the additional Fab fragment specifically binds to a second antigen, wherein each of the (full length) antibody light chains comprises in the constant light chain domain (CL) at position 123 the amino acid residue arginine (instead of the wild-type glutamic acid residue; E123R mutation) and at position 124 the amino acid residue lysine (instead of the wild-type glutamine residue; Q124K mutation) (numbering according to Kabat), wherein each of the (full length) antibody heavy chains comprises in the first constant heavy chain domain (CH1) at position 147 an glutamic acid residue (instead of the wild-type lysine residue; K147E mutation) and at position 213 an glutamic acid residue (instead of the wild-type lysine amino acid residue; K213E mutation) (numbering according to Kabat EU index), wherein the additional Fab fragment specifically binding to the second antigen comprises a domain crossover such that the constant light chain domain (CL) and the constant heavy chain domain 1 (CH1) are replaced by each other, and wherein the first antigen is human CD20 and the second antigen is human transferrin receptor.

In one embodiment the additional Fab fragment is fused to the C-terminus of the heavy chain by a peptidic linker.

In one embodiment the N-terminus of the heavy chain variable domain of the Fab fragment is fused to the C-terminus of the (full length) heavy chain or the C-terminus of the peptidic linker.

In one embodiment a) the (full length) heavy chain that is fused to the additional Fab fragments has as C-terminal (heavy chain) amino acid residues the tripeptide LSP wherein the proline thereof is directly fused to the first amino acid residue of the additional Fab fragment or of the peptidic linker via a peptide bond, and b) the (full length) heavy chain that is not fused to the additional Fab fragments has as C-terminal (heavy chain) amino acid residues the tripeptide LSP, or SPG, or PGK.

In one embodiment the (full length) antibody is a) a full length antibody of the human subclass IgG1,
b) a full length antibody of the human subclass IgG4,
c) a full length antibody of the human subclass IgG1 with the mutations L234A, L235A and P329G,
d) a full length antibody of the human subclass IgG4 with the mutations S228P, L235E and P329G,
e) a full length antibody of the human subclass IgG1 with the mutations L234A, L235A and P329G in both heavy chains and the mutations i) T366W, and ii) S354C or Y349C, in one heavy chain and the mutations i) T366S, L368A, and Y407V, and ii) Y349C or S354C, in the respective other heavy chain, f) a full length antibody of the human subclass IgG4 with the mutations S228P, L235E and P329G in both heavy chains and the mutations i) T366W, and ii) S354C or Y349C, in one heavy chain and the mutations i) T366S, L368A, and Y407V, and ii) Y349C or S354C, in the respective other heavy chain, g) a full length antibody of the human subclass IgG1 with the mutations L234A, L235A, P329G, I253A, H310A and H435A in both heavy chains and the mutations i) T366W, and ii) S354C or Y349C, in one heavy chain and the mutations i) T366S, L368A, and Y407V, and ii) Y349C or S354C, in the respective other heavy chain, or h) a full length antibody of the human subclass IgG1 with the mutations L234A, L235A, P329G, M252Y, S254T and T256E in both heavy chains and the mutations i) T366W, and ii) S354C or Y349C, in one heavy chain and the mutations i) T366S, L368A, and Y407V, and ii) Y349C or S354C, in the respective other heavy chain, or i) a full length antibody of the human subclass IgG1 with the mutations L234A, L235A, P329G, H310A, H433A and Y436A in both heavy chains and the mutations i) T366W, and ii) S354C or Y349C, in one heavy chain and the mutations i) T366S, L368A, and Y407V, and ii) Y349C or S354C, in the respective other heavy chain.

In one embodiment the additional Fab fragment is fused to the C-terminus of the heavy chain comprising the mutation T366W, or to the C-terminus of the heavy chain comprising the mutations T366S, L368A, and Y407V.

In one embodiment the (full length) antibody is of the human subclass IgG1 with the mutations L234A, L235A and P329G in both heavy chains and the mutations T366W and S354C in one heavy chain and the mutations T366S, L368A, Y407V and Y349C in the respective other heavy chain, and the additional Fab fragment is fused to the C-terminus of the heavy chain comprising the mutation T366W, or to the C-terminus of the heavy chain comprising the mutations T366S, L368A, and Y407V.

In one embodiment the bispecific antibody comprises i) a light chain that has a sequence identity to SEQ ID NO: 01 of 70% or more,
ii) a heavy chain that has a sequence identity to SEQ ID NO: 02 of 70% or more,
iii) a light chain that has a sequence identity to SEQ ID NO: 03 of 70% or more, and
iv) a heavy chain Fab fragment that has a sequence identity to SEQ ID NO: 04 of 70% or more, wherein SEQ ID NO: 01 has the amino acid sequence
DIVMTQTPLSLPVTPGEPASISCRSSKSLLHSNGITYLYWYLQKPGQSP

QLLIYQMSNLVSGVPDRFSGSGSGTDFTLKISRVEAEDVGVYYCAQNLE

LPYTFGGGTKVEIKRTVAAPSVFIFPPSDRKLKSGTASVVCLLNNFYPR

EAKVQWKVDNALQSGNSQESVTEQDSKDSTYSLSSTLTLSKADYEKHKV

YACEVTHQGLSSPVTKSFNRGEC,

SEQ ID NO: 02 has the amino acid sequence
QVQLVQSGAEVKKPGSSVKVSCKASGYAFSYSWINWVRQAPGQGLEWMG

RIFPGDGDTDYNGKFKGRVTITADKSTSTAYMELSSLRSEDTAVYYCAR

-continued
NVFDGYWLVYWGQGTLVTVSSASTKGPSVFPLAPSSKSTSGGTAALGCL

VEDYFPEPVTVSWNSGALTSGVHTFPAVLQSSGLYSLSSVVTVPSSSLG

TQTYICNVNHKPSNTKVDEKVEPKSCDKTHTCPPCPAPEAAGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALGAPIEKTISKAKG

QPREPQVCTLPPSRDELTKNQVSLSCAVKGFYPSDIAVEWESNGQPENN

YKTTPPVLDSDGSFFLVSKLTVDKSRWQQGNVFSCSVMHEALHNHYTQK

SLSLSPG,

SEQ ID NO: 03 has the amino acid sequence
AIQLTQSPSSLSASVGDRVTITCRASQSISSYLAWYQQKPGKAPKLLIY

RASTLASGVPSRFSGSGSGTDFTLTISSLQPEDFATYYCQQNYASSNVD

NTFGGGTKVEIKSSASTKGPSVFPLAPSSKSTSGGTAALGCLVKDYFPE

PVTVSWNSGALTSGVHTFPAVLQSSGLYSLSSVVTVPSSSLGTQTYICN

VNHKPSNTKVDKKVEPKSC,
and

SEQ ID NO: 04 has the amino acid sequence
QSMQESGPGLVKPSQTLSLTCTVSGFSLSSYAMSWIRQHPGKGLEWIGY

IWSGGSTDYASWAKSRVTISKTSTTVSLKLSSVTAADTAVYYCARRYGT

SYPDYGDASGFDPWGQGTLVTVSSASVAAPSVFIFPPSDEQLKSGTASV

VCLLNNFYPREAKVQWKVDNALQSGNSQESVTEQDSKDSTYSLSSTLTL

SKADYEKHKVYACEVTHQGLSSPVTKSFNRGEC.

One aspect as reported herein is a bispecific antibody comprising a (full length) light chain that has the amino acid sequence of SEQ ID NO: 01, a (full length) heavy chain that has the amino acid sequence of SEQ ID NO: 02, a (full length) light chain that has the amino acid sequence of SEQ ID NO: 03, and an antibody Fab fragment comprising the amino acid sequences of SEQ ID NO: 04.

In one embodiment the bispecific antibody is monoclonal.

One aspect as reported herein is a bispecific antibody comprising
a) a first and a second Fab fragment, wherein each binding site of the first and the second Fab fragment specifically bind to a first antigen,
b) a third Fab fragment, wherein the binding site of the third Fab fragment specifically binds to a second antigen, and wherein the third Fab fragment comprises a domain crossover such that the variable light chain domain (VL) and the variable heavy chain domain (VH) are replaced by each other, and
c) an Fc-region comprising a first Fc-region polypeptide and a second Fc-region polypeptide,
wherein the first and the second Fab fragment each comprise a heavy chain fragment and a full length light chain,
wherein the C-terminus of the heavy chain fragment of the first Fab fragment is fused to the N-terminus of the first Fc-region polypeptide,
wherein the C-terminus of the heavy chain fragment of the second Fab fragment is fused to the N-terminus of the variable light chain domain of the third Fab fragment and the C-terminus of the heavy chain constant domain 1 of the third Fab fragment is fused to the N-terminus of the second Fc-region polypeptide,
wherein each of the full length light antibody chains of the first and second Fab fragment comprises in the constant light chain domain (CL) at position 123 the amino acid residue arginine (instead of the wild-type glutamic acid residue; E123R mutation) and at position 124 the amino acid residue lysine (instead of the wild-type glutamine residue; Q124K mutation) (numbering according to Kabat),
wherein each of the heavy chain fragments of the first and second Fab fragment comprises in the first constant heavy chain domain (CH1) at position 147 an glutamic acid residue (instead of the wild-type lysine residue; K147E mutation) and at position 213 an glutamic acid residue (instead of the wild-type lysine amino acid residue; K213E mutation) (numbering according to Kabat EU index),
wherein the first antigen is human CD20 and the second antigen is human transferrin receptor.

In one embodiment the first and the second Fc-region polypeptide is
a) of the human subclass IgG1,
b) of the human subclass IgG4,
c) of the human subclass IgG1 with the mutations L234A, L235A and P329G,
d) of the human subclass IgG4 with the mutations S228P, L235E and P329G,
e) of the human subclass IgG1 with the mutations L234A, L235A and P329G in both Fc-region polypeptides and the mutations T366W and S354C in one Fc-region polypeptide and the mutations T366S, L368A, Y407V and Y349C in the respective other Fc-region polypeptide,
f) of the human subclass IgG4 with the mutations S228P, L235E and P329G in both Fc-region polypeptides and the mutations T366W and S354C in one Fc-region polypeptide and the mutations T366S, L368A, Y407V and Y349C in the respective other Fc-region polypeptide,
g) of the human subclass IgG1 with the mutations L234A, L235A, P329G, I253A, H310A and H435A in both Fc-region polypeptides and the mutations T366W and S354C in one Fc-region polypeptide and the mutations T366S, L368A, Y407V and Y349C in the respective other Fc-region polypeptide, or
h) of the human subclass IgG1 with the mutations L234A, L235A, P329G, M252Y, S254T and T256E in both Fc-region polypeptides and the mutations T366W and S354C in one Fc-region polypeptide and the mutations T366S, L368A, Y407V and Y349C in the respective other Fc-region polypeptide, or
i) of the human subclass IgG1 with the mutations L234A, L235A, P329G, H310A, H433A and Y436A in both Fc-region polypeptides and the mutations T366W and S354C in one Fc-region polypeptide and the mutations T366S, L368A, Y407V and Y349C in the respective other Fc-region polypeptide.

In one embodiment one of the chains of the third Fab fragment is fused to the Fc-region polypeptide comprising the mutation T366W, or to the Fc-region polypeptide comprising the mutations T366S, L368A, and Y407V.

In one embodiment the bispecific antibody comprises
i) a light chain that has a sequence identity to SEQ ID NO: 14 of at least 70%, or at least 80%, or at least 90%, or 95% or more,
ii) a heavy chain that has a sequence identity to SEQ ID NO: 15 of at least 70%, or at least 80%, or at least 90%, or 95% or more, iii) a crossed antibody chain that has a sequence identity to SEQ ID NO: 16 of at least 70%, or at least 80%, or at least 90%, or 95% or more, and iv) a modified heavy chain that has a sequence identity to SEQ ID NO: 17 of at least 70%, or at least 80%, or at least 90%, or 95% or more, wherein SEQ ID NO: 14 has the amino acid sequence
DIVMTQTPLSLPVTPGEPASISCRSSKSLLHSNGITYLYWYLQKPGQS

PQLLIYQMSNLVSGVPDRFSGSGSGTDFTLKISRVEAEDVGVYYCAQN

LELPYTFGGGTKVEIKRTVAAPSVFIFPPSDRKLKSGTASVVCLLNNF

YPREAKVQWKVDNALQSGNSQESVTEQDSKDSTYSLSSTLTLSKADYE

KHKVYACEVTHQGLSSPVTKSFNRGEC,

SEQ ID NO: 15 has the amino acid sequence
QVQLVQSGAEVKKPGSSVKVSCKASGYAFSYSWINWVRQAPGQGLEWM

GRIFPGDGDTDYNGKFKGRVTITADKSTSTAYMELSSLRSEDTAVYYC

ARNVFDGYWLVYWGQGTLVTVSSASTKGPSVFPLAPSSKSTSGGTAAL

GCLVEDYFPEPVTVSWNSGALTSGVHTFPAVLQSSGLYSLSSVVTVPS

SSLGTQTYICNVNHKPSNTKVDEKVEPKSCDKTHTCPPCPAPEAAGGP

SVFLFPPKPKDTLMISRTPEVTCVVVDVSHEDPEVKFNWYVDGVEVHN

AKTKPREEQYNSTYRVVSVLTVLHQDWLNGKEYKCKVSNKALGAPIEK

TISKAKGQPREPQVCTLPPSRDELTKNQVSLSCAVKGFYPSDIAVEWE

SNGQPENNYKTTPPVLDSDGSFFLVSKLTVDKSRWQQGNVFSCSVMHE

ALHNHYTQKSLSLSPG,

SEQ ID NO: 16 has the amino acid sequence
QSMQESGPGLVKPSQTLSLTCTVSGFSLSSYAMSWIRQHPGKGLEWIG

YIWSGGSTDYASWAKSRVTISKTSTTVSLKLSSVTAADTAVYYCARRY

GTSYPDYGDASGFDPWGQGTLVTVSSASVAAPSVFIFPPSDEQLKSGT

ASVVCLLNNFYPREAKVQWKVDNALQSGNSQESVTEQDSKDSTYSLSS

TLTLSKADYEKHKVYACEVTHQGLSSPVTKSFNRGEC, and

SEQ ID NO: 17 has the amino acid sequence
QVQLVQSGAEVKKPGSSVKVSCKASGYAFSYSWINWVRQAPGQGLEWM

GRIFPGDGDTDYNGKFKGRVTITADKSTSTAYMELSSLRSEDTAVYYC

ARNVFDGYWLVYWGQGTLVTVSSASTKGPSVFPLAPSSKSTSGGTAAL

GCLVEDYFPEPVTVSWNSGALTSGVHTFPAVLQSSGLYSLSSVVTVPS

SSLGTQTYICNVNHKPSNTKVDEKVEPKSCDGGGSGGGGSAIQLTQS

PSSLSASVGDRVTITCRASQSISSYLAWYQQKPGKAPKLLIYRASTLA

SGVPSRFSGSGSGTDFTLTISSLQPEDFATYYCQQNYASSNVDNTFGG

GTKVEIKSSASTKGPSVFPLAPSSKSTSGGTAALGCLVKDYFPEPVTV

SWNSGALTSGVHTFPAVLQSSGLYSLSSVVTVPSSSLGTQTYICNVNH

KPSNTKVDKKVEPKSCDKTHTCPPCPAPEAAGGPSVFLFPPKPKDTLM

ISRTPEVTCVVVDVSHEDPEVKFNWYVDGVEVHNAKTKPREEQYNSTY

RVVSVLTVLHQDWLNGKEYKCKVSNKALGAPIEKTISKAKGQPREPQV

YTLPPCRDELTKNQVSLWCLVKGFYPSDIAVEWESNGQPENNYKTTPP

VLDSDGSFFLYSKLTVDKSRWQQGNVFSCSVMHEALHNHYTQKSLSLS

PG.

One aspect as reported herein is a bispecific antibody comprising two full length light chains that each has the amino acid sequence of SEQ ID NO: 14, a full length heavy chain that has the amino acid sequence of SEQ ID NO: 15, a crossed antibody chain that has the amino acid sequence of SEQ ID NO: 16, and a modified heavy chain that has the amino acid sequence of SEQ ID NO: 17.

In one embodiment the bispecific antibody is monoclonal.

One aspect as reported herein is an isolated nucleic acid encoding the bispecific antibody as reported herein.

One aspect as reported herein is a host cell comprising the nucleic acid as reported herein encoding the bispecific antibody as reported herein.

One aspect as reported herein is a method of producing a bispecific antibody as reported herein comprising the following steps:
a) culturing the host cell as reported herein so that the bispecific antibody is produced, and
b) recovering the bispecific antibody from the cell or the cultivation medium and thereby producing the bispecific antibody as reported herein.

One aspect as reported herein is an immunoconjugate comprising the bispecific antibody as reported herein and a cytotoxic agent.

One aspect as reported herein is a pharmaceutical formulation comprising the bispecific antibody as reported herein and a pharmaceutically acceptable carrier.

One aspect as reported herein is the antibody as reported herein for use as a medicament.

One aspect as reported herein is the antibody as reported herein for the treatment of cancer.

One aspect as reported herein is the bispecific antibody as reported herein for use in treating B-cell proliferative disease.

One aspect as reported herein is the bispecific antibody as reported herein for use in inhibiting growth of tumor cells expressing CD20. In one embodiment the inhibiting is in the brain.

One aspect as reported herein is the bispecific antibody as reported herein for use in treating carcinoma. In one preferred embodiment the carcinoma is carcinoma of/in the brain.

One aspect as reported herein is the bispecific antibody as reported herein for use in treating lymphoma. In one preferred embodiment the lymphoma is primary central nervous system lymphoma (PCNSL).

One aspect as reported herein is the bispecific antibody as reported herein for use in treating an autoimmune disease. In one embodiment the autoimmune disease is multiple sclerosis. In one preferred embodiment the autoimmune disease is secondary progressive multiple sclerosis.

One aspect as reported herein is the bispecific antibody as reported herein for use in depleting tumor cells expressing CD20. In one embodiment the depleting is in the brain.

One aspect as reported herein is the bispecific antibody as reported herein for use in depleting circulating B-cells expressing CD20. In one embodiment the depleting is in the brain.

One aspect as reported herein is the bispecific antibody as reported herein for use in depleting brain sequestered B-cells expressing CD20.

One aspect as reported herein is the use of the bispecific antibody as reported herein in the manufacture of a medicament.

In one embodiment the medicament is for the treatment of a proliferative type disease. In one embodiment the proliferative type disease is a B-cell proliferative disease. In one embodiment the proliferative type disease is B-cell lymphoma. In one preferred embodiment the proliferative type disease is primary central nervous system lymphoma.

In one embodiment the medicament is for the treatment of a tumor.

In one embodiment the medicament is for the treatment of human carcinoma.

In one embodiment the medicament is for the treatment of an autoimmune disease.

In one embodiment the autoimmune disease is selected from the group consisting of inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T-cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitus); multiple sclerosis; Reynaud's syndrome; autoimmune thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; anti-phospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Bechet disease; giant cell arteritis; immune complex nephritis; IgA nephropathy; IgM polyneuropathies; immune thrombocytopenic purpura (ITP) or autoimmune thrombocytopenia. In one embodiment the medicament is for treatment of multiple sclerosis. In one preferred embodiment the medicament is for the treatment of secondary progressive multiple sclerosis.

In one embodiment the medicament is for depleting tumor cells expressing CD20.

In one embodiment the depleting is in the brain.

In one embodiment the medicament is for depleting circulating B-cells expressing CD20. In one embodiment the depleting is in the brain.

In one embodiment the medicament is for depleting brain sequestered B-cells expressing CD20.

One aspect as reported herein is a method of treating an individual having a proliferative type disease comprising administering to the individual an effective amount of the bispecific antibody as reported herein. In one embodiment the proliferative type disease is a B-cell proliferative disease.

One aspect as reported herein is a method of treating an individual having carcinoma comprising administering to the individual an effective amount of the bispecific antibody as reported herein. In one preferred embodiment the carcinoma is carcinoma of/in the brain.

One aspect as reported herein is a method of treating an individual having lymphoma comprising administering to the individual an effective amount of the bispecific antibody as reported herein. In one preferred embodiment the lymphoma is primary central nervous system lymphoma (PCNSL).

One aspect as reported herein is a method of treating an individual having an autoimmune disease comprising administering to the individual an effective amount of the bispecific antibody as reported herein. In one embodiment the autoimmune disease is multiple sclerosis. In one preferred embodiment the autoimmune disease is secondary progressive multiple sclerosis.

One aspect as reported herein is a method for inhibiting growth of tumor cells expressing CD20 in an individual comprising administering to the individual an effective amount of the bispecific antibody as reported herein to inhibit growth of tumor cells expressing CD20. In one embodiment the inhibiting is in the brain.

One aspect as reported herein is a method for depleting tumor cells expressing CD20 in an individual comprising administering to the individual an effective amount of the bispecific antibody as reported herein to deplete tumor cells expressing CD20. In one embodiment the inhibiting is in the brain.

One aspect as reported herein is a method for depleting circulating B-cells expressing CD20 in an individual comprising administering to the individual an effective amount of the bispecific antibody as reported herein to deplete circulating B-cells expressing CD20. In one embodiment the inhibiting is in the brain.

One aspect as reported herein is a method for depleting brain sequestered B-cells expressing CD20 in an individual comprising administering to the individual an effective amount of the bispecific antibody as reported herein to deplete brain sequestered B-cells expressing CD20.

One aspect as reported herein is a method of treating multiple sclerosis in a human comprising administering to the human a therapeutically effective amount of an antibody as reported herein which binds to human CD20 and depletes B-cells, and wherein the antibody is not conjugated with a cytotoxic agent.

DETAILED DESCRIPTION OF EMBODIMENTS OF THE INVENTION

The knobs into holes dimerization modules and their use in antibody engineering are described in Carter P.; Ridgway J. B. B.; Presta L. G.: Immunotechnology, Volume 2, Number 1, February 1996, pp. 73-73. The additional disulfide bridge in the CH3 domain is reported in Merchant, A. M., et al., Nat. Biotechnol. 16 (1998) 677-681.

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991).

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, Md. (1991) and is referred to as "numbering according to Kabat" herein. Specifically, the Kabat numbering system (see pages 647-660) of Kabat, et al., Sequences of Proteins of Immunological Interest, 5th ed., Public Health Service, National Institutes of Health, Bethesda, Md. (1991) is used for the light chain constant domain CL of kappa and lambda isotype, and the Kabat EU index numbering system (see pages 661-723) is used for the constant heavy chain domains (CH1, Hinge, CH2 and CH3, which is herein further clarified by referring to "numbering according to Kabat EU index" in this case).

I. Definitions

The "blood-brain-barrier" or "BBB" refers to the physiological barrier between the peripheral circulation and the brain and spinal cord which is formed by tight junctions within the brain capillary endothelial plasma membranes, creating a tight barrier that restricts the transport of molecules into the brain, even very small molecules such as urea (60 Daltons). The BBB within the brain, the blood-spinal-cord barrier within the spinal cord, and the blood-retinal-barrier within the retina are contiguous capillary barriers within the CNS, and are herein collectively referred to an the blood-brain-barrier or BBB. The BBB also encompasses the blood-CSF barrier (choroid plexus) where the barrier is comprised of ependymal cells rather than capillary endothelial cells.

The terms "anti-human CD20 antibody" and "an antibody specifically binding to human CD20" refer to an antibody that is capable of binding human CD20 with sufficient affinity such that the antibody is useful as a diagnostic and/or therapeutic agent in targeting CD20.

Thus, the term also encompasses antibodies that bind to a shortened fragment of human CD20.

Examples of antibodies which bind the CD20 antigen include: "C2B8" which is now called "rituximab" ("RITUXAN®") (U.S. Pat. No. 5,736,137); the yttrium-[90]-labeled 2B8 murine antibody designated "Y2B8" (U.S. Pat. No. 5,736,137); murine IgG2a "B1" optionally labeled with 131I to generate the "131I-B1" antibody (BEXXAR™) (U.S. Pat. No. 5,595,721); murine monoclonal antibody "1F5" (Press et al., Blood 69 (1987) 584-591); "chimeric 2H7" antibody (U.S. Pat. No. 5,677,180); monoclonal antibodies L27, G28-2, 93-1B3, B-C1 or NU-B2 available from the International Leukocyte Typing Workshop (Valentine et al., In: Leukocyte Typing III (McMichael, Ed.) p. 440, Oxford University Press (1987)); and the monoclonal antibody described in U.S. Pat. No. 8,883,980.

The "CD20" antigen is an approx. 35 kDa, non-glycosylated phosphoprotein found on the surface of greater than 90% of B-cells from peripheral blood or lymphoid organs. CD20 is expressed during early pre-B-cell development and remains until plasma cell differentiation. CD20 is present on both normal B-cells as well as malignant B-cells. Other names for CD20 in the literature include "B-lymphocyte-restricted antigen" and "Bp35". The CD20 antigen is described in Clark et al. Proc. Natl. Acad. Sci USA 82 (1985) 1766, for example. See also SEQ ID NO: 05.

An "autoimmune disease" herein is a non-malignant disease or disorder arising from and directed against an individual's own tissues. The term "autoimmune diseases" as used herein specifically excludes malignant or cancerous diseases or conditions, especially excluding B-cell lymphoma, acute lymphoblastic leukemia (ALL), chronic lymphocytic leukemia (CLL), Hairy cell leukemia and chronic myeloblastic leukemia. Examples of autoimmune diseases or disorders include, but are not limited to, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T-cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitus); multiple sclerosis; Reynaud's syndrome; autoimmune thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; anti-phospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Bechet disease; giant cell arteritis; immune complex nephritis; IgA nephropathy; IgM polyneuropathies; immune thrombocytopenic purpura (ITP) or autoimmune thrombocytopenia etc.

An "antagonist" is a molecule which, upon binding to a B-cell surface marker, destroys, kills or depletes B-cells in a mammal and/or interferes with one or more B-cell functions, e.g. by reducing or preventing a humoral response elicited by the B-cell. The antagonist is able to deplete B-cells (i.e. reduce circulating B-cell levels) in a mammal treated therewith. Such depletion may be achieved via various mechanisms such antibody-dependent cell-mediated cytotoxicity (ADCC) and/or complement dependent cytotoxicity (CDC), inhibition of B-cell proliferation and/or induction of B-cell death (e.g. via apoptosis). Antagonists include antibodies, synthetic or native sequence peptides and small molecules which bind to the B-cell marker, optionally conjugated with or fused to a cytotoxic agent.

"Growth inhibitory" antagonists are those, which prevent or reduce proliferation of a cell expressing an antigen to which the antagonist binds. For example, the antagonist may prevent or reduce proliferation of B-cells in vitro and/or in vivo.

Antagonists which "induce apoptosis" are those which induce programmed cell death, e.g. of a B-cell, as determined by standard apoptosis assays, such as binding of Annexin V, fragmentation of DNA, cell shrinkage, dilation of endoplasmic reticulum, cell fragmentation, and/or formation of membrane vesicles (called apoptotic bodies).

An antagonist "which binds" an antigen of interest, e.g. a B-cell surface marker, is one capable of binding that antigen with sufficient affinity and/or avidity such that the antagonist is useful as a therapeutic agent for targeting a cell expressing the antigen.

The "central nervous system" or "CNS" refers to the complex of nerve tissues that control bodily function, and includes the brain and spinal cord.

A "blood-brain-barrier receptor" (abbreviated "BBBR" herein) is an extracellular membrane-linked receptor protein expressed on brain endothelial cells which is capable of transporting molecules across the BBB or be used to transport exogenous administrated molecules. Examples of BBBR herein include: transferrin receptor (TfR), insulin receptor, insulin-like growth factor receptor (IGF-R), low density lipoprotein receptors including without limitation low density lipoprotein receptor-related protein 1 (LRP1) and low density lipoprotein receptor-related protein 8 (LRP8), and heparin-binding epidermal growth factor-like growth factor (HB-EGF). One preferred BBBR is transferrin receptor (TfR).

The "transferrin receptor" ("TfR") is a transmembrane glycoprotein (with a molecular weight of about 180,000 Da) composed of two disulphide-bonded sub-units (each of apparent molecular weight of about 90,000 Da) involved in iron uptake in vertebrates. In one embodiment, the TfR as mentioned herein is human TfR comprising the amino acid sequence as in Schneider et al. (Nature 311 (1984) 675-678), for example.

A "multispecific antibody" denotes an antibody having binding specificities for at least two different epitopes on the same antigen or two different antigens. Exemplary multispecific antibodies may bind both a BBBR and a brain antigen. Multispecific antibodies can be prepared as full-length antibodies or antibody fragments (e.g. F(ab')2 bispecific antibodies) or combinations thereof (e.g. full length antibody plus additional scFv or Fab fragments). Engineered antibodies with two, three or more (e.g. four) functional antigen binding sites have also been reported (see, e.g., US 2002/0004587 A1).

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (kd).

Affinity can be measured by common methods known in the art, such as surface plasmon resonance and including those described herein.

An "affinity matured" antibody refers to an antibody with one or more alterations in one or more hypervariable regions (HVRs), compared to a parent antibody which does not possess such alterations, such alterations resulting in an improvement in the affinity of the antibody for its antigen(s).

The term "antibody" herein is used in the broadest sense and encompasses various antibody structures, including but not limited to monoclonal antibodies, polyclonal antibodies, and multispecific antibodies (e.g., bispecific antibodies) so long as they exhibit the desired antigen-binding activity.

The term "antibody-dependent cellular cytotoxicity (ADCC)" is a function mediated by Fc receptor binding and refers to lysis of target cells by an antibody as reported herein in the presence of effector cells. ADCC is measured in one embodiment by the treatment of a preparation of CD19 expressing erythroid cells (e.g. K562 cells expressing recombinant human CD19) with an antibody as reported herein in the presence of effector cells such as freshly isolated PBMC (peripheral blood mononuclear cells) or purified effector cells from buffy coats, like monocytes or NK (natural killer) cells. Target cells are labeled with 51Cr and subsequently incubated with the antibody. The labeled cells are incubated with effector cells and the supernatant is analyzed for released 51Cr. Controls include the incubation of the target endothelial cells with effector cells but without the antibody. The capacity of the antibody to induce the initial steps mediating ADCC is investigated by measuring their binding to Fcγ receptors expressing cells, such as cells, recombinantly expressing FcγRI and/or FcγRIIA or NK cells (expressing essentially FcγRIIIA). In one preferred embodiment binding to FcγR on NK cells is measured.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., At211, I131, I125, Y90, Re186, Re188, Sm153, Bi212, P32, Pb212 and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

The term "complement-dependent cytotoxicity (CDC)" refers to lysis of cells induced by the antibody as reported herein in the presence of complement. CDC is measured in one embodiment by the treatment of CD19 expressing human endothelial cells with an antibody as reported herein in the presence of complement. The cells are in one embodiment labeled with calcein. CDC is found if the antibody induces lysis of 20% or more of the target cells at a concentration of 30 µg/ml. Binding to the complement factor C1q can be measured in an ELISA. In such an assay in principle an ELISA plate is coated with concentration ranges of the antibody, to which purified human C1q or human serum is added. C1q binding is detected by an antibody directed against C1q followed by a peroxidase-labeled conjugate. Detection of binding (maximal binding Bmax) is measured as optical density at 405 nm (OD405) for peroxidase substrate ABTS® (2,2'-azino-di-[3-ethylbenzthiazoline-6-sulfonate (6)]).

"Effector functions" refer to those biological activities attributable to the Fc-region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B-cell receptor); and B-cell activation.

Fc receptor binding dependent effector functions can be mediated by the interaction of the Fc-region of an antibody with Fc receptors (FcRs), which are specialized cell surface receptors on hematopoietic cells. Fc receptors belong to the immunoglobulin superfamily, and have been shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC) (see e.g. Van de Winkel, J. G. and Anderson, C. L., J. Leukoc. Biol. 49 (1991) 511-524). FcRs are defined by their specificity for immunoglobulin isotypes: Fc receptors for IgG antibodies are referred to as FcγR. Fc receptor binding is described e.g. in Ravetch, J. V. and Kinet, J. P., Annu. Rev. Immunol. 9 (1991) 457-492; Capel, P. J., et al., Immunomethods 4 (1994) 25-34; de Haas, M., et al., J. Lab. Clin. Med. 126 (1995) 330-341; and Gessner, J. E., et al., Ann. Hematol. 76 (1998) 231-248.

Cross-linking of receptors for the Fc-region of IgG antibodies (FcγR) triggers a wide variety of effector functions including phagocytosis, antibody-dependent cellular cytotoxicity, and release of inflammatory mediators, as well as immune complex clearance and regulation of antibody production. In humans, three classes of FcγR have been characterized, which are:

FcγRI (CD64) binds monomeric IgG with high affinity and is expressed on macrophages, monocytes, neutrophils and eosinophils. Modification in the Fc-region IgG at least at one of the amino acid residues E233-G236, P238, D265, N297, A327 and P329 (numbering according to EU index of Kabat) reduce binding to FcγRI. IgG2 residues at positions 233-236, substituted into IgG1 and IgG4, reduced binding to FcγRI by $10^3$-fold and eliminated the human monocyte response to antibody-sensitized red blood cells (Armour, K. L., et al., Eur. J. Immunol. 29 (1999) 2613-2624), FcγRII (CD32) binds complexed IgG with medium to low affinity and is widely expressed. This receptor can be divided into two sub-types, FcγRIIA and FcγRIIB. FcγRIIA is found on many cells involved in killing (e.g. macrophages, monocytes, neutrophils) and seems able to activate the killing process. FcγRIIB seems to play a role in inhibitory processes and is found on B-cells, macrophages and on mast cells and eosinophils. On B-cells it seems to function to suppress further immunoglobulin production and isotype switching to, for example, the IgE class. On macrophages, FcγRIIB acts to inhibit phagocytosis as mediated through FcγRIIA. On eosinophils and mast cells the B-form may help to suppress activation of these cells through IgE binding to its separate receptor. Reduced binding for FcγRIIA is found e.g. for antibodies comprising an IgG Fc-region with mutations at least at one of the amino acid residues E233-G236, P238, D265, N297, A327, P329, D270, Q295, A327, R292, and K414 (numbering according to EU index of Kabat), FcγRIII (CD16) binds IgG with medium to low affinity and exists as two types. FcγRIIIA is found on NK cells, macrophages, eosinophils and some monocytes and T cells and mediates ADCC. FcγRIIIB is highly expressed on neutrophils. Reduced binding to FcγRIIIA is found e.g. for antibodies comprising an IgG Fc-region with mutation at least at one of the amino acid residues E233-G236, P238, D265, N297, A327, P329, D270, Q295, A327, S239, E269, E293, Y296, V303, A327, K338 and D376 (numbering according to EU index of Kabat).

Mapping of the binding sites on human IgG1 for Fc receptors, the above mentioned mutation sites and methods for measuring binding to FcγRI and FcγRIIA are described in Shields, R. L., et al., J. Biol. Chem. 276 (2001) 6591-6604.

An "effective amount" of an agent, e.g., a pharmaceutical formulation, refers to an amount effective, at dosages and for periods of time necessary, to achieve the desired therapeutic or prophylactic result.

The term "Fc receptor" as used herein refers to activation receptors characterized by the presence of a cytoplasmatic ITAM sequence associated with the receptor (see e.g. Ravetch, J. V. and Bolland, S., Annu. Rev. Immunol. 19 (2001) 275-290). Such receptors are FcγRI, FcγRIIA and FcγRIIIA. The term "no binding of FcγR" denotes that at an antibody concentration of 10 µg/ml the binding of an antibody as reported herein to NK cells is 10% or less of the binding found for anti-OX40L antibody LC.001 as reported in WO 2006/029879.

While IgG4 shows reduced FcR binding, antibodies of other IgG subclasses show strong binding. However Pro238, Asp265, Asp270, Asn297 (loss of Fc carbohydrate), Pro329 and 234, 235, 236 and 237 Ile253, Ser254, Lys288, Thr307, Gln311, Asn434, and His435 are residues which provide if altered also reduce FcR binding (Shields, R. L., et al., J. Biol. Chem. 276 (2001) 6591-6604; Lund, J., et al., FASEB J. 9 (1995) 115-119; Morgan, A., et al., Immunology 86 (1995) 319-324; and EP 0 307 434). In one embodiment the antibody as reported herein is of IgG1 or IgG2 subclass and comprises the mutation PVA236, GLPSS331, and/or L234A/L235A. In one embodiment the antibody as reported herein is of IgG4 subclass and comprises the mutation L235E. In one embodiment the antibody further comprises the mutation S228P.

The term "Fc-region" herein is used to define a C-terminal region of an immunoglobulin heavy chain that contains at least a portion of the constant region. The term includes native sequence Fc-regions and variant Fc-regions. In one embodiment, a human IgG heavy chain Fc-region extends from Cys226, or from Pro230, to the carboxyl-terminus of the heavy chain. However, the C-terminal lysine (Lys447) of the Fc-region may or may not be present.

The antibodies as reported herein comprise as Fc-region, in one embodiment an Fc-region derived from human origin.

In one embodiment the Fc-region comprises all parts of the human constant region. The Fc-region of an antibody is directly involved in complement activation, C1q binding, C3 activation and Fc receptor binding. While the influence of an antibody on the complement system is dependent on certain conditions, binding to C1q is caused by defined binding sites in the Fc-region. Such binding sites are known in the state of the art and described e.g. by Lukas, T. J., et al., J. Immunol. 127 (1981) 2555-2560; Brunhouse, R. and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434. Such binding sites are e.g. L234, L235, D270, N297, E318, K320, K322, P331 and P329 (numbering according to EU index of Kabat). Antibodies of subclass IgG1, IgG2 and IgG3 usually show complement activation, C1q binding and C3 activation, whereas IgG4 do not activate the complement system, do not bind C1q and do not activate C3.

An "Fc-region of an antibody" is a term well known to the skilled artisan and defined on the basis of papain cleavage of antibodies. In one embodiment the Fc-region is a human Fc-region. In one embodiment the Fc-region is of the human IgG4 subclass comprising the mutations S228P and/or L235E (numbering according to EU index of Kabat). In one embodiment the Fc-region is of the human IgG1 subclass comprising the mutations L234A and L235A (numbering according to EU index of Kabat).

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3 (L3)-FR4.

The terms "full length antibody", "intact antibody," and "whole antibody" are used herein interchangeably to refer to an antibody having a structure substantially similar to a native antibody structure or having heavy chains that contain an Fc-region as defined herein. A "full length antibody" is an antibody that comprises an antigen-binding variable region as well as a light chain constant domain (CL) and heavy chain constant domains, CH1, CH2 and CH3. The constant domains may be native sequence constant domains (e.g. human native sequence constant domains) or amino acid sequence variants thereof. In more detail a full length antibody comprises two antibody light chains (each comprising a light chain variable domain and a light chain constant domain) and two antibody heavy chains (each comprising a heavy chain variable domain, a hinge region and the heavy chain constant domains CH1, CH2 and CH3). The C-terminal amino acid residues K or GK may be present or not independently of each other in the two antibody heavy chains of a full length antibody.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain comprising the amino acid residue stretches which are hypervariable in sequence ("complementarity determining regions" or "CDRs") and/or form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3).

HVRs include
(a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);
(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, Md. (1991), NIH Publication 91-3242.);
(c) antigen contacts occurring at amino acid residues 27c-36 (L1), 46-55 (L2), 89-96 (L3), 30-35b (H1), 47-58 (H2), and 93-101 (H3) (MacCallum et al., J. Mol. Biol. 262 (1996) 732-745); and
(d) combinations of (a), (b), and/or (c), including amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one, which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S., et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-human CD20/human transferrin receptor antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3), whereby between the first and the second constant domain a hinge region is located. Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code.

The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies as reported herein are used to delay development of a disease or to slow the progression of a disease.

The term "variable region" or "variable domain" refers to the domain of an antibody heavy or light chain that is involved in binding the antibody to antigen.

The variable domains of the heavy chain and light chain (VH and VL, respectively) of a native antibody generally have similar structures, with each domain comprising four conserved framework regions (FRs) and three hypervariable regions (HVRs) (see, e.g., Kindt, T. J. et al., Kuby Immunology, 6th ed., W.H. Freeman and Co., N.Y. (2007), page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano, S., et al., J. Immunol. 150 (1993) 880-887; Clackson, T., et al., Nature 352 (1991) 624-628).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The term "immunosuppressive agent" as used herein for adjunct therapy refers to substances that act to suppress or mask the immune system of the mammal being treated herein. This would include substances that suppress cytokine production, down-regulate or suppress self-antigen expression, or mask the MHC antigens. Examples of such agents include 2-amino-6-aryl-5-substituted pyrimidines (see U.S. Pat. No. 4,665,077); azathioprine; cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as glucocorticosteroids, e.g., prednisone, methylprednisolone, and dexamethasone; cytokine or cytokine receptor antagonists including anti-interferon-γ, -β, or -α antibodies, anti-tumor necrosis factor-α antibodies, anti-tumor necrosis factor-β antibodies, anti-interleukin-2 antibodies and anti-IL-2 receptor antibodies; anti-LFA-1 antibodies, including anti-CD11a and anti-CD18 antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187); streptokinase; TGF-β; streptodornase; RNA or DNA from the host; FK506; RS-61443; deoxyspergualin; rapamycin; T-cell receptor (U.S. Pat. No. 5,114,721); T-cell receptor fragments (Offner et al., Science 251 (1991) 430-432; WO 90/11294; Ianeway, Nature 341 (1989) 482; and WO 91/01133); and T cell receptor antibodies (EP 0,340,109) such as T10B9.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2''-trichloro triethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhône-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

II. Compositions and Methods

In one aspect, the invention is based, in part, on the finding that the bispecific anti-human CD20/human transferrin receptor antibody as reported herein has improved properties. In certain embodiments, bispecific anti-human CD20/human transferrin receptor antibodies are provided. Antibodies as reported herein are useful, e.g., for the diagnosis or treatment of Parkinson's disease or multiple sclerosis.

A. Exemplary Bispecific Anti-Human CD20/Human Transferrin Receptor Antibodies

In one aspect, the invention provides isolated bispecific antibodies that bind to human CD20 and human transferrin receptor. The antibodies are bispecific antibodies consisting of a (full length) core antibody and a fused Fab fragment in which certain domains are crosswise exchanged. Thus, the resulting bispecific antibody is asymmetric. Therefore, the bispecific antibodies are produced using the heterodimerization technology called knobs-into-holes using a first heavy chain with the so-called knob mutations (HCknob) and a second heavy chain with the so-called hole mutations (HChole).

Antibody 0039, which is also an aspect of the current invention, is composed of four polypeptides that have the amino acid sequence of SEQ ID NO: 06 to 09.

Antibody 0039 is a bispecific antibody comprising
a) one full length antibody comprising two pairs each of a full length antibody light chain and a full length antibody heavy chain, wherein the binding sites formed by each of the pairs of the full length heavy chain and the full length light chain specifically bind to a first antigen, and
b) one additional Fab fragment, wherein the additional Fab fragment is fused to the C-terminus of one heavy chain of the full length antibody, wherein the binding site of the additional Fab fragment specifically binds to a second antigen,
wherein each of the full length antibody light chains comprises in the constant light chain domain (CL) at position 123 the amino acid residue arginine (instead of the wild-type glutamic acid residue; E123R mutation) and at position 124 the amino acid residue lysine (instead of the wild-type glutamine residue; Q124K mutation) (numbering according to Kabat),
wherein each of the full length antibody heavy chains comprises in the first constant heavy chain domain (CH1) at position 147 an glutamic acid residue (instead of the wild-type lysine residue; K147E mutation) and at position 213 an glutamic acid residue (instead of the wild-type lysine amino acid residue; K213E mutation) (numbering according to Kabat EU index),
wherein the additional Fab fragment specifically binding to the second antigen comprises a domain crossover such that the light chain variable domain (VL) and the heavy chain variable domain (VH) are replaced by each other, and
wherein the first antigen is human CD20 and the second antigen is human transferrin receptor.

Antibody 0041, which is also an aspect of the current invention, is composed of four polypeptides that have the amino acid sequence of SEQ ID NO: 01 to 03 and SEQ ID NO: 10.

Antibody 0041 is a bispecific antibody comprising
a) one full length antibody comprising two pairs each of a full length antibody light chain and a full length antibody heavy chain, wherein the binding sites formed by each of the pairs of the full length heavy chain and the full length light chain specifically bind to a first antigen, and
b) one additional Fab fragment, wherein the additional Fab fragment is fused to the C-terminus of one heavy chain of the full length antibody, wherein the binding site of the additional Fab fragment specifically binds to a second antigen,
wherein each of the full length antibody light chains comprises in the constant light chain domain (CL) at position 123 the amino acid residue arginine (instead of the wild-type glutamic acid residue; E123R mutation) and at position 124 the amino acid residue lysine (instead of the wild-type glutamine residue; Q124K mutation) (numbering according to Kabat),
wherein each of the full length antibody heavy chains comprises in the first constant heavy chain domain (CH1) at position 147 an glutamic acid residue (instead of the wild-type lysine residue; K147E mutation) and at position 213 an glutamic acid residue (instead of the wild-type lysine amino acid residue; K213E mutation) (numbering according to Kabat EU index),
wherein the additional Fab fragment specifically binding to the second antigen comprises a domain crossover such that the constant light chain domain (CL) and the constant heavy chain domain 1 (CH1) are replaced by each other, and
wherein the first antigen is human CD20 and the second antigen is human transferrin receptor.

Antibody 0040, which is also an aspect of the current invention, is composed of three polypeptides that have the amino acid sequence of SEQ ID NO: 11 to 13 and SEQ ID NO: 22.

Antibody 0040 is a bispecific antibody comprising
a) one full length antibody comprising two pairs each of a full length antibody light chain and a full length antibody heavy chain, wherein the binding sites formed by each of the pairs of the full length heavy chain and the full length light chain specifically bind to a first antigen, and
b) one additional Fab fragment, wherein the additional Fab fragment is fused to the C-terminus of one heavy chain of the full length antibody, wherein the binding site of the additional Fab fragment specifically binds to a second antigen,
wherein the additional Fab fragment specifically binding to the second antigen comprises a domain crossover such that the constant light chain domain (CL) and the constant heavy chain domain 1 (CH1) are replaced by each other, and
wherein the first antigen is human CD20 and the second antigen is human transferrin receptor.

Antibody 0042, which is also an aspect of the current invention, is composed of four polypeptides that have the amino acid sequence of SEQ ID NO: 14 to 17.

Antibody 0042 is a bispecific antibody comprising
a) a first light chain and a first heavy chain derived from a first antibody which specifically binds to a first antigen; and
b) a second light chain and a second heavy chain derived from a second antibody which specifically binds to a second antigen, wherein in the second light chain the constant domain CL is replaced by the constant domain CH1 of the second heavy chain; and in the second heavy chain the constant domain CH1 is replaced by the constant domain CL of the second light chain; and i) wherein in the constant domain CL of the first light chain the amino acids at position 124 and 123 (numbering according to Kabat) are substituted independently from each other by an amino acid selected from K, R and H; and wherein in the constant domain CH1 of the first heavy chain the amino acids at position 147 and 213 (numbering according to EU index of Kabat) are substituted independently from each other by an amino acid selected from E or D; or ii) wherein in the constant domain CL of the second heavy chain the amino acids at position 124 and 123 (numbering according to Kabat) are substituted independently from each other by an amino acid selected from K, R and H; and wherein in the constant domain CH1 of the second light chain the amino acids at position 147 and 213 (numbering according to EU index of Kabat) are substituted independently from each other by an amino acid selected from E or D.

The bispecific antibodies as reported herein have been obtained by transient expression in CHO cells. The yields are shown in the following Table.

|  | antibody | | | |
|---|---|---|---|---|
|  | 0039 | 0040 | 0041 | 0042 |
| c [µg/ml] | 8.4 | 25.3 | 32 | 22.5 |
| amount [mg] | 29.4 | 88.6 | 112.0 | 78.8 |

Different allocation/combination of the respective polypeptides on different expression plasmids and different ratios of the resulting plasmids have been used for the recombinant production of the bispecific antibodies. The results obtained in HEK 293 cells are presented in the following Table.

|  |  |  | relative peak area (non-reduced) [%] | | |
|---|---|---|---|---|---|
| antibody | molar plasmid ratio | | ½ mAb hole | hole-hole chain dimer | antibody monomer |
| 0039 | 1:3 | LC + HC-hole:CrossLC + | 9 | 10 | 80 |
| 0039 | 1:4 | HCknob | 6 | 6 | 88 |
| 0039 | 1:3:2 | LC + HC-hole:CrossLC + | 17 | 9 | 74 |
| 0039 | 1:4:2 | HCknob:CrossLC | 10 | 5 | 85 |
| 0039 | 1:1:3 | LC:LC + HC-hole:CrossLC + | 6 | 6 | 88 |
| 0039 | 1:1:4 | HCknob | 3 | 4 | 93 |
| 0040 | 1:3 | LC + HC-hole:CrossLC + | 10 | 18 | 72 |
| 0040 | 1:4 | HCknob | 6 | 7 | 87 |
| 0040 | 1:3:2 | LC + HC-hole:CrossLC + | 5 | 7 | 89 |
| 0040 | 1:4:2 | HCknob:CrossLC | 3 | 5 | 92 |
| 0040 | 1:1:3 | LC:LC + HC-hole:CrossLC + | 16 | 48 | 35 |
| 0040 | 1:1:4 | HCknob | 6 | 23 | 69 |
| 0041 | 1:3 | LC + HC-hole:CrossLC + | 3 | 5 | 92 |
| 0041 | 1:4 | HCknob | 1 | 2 | 97 |
| 0041 | 1:3:2 | LC + HC-hole:CrossLC + | — | 2 | 98 |
| 0041 | 1:4:2 | HCknob:CrossLC | — | 1 | 99 |
| 0041 | 1:1:3 | LC:LC + HC-hole:CrossLC + | — | 3 | 97 |
| 0041 | 1:1:4 | HCknob | — | 2 | 97 |
| 0042 | 1:2 | LC + HC-hole:CrossLC + HCknob | — | 1 | 99 |

The bispecific antibodies have been produced in CHO cells in small scale and the by-product distribution has been analyzed after a first purification step using a protein A affinity chromatography and after the second purification step using a preparative size-exclusion chromatography. The results are presented in the following Table.

| antibody | molar plasmid ratio | harvest 3 liter fermentation after protein A product monomer (CE-SDS not red./ yield) | by-product distribution (CE-SDS not red.) | | | |
|---|---|---|---|---|---|---|
|  |  |  | LC | HC hole | ½ mAb hole | hole-hole dimer + ¾ mAb |
| 0039 | 1:3:2 | 55% 26 mg | 16 | 6 | 11 | 12 |
| 0040 | 1:3:2 | 44% 74.5 mg | 23 | 8 | 7 | 17 |
| 0041 | 1:3:2 | 82% >80 mg | 11 | 0 | 0 | 7 |
| 0042 | 1:2 | 83% 68.4 mg | 9 | 0 | 0 | 8 |

| antibody | plasmid ratio | harvest 3 liter fermentation after protein A and preparative SEC product monomer (CE-SDS not red./ yield) | by-product distribution (CE-SDS not red.) | | | |
|---|---|---|---|---|---|---|
|  |  |  | LC | HC hole | ½ mAb hole | hole-hole dimer + ¾ mAb |
| 0039 | 1:3:2 | 8.2 mg 73% | 10 | 0 | 2 | 15 |
| 0040 | 1:3:2 | 29.7 mg 77% | 10 | 0 | 0 | 14 |

-continued

| antibody | plasmid ratio | harvest 3 l after protein A purification monomer SEC | by-products SEC [%] HMW | by-products SEC [%] LMW | end product SEC | by-products SEC [%] HMW | by-products SEC [%] LMW |
|---|---|---|---|---|---|---|---|
| 0041 | 1:3:2 | >44 mg 79% | 8 | 0 | 0 | | 13 |
| 0042 | 1:2 | 43.6 mg >90% | 3 | 0 | 0 | | 3 |

| antibody | plasmid ratio | harvest 3 l after protein A purification monomer SEC | by-products SEC [%] HMW | by-products SEC [%] LMW | end product SEC | by-products SEC [%] HMW | by-products SEC [%] LMW |
|---|---|---|---|---|---|---|---|
| 0039 | 1:3:2 | 90% | 2 | 7 | 95% | 0 | 5 |
| 0040 | 1:3:2 | 89% | 5 | 6 | 96.5% | 1 | 2.5 |
| 0041 | 1:3:2 | 94% | 6 | 0 | 97.5% | 0.5 | 2 |
| 0042 | 1:2 | 95% | 2 | 3 | 97% | 1 | 2 |

The bispecific antibodies have been produced in different cell lines. The results are shown in the following Table.

| antibody | micro purification with protein A product monomer (CE-SDS) CHO-K1 | micro purification with protein A product monomer (CE-SDS) HEK293 | harvest 3 l after protein A purification monomer (yield/CE-SDS not red.) CHO | end product (preparative protein A and preparative SEC purification) (yield/CE-SDS not red.) CHO |
|---|---|---|---|---|
| 0039 | 80% | 93% | 7.4 mg/l 55% | 8.2 mg 73% |
| 0040 | 83% | 92% | 21.3 mg/l 44% | 29.7 mg 77% |
| 0041 | 85% | 99% | >21 mg/l 82% | >44 mg 79% |
| 0042 | 91% | 99% | 19 mg/l 83% | 43.8 mg 94% |

The aggregation temperature for antibodies 0039, 0040, 0041 and 0042 was determined to be approx. 54-56° C., approx. 50-53° C., approx. 51-53° C., and approx. 55-57° C., respectively.

Overall antibody 0041 showed improved properties and is therefore the preferred aspect of the invention. The improved properties lie, amongst others, in the improved side-product profile.

One aspect as reported herein is a bispecific antibody comprising
  a) one full length antibody comprising two pairs each of a full length antibody light chain and a full length antibody heavy chain, wherein the binding sites formed by each of the pairs of the full length heavy chain and the full length light chain specifically bind to a first antigen, and
  b) one additional Fab fragment, wherein the additional Fab fragment is fused to the C-terminus of one heavy chain of the full length antibody, wherein the binding site of the additional Fab fragment specifically binds to a second antigen,
  wherein each of the full length antibody light chains comprises in the constant light chain domain (CL) at position 123 the amino acid residue arginine (instead of the wild-type glutamic acid residue; E123R mutation) and at position 124 the amino acid residue lysine (instead of the wild-type glutamine residue; Q124K mutation) (numbering according to Kabat),
  wherein each of the full length antibody heavy chains comprises in the first constant heavy chain domain (CH1) at position 147 an glutamic acid residue (instead of the wild-type lysine residue; K147E mutation) and at position 213 an glutamic acid residue (instead of the wild-type lysine amino acid residue; K213E mutation) (numbering according to Kabat EU index),
  wherein the additional Fab fragment specifically binding to the second antigen comprises a domain crossover such that the constant light chain domain (CL) and the constant heavy chain domain 1 (CH1) are replaced by each other, and
  wherein the first antigen is human CD20 and the second antigen is human transferrin receptor.

One aspect as reported herein is a bispecific antibody comprising
  a) one full length antibody comprising two pairs each of a full length antibody light chain and a full length antibody heavy chain, wherein the binding sites formed by each of the pairs of the full length heavy chain and the full length light chain specifically bind to a first antigen, and
  b) one additional Fab fragment, wherein the additional Fab fragment is fused to the C-terminus of one heavy chain of the full length antibody, wherein the binding site of the additional Fab fragment specifically binds to a second antigen,
  wherein each of the full length antibody light chains comprises in the constant light chain domain (CL) at position 123 the amino acid residue arginine (instead of the wild-type glutamic acid residue; E123R mutation) and at position 124 the amino acid residue lysine (instead of the wild-type glutamine residue; Q124K mutation) (numbering according to Kabat),
  wherein each of the full length antibody heavy chains comprises in the first constant heavy chain domain (CH1) at position 147 an glutamic acid residue (instead of the wild-type lysine residue; K147E mutation) and at position 213 an glutamic acid residue (instead of the wild-type lysine amino acid residue; K213E mutation) (numbering according to Kabat EU index),
  wherein the additional Fab fragment specifically binding to the second antigen comprises a domain crossover such that the constant light chain domain (CL) and the constant heavy chain domain 1 (CH1) are replaced by each other,
  wherein the first antigen is human CD20 and the second antigen is human transferrin receptor,
  wherein the human CD20 binding site comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 18 and a light chain variable domain (VL) sequence having at least 90%, 91%, 92%, 93%, 94%, 95%, 96%, 97%, 98%, 99%, or 100% sequence identity to the amino acid sequence of SEQ ID NO: 19, and
  wherein the human transferrin receptor binding site comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 20 and a light chain variable domain (VL) sequence having at least 90%, 91%, 92%, 93%, 94%, 95%, 96%, 97%, 98%, 99%, or 100% sequence identity to the amino acid sequence of SEQ ID NO: 21.

In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but a binding site comprising that sequence retains the ability to bind to its antigen. In certain embodiments, a total of 1 to 10 amino acids have been substituted, inserted and/or deleted in SEQ ID NO: 18 or 20. In certain embodiments, substitutions, insertions, or deletions occur in regions outside the HVRs (i.e., in the FRs).

In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but a binding site comprising that sequence retains the ability to bind to its antigen. In certain embodiments, a total of 1 to 10 amino acids have been substituted, inserted and/or deleted in SEQ ID NO: 19 or 21. In certain embodiments, substitutions, insertions, or deletions occur in regions outside the HVRs (i.e., in the FRs).

In one embodiment, the human CD20 binding site comprises the VH sequence as in SEQ ID NO: 18, including post-translational modifications of that sequence and the VL sequence as in SEQ ID NO: 19, including post-translational modifications of that sequence.

In one embodiment, the human transferrin receptor binding site comprises the VH sequence as in SEQ ID NO: 20, including post-translational modifications of that sequence and the VL sequence as in SEQ ID NO: 21, including post-translational modifications of that sequence.

In one embodiment the bispecific antibody comprises
i) a light chain that has a sequence identity to SEQ ID NO: 01 of at least 70%, at least 80%, at least 90%, or 95% or more,
ii) a heavy chain that has a sequence identity to SEQ ID NO: 02 of at least 70%, at least 80%, at least 90%, or 95% or more,
iii) a light chain that has a sequence identity to SEQ ID NO: 03 of at least 70%, at least 80%, at least 90%, or 95% or more, and
iv) a heavy chain Fab fragment that has a sequence identity to SEQ ID NO: 04 of at least 70%, at least 80%, at least 90%, or 95% or more,
wherein

```
SEQ ID NO: 01 has the amino acid sequence
DIVMTQTPLSLPVTPGEPASISCRSSKSLLHSNGITYLYWYLQKPGQS

PQLLIYQMSNLVSGVPDRFSGSGSGTDFTLKISRVEAEDVGVYYCAQN

LELPYTFGGGTKVEIKRTVAAPSVFIFPPSDRKLKSGTASVVCLLNNF

YPREAKVQWKVDNALQSGNSQESVTEQDSKDSTYSLSSTLTLSKADYE

KHKVYACEVTHQGLSSPVTKSFNRGEC,

SEQ ID NO: 02 has the amino acid sequence
QVQLVQSGAEVKKPGSSVKVSCKASGYAFSYSWINWVRQAPGQGLEWM

GRIFPGDGDTDYNGKFKGRVTITADKSTSTAYMELSSLRSEDTAVYYC

ARNVFDGYWLVYWGQGTLVTVSSASTKGPSVFPLAPSSKSTSGGTAAL

GCLVEDYFPEPVTVSWNSGALTSGVHTFPAVLQSSGLYSLSSVVTVPS

SSLGTQTYICNVNHKPSNTKVDEKVEPKSCDKTHTCPPCPAPEAAGGP

SVFLFPPKPKDTLMISRTPEVTCVVVDVSHEDPEVKFNWYVDGVEVHN

AKTKPREEQYNSTYRVVSVLTVLHQDWLNGKEYKCKVSNKALGAPIEK

TISKAKGQPREPQVCTLPPSRDELTKNQVSLSCAVKGFYPSDIAVEWE

SNGQPENNYKTTPPVLDSDGSFFLVSKLTVDKSRWQQGNVFSCSVMHE

ALHNHYTQKSLSLSPG,

SEQ ID NO: 03 has the amino acid sequence
AIQLTQSPSSLSASVGDRVTITCRASQSISSYLAWYQQKPGKAPKLLI

YRASTLASGVPSRFSGSGSGTDFTLTISSLQPEDFATYYCQQNYASSN

VDNTFGGGTKVEIKSSASTKGPSVFPLAPSSKSTSGGTAALGCLVKDY

FPEPVTVSWNSGALTSGVHTFPAVLQSSGLYSLSSVVTVPSSSLGTQT

YICNVNHKPSNTKVDKKVEPKSC,
and

SEQ ID NO: 04 has the amino acid sequence
QSMQESGPGLVKPSQTLSLTCTVSGFSLSSYAMSWIRQHPGKGLEWIG

YIWSGGSTDYASWAKSRVTISKTSTTVSLKLSSVTAADTAVYYCARRY

GTSYPDYGDASGFDPWGQGTLVTVSSASVAAPSVFIFPPSDEQLKSGT

ASVVCLLNNFYPREAKVQWKVDNALQSGNSQESVTEQDSKDSTYSLSS

TLTLSKADYEKHKVYACEVTHQGLSSPVTKSFNRGEC.
```

One aspect as reported herein is a bispecific antibody comprising
a) one full length antibody comprising two pairs each of a full length antibody light chain and a full length antibody heavy chain, wherein the binding sites formed by each of the pairs of the full length heavy chain and the full length light chain specifically bind to a first antigen, and
b) one additional Fab fragment, wherein the additional Fab fragment is fused to the C-terminus of one heavy chain of the full length antibody, wherein the binding site of the additional Fab fragment specifically binds to a second antigen,
wherein each of the full length antibody light chains comprises in the constant light chain domain (CL) at position 123 the amino acid residue arginine (instead of the wild-type glutamic acid residue; E123R mutation) and at position 124 the amino acid residue lysine (instead of the wild-type glutamine residue; Q124K mutation) (numbering according to Kabat),
wherein each of the full length antibody heavy chains comprises in the first constant heavy chain domain (CH1) at position 147 an glutamic acid residue (instead of the wild-type lysine residue; K147E mutation) and at position 213 an glutamic acid residue (instead of the wild-type lysine amino acid residue; K213E mutation) (numbering according to Kabat EU index),
wherein the additional Fab fragment specifically binding to the second antigen comprises a domain crossover such that the constant light chain domain (CL) and the constant heavy chain domain 1 (CH1) are replaced by each other,
wherein the first antigen is human CD20 and the second antigen is human transferrin receptor,
wherein the human CD20 binding site comprises a heavy chain variable domain (VH) that has the amino acid sequence of SEQ ID NO: 18 and a light chain variable domain (VL) that has the amino acid sequence of SEQ ID NO: 19, and
wherein the human transferrin receptor binding site comprises a heavy chain variable domain (VH) that has the amino acid sequence of SEQ ID NO: 20 and a light chain variable domain (VL) that has the amino acid sequence of SEQ ID NO: 21.

One aspect as reported herein is a bispecific antibody comprising
- a) one full length antibody comprising two pairs each of a full length antibody light chain and a full length antibody heavy chain, wherein the binding sites formed by each of the pairs of the full length heavy chain and the full length light chain specifically bind to a first antigen, wherein the full length antibody comprises an Fc-region that is formed by the Fc-region polypeptides, each comprising the CH1, CH2 and CH3 domain, of the two full length heavy chains and
- b) one additional Fab fragment, wherein the additional Fab fragment is fused to the C-terminus of one heavy chain of the full length antibody, wherein the binding site of the additional Fab fragment specifically binds to a second antigen, wherein each of the full length antibody light chains comprises in the constant light chain domain (CL) at position 123 the amino acid residue arginine (instead of the wild-type glutamic acid residue; E123R mutation) and at position 124 the amino acid residue lysine (instead of the wild-type glutamine residue; Q124K mutation) (numbering according to Kabat), wherein each of the full length antibody heavy chains comprises in the first constant heavy chain domain (CH1) at position 147 an glutamic acid residue (instead of the wild-type lysine residue; K147E mutation) and at position 213 an glutamic acid residue (instead of the wild-type lysine amino acid residue; K213E mutation) (numbering according to Kabat EU index), wherein the additional Fab fragment specifically binding to the second antigen comprises a domain crossover such that the constant light chain domain (CL) and the constant heavy chain domain 1 (CH1) are replaced by each other, wherein the first antigen is human CD20 and the second antigen is human transferrin receptor, wherein the human CD20 binding site comprises a heavy chain variable domain (VH) that has the amino acid sequence of SEQ ID NO: 18 and a light chain variable domain (VL) that has the amino acid sequence of SEQ ID NO: 19, wherein the human transferrin receptor binding site comprises a heavy chain variable domain (VH) that has the amino acid sequence of SEQ ID NO: 20 and a light chain variable domain (VL) that has the amino acid sequence of SEQ ID NO: 21, and wherein the Fc-region polypeptides are
- a) of the human subclass IgG1,
- b) of the human subclass IgG4,
- c) of the human subclass IgG1 with the mutations L234A, L235A and P329G,
- d) of the human subclass IgG4 with the mutations S228P, L235E and P329G,
- e) of the human subclass IgG1 with the mutations L234A, L235A and P329G in both Fc-region polypeptides and the mutations T366W and S354C in one Fc-region polypeptide and the mutations T366S, L368A, Y407V and Y349C in the respective other Fc-region polypeptide,
- f) of the human subclass IgG4 with the mutations S228P and P329G in both Fc-region polypeptides and the mutations T366W and S354C in one Fc-region polypeptide and the mutations T366S, L368A, Y407V and Y349C in the respective other Fc-region polypeptide,
- g) of the human subclass IgG1 with the mutations L234A, L235A, P329G, I253A, H310A and H435A in both Fc-region polypeptides and the mutations T366W and S354C in one Fc-region polypeptide and the mutations T366S, L368A, Y407V and Y349C in the respective other Fc-region polypeptide, or
- h) of the human subclass IgG1 with the mutations L234A, L235A, P329G, M252Y, S254T and T256E in both Fc-region polypeptides and the mutations T366W and S354C in one Fc-region polypeptide and the mutations T366S, L368A, Y407V and Y349C in the respective other Fc-region polypeptide, or
- i) a full length antibody of the human subclass IgG1 with the mutations L234A, L235A, P329G, H310A, H433A and Y436A in both heavy chains and the mutations i) T366W, and ii) S354C or Y349C, in one heavy chain and the mutations i) T366S, L368A, and Y407V, and ii) Y349C or S354C, in the respective other heavy chain.

In a further aspect, a bispecific anti-human CD20/human transferrin receptor antibody according to any of the above embodiments may incorporate any of the features, singly or in combination, as described in Sections 1-3 below:

1. Chimeric and Humanized Antibodies

In certain embodiments, an antibody provided herein is a chimeric antibody. Certain chimeric antibodies are described, e.g., in U.S. Pat. No. 4,816,567; and Morrison, S. L. et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I. et al., Nature 332 (1988) 323-329; Queen, C. et al., Proc. Natl. Acad. Sci. USA 86 (1989) 10029-10033; U.S. Pat. Nos. 5,821,337, 7,527,791, 6,982,321, and 7,087,409; Kashmiri, S. V. et al., Methods 36 (2005) 25-34 (describing specificity determining region (SDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J. et al., J. Immunol. 151 (1993) 2296-2308; framework regions derived from the consensus sequence of human antibodies of a particular subgroup of light or heavy chain variable regions (see, e.g., Carter, P. et al., Proc. Natl. Acad. Sci. USA 89 (1992) 4285-4289; and Presta, L. G. et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

2. Human Antibodies

In certain embodiments, an antibody provided herein is a human antibody. Human antibodies can be produced using various techniques known in the art. Human antibodies are described generally in van Dijk, M. A. and van de Winkel, J. G., Curr. Opin. Pharmacol. 5 (2001) 368-374 and Lonberg, N., Curr. Opin. Immunol. 20 (2008) 450-459.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, N., Nat. Biotech. 23 (2005) 1117-1125. See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor, D., J. Immunol. 133 (1984) 3001-3005; Brodeur, B. R. et al., Monoclonal Antibody Production Techniques and Applications, Marcel Dekker, Inc., New York (1987), pp. 51-63; and Boerner, P. et al., J. Immunol. 147 (1991) 86-95) Human antibodies generated via human B-cell hybridoma technology are also described in Li, J. et al., Proc. Natl. Acad. Sci. USA 103 (2006) 3557-3562. Additional methods include those described, for example, in U.S. Pat. No. 7,189,826 (describing production of monoclonal human IgM antibodies from hybridoma cell lines) and Ni, J., Xiandai Mianyixue 26 (2006) 265-268 (describing human-human hybridomas). Human hybridoma technology (Trioma technology) is also described in Vollmers, H. P. and Brandlein, S., Histology and Histopathology 20 (2005) 927-937 and Vollmers, H. P. and Brandlein, S., Methods and Findings in Experimental and Clinical Pharmacology 27 (2005) 185-191.

Human antibodies may also be generated by isolating Fv clone variable domain sequences selected from human-derived phage display libraries. Such variable domain sequences may then be combined with a desired human constant domain.

3. Antibody Variants

In certain embodiments, amino acid sequence variants of the bispecific antibodies as provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in the Table below under the heading of "preferred substitutions". More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or residues that contact antigen, with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, a bispecific antibody as provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc-region, the carbohydrate attached thereto may be altered. Native antibodies produced by mammalian cells typically comprise a branched, biantennary oligosaccharide that is generally attached by an N-linkage to Asn297 of the CH2 domain of the Fc-region. See, e.g., Wright, A. and Morrison, S. L., TIBTECH 15 (1997) 26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody as reported herein may be made in order to create antibody variants with certain improved properties.

In one embodiment, antibody variants are provided having a carbohydrate structure that lacks fucose attached (directly or indirectly) to an Fc-region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc-region (EU numbering of Fc-region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J. et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N. et al., Biotech. Bioeng. 87 (2004) 614-622; Kanda, Y. et al., Biotechnol. Bioeng. 94 (2006) 680-688; and WO 2003/085107).

Antibodies variants are further provided with bisected oligosaccharides, e.g., in which a biantennary oligosaccharide attached to the Fc-region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc-region are also provided. Such antibody variants may have improved CDC function. Such antibody variants are described, e.g., in WO 1997/30087; WO 1998/58964; and WO 1999/22764.

c) Fc-Region Variants

In certain embodiments, one or more amino acid modifications may be introduced into the Fc-region of a bispecific antibody as provided herein, thereby generating an Fc-region variant. The Fc-region variant may comprise a human Fc-region sequence (e.g., a human IgG1, IgG2, IgG3 or IgG4 Fc-region) comprising an amino acid modification (e.g. a substitution) at one or more amino acid positions.

In certain embodiments, herein is contemplated an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express FcγRI, FcγRII and FcγRIII. FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest is described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006: 1759-1769).

Antibodies with reduced effector function include those with substitution of one or more of Fc-region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L. et al., J. Biol. Chem. 276 (2001) 6591-6604)

In certain embodiments, an antibody variant comprises an Fc-region with one or more amino acid substitutions, which improve ADCC, e.g., substitutions at positions 298, 333, and/or 334 of the Fc-region (EU numbering of residues).

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc-region with one or more substitutions therein which improve binding of the Fc-region to FcRn. Such Fc variants include those with substitutions at one or more of Fc-region residues: 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc-region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc-region. Cysteine engineered antibodies may be generated as described, e.g., in U.S. Pat. No. 7,521,541.

e) Antibody Derivatives

In certain embodiments, a bispecific antibody as provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding a bispecific anti-human CD20/human transferrin receptor antibody described herein is provided. In a further embodiment, one or more vectors (e.g., expression vectors) comprising such nucleic acid are provided. In a further embodiment, a host cell comprising such nucleic acid is provided. In one embodiment, the host cell is eukaryotic, e.g. a Chinese Hamster Ovary (CHO) cell or lymphoid cell (e.g., Y0, NS0, Sp20 cell). In one embodiment, a method of making a bispecific anti-human CD20/human transferrin receptor antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of a bispecific anti-human CD20/human transferrin receptor antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR⁻ CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

C. Methods and Compositions for Diagnostics and Detection

In certain embodiments, any of the bispecific anti-human CD20/human transferrin receptor antibodies provided herein are useful for detecting the presence of CD20 in a biological sample. The term "detecting" as used herein encompasses quantitative or qualitative detection. In certain embodiments, a biological sample comprises a cell or tissue.

In one embodiment, a bispecific anti-human CD20/human transferrin receptor antibody for use in a method of diagnosis or detection is provided. In a further aspect, a method of detecting the presence of CD20 in a biological sample is provided. In certain embodiments, the method comprises contacting the biological sample with a bispecific anti-human CD20/human transferrin receptor antibody as described herein under conditions permissive for binding of the bispecific anti-human CD20/human transferrin receptor antibody to CD20, and detecting whether a complex is formed between the bispecific anti-human CD20/human transferrin receptor antibody and CD20. Such method may be an in vitro or in vivo method.

In certain embodiments, labeled bispecific anti-human CD20/human transferrin receptor antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

D. Immunoconjugates

The invention also provides immunoconjugates comprising an anti-human CD20/human transferrin receptor antibody as reported herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which a bispecific antibody is conjugated to one or more drugs, including but not limited to a maytansinoid (see U.S. Pat. Nos. 5,208,020, 5,416,064 and EP 0 425 235 B1); an auristatin such as monomethyl auristatin drug moieties DE and DF (MMAE and MMAF) (see U.S. Pat. Nos. 5,635,483, 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman, L. M. et al., Cancer Res. 53 (1993) 3336-3342; and Lode, H. N. et al., Cancer Res. 58 (1998) 2925-2928); an anthracycline such as daunomycin or doxorubicin (see Kratz, F. et al., Curr. Med. Chem. 13 (2006) 477-523; Jeffrey, S. C. et al., Bioorg. Med. Chem. Lett. 16 (2006) 358-362; Torgov, M. Y. et al., Bioconjug. Chem. 16 (2005) 717-721; Nagy, A. et al., Proc. Natl. Acad. Sci. USA 97 (2000) 829-834; Dubowchik, G. M. et al., Bioorg. & Med. Chem. Letters 12 (2002) 1529-1532; King, H. D. et al., J. Med. Chem. 45 (20029 4336-4343; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises a bispecific antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. See, for example, WO 93/21232 published Oct. 28, 1993.

In another embodiment, an immunoconjugate comprises a bispecific antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{86}$, $Re^{88}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $TC^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of a bispecific antibody and cytotoxic agent may be made using a variety of bifunctional coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta, E. S. et al., Science 238 (1987) 1098-1104. Carbon-14-labeled 1-isothiocyanatobenzyl-3-methyldiethylene triamine pentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari, R. V. et al., Cancer Res. 52 (1992) 127-131; U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A.).

Conjugates of a bispecific antibody as reported herein and one or more small molecule toxins, such as a calicheamicin, a maytansine (U.S. Pat. No. 5,208,020), a trichothene, and CC1065 are also contemplated herein. In one embodiment of the invention, the bispecific antibody is conjugated to one or more maytansine molecules (e.g. about 1 to about 10 maytansine molecules per antagonist molecule). Maytansine may, for example, be converted to May-SS-Me which may be reduced to May-SH3 and reacted with modified antagonist (Chari et al. Cancer Research 52: 127-131 (1992)) to generate a maytansinoid-antibody conjugate.

Alternatively, the bispecific antibody as reported herein is conjugated to one or more calicheamicin molecules. The calicheamicin family of antibiotics are capable of producing double-stranded DNA breaks at sub-picomolar concentrations.

Structural analogues of calicheamicin which may be used include, but are not limited to, γ1 I, α2 I, α3 I, N-acetyl-γ1 I, PSAG and θI 1 (Hinman et al. Cancer Research 53: 3336-3342 (1993) and Lode et al. Cancer Research 58: 2925-2928 (1998)).

The present invention further contemplates a bispecific antibody as reported herein conjugated with a compound with nucleolytic activity (e.g. a ribonuclease or a DNA endonuclease such as a deoxyribonuclease; DNase).

Alternatively, a fusion protein comprising the bispecific antibody as reported herein and cytotoxic agent may be made, e.g. by recombinant techniques or peptide synthesis.

E. Pharmaceutical Formulations

Pharmaceutical formulations of a bispecific anti-human CD20/human transferrin receptor antibody as described herein are prepared by mixing such antibody having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer. Exemplary anti-CD20 antibody formulations are described in WO98/56418, expressly incorporated herein by reference.

Lyophilized formulations adapted for subcutaneous administration are described in WO 97/04801. Such lyophilized formulations may be reconstituted with a suitable diluent to a high protein concentration and the reconstituted formulation may be administered subcutaneously to the mammal to be treated herein.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration are generally sterile. Sterility may be readily accomplished, e.g., by filtration through sterile filtration membranes. In one embodiment the formulation is isotonic.

F. Therapeutic Methods and Compositions

Any of the bispecific anti-human CD20/human transferrin receptor antibodies provided herein may be used in therapeutic methods.

In one aspect, a bispecific anti-human CD20/human transferrin receptor antibody for use as a medicament is provided. In further aspects, a bispecific anti-human CD20/human transferrin receptor antibody for use in preventing and/or treating a B-cell proliferative disease is provided. In certain embodiments, a bispecific anti-human CD20/human transferrin receptor antibody for use in a method of treatment is provided. In certain embodiments, herein is provided a bispecific anti-human CD20/human transferrin receptor antibody for use in a method of treating an individual having a B-cell proliferative disease comprising administering to the individual an effective amount of the bispecific anti-human CD20/human transferrin receptor antibody. In one such embodiment, the method further comprises administering to the individual an effective amount of at least one additional therapeutic agent, such as listed below. In further embodiments, herein is provided a bispecific anti-human CD20/human transferrin receptor antibody for use in depleting brain sequestered B-cells expressing CD20. In certain embodiments, herein is provided a bispecific anti-human CD20/human transferrin receptor antibody for use in a method of depleting brain sequestered B-cells expressing CD20 in an individual comprising administering to the individual an effective of the bispecific anti-human CD20/human transferrin receptor antibody to deplete brain sequestered B-cells expressing CD20. An "individual" according to any of the above embodiments is preferably a human.

In a further aspect, herein is provided the use of a bispecific anti-human CD20/human transferrin receptor antibody in the manufacture or preparation of a medicament. In one embodiment, the medicament is for treatment of a B-cell proliferative disease. In a further embodiment, the medicament is for use in a method of treating a B-cell proliferative disease comprising administering to an individual having a disease associated with B-cell proliferative an effective amount of the medicament. In one such embodiment, the method further comprises administering to the individual an effective amount of at least one additional therapeutic agent, such as listed below. In a further embodiment, the medicament is for the depletion of brain sequestered B-cells expressing CD20. In a further embodiment, the medicament is for use in a method of depleting brain sequestered B-cells expressing CD20 in an individual comprising administering to the individual an amount effective of the medicament to deplete brain sequestered B-cells expressing CD20. An "individual" according to any of the above embodiments may be a human.

In a further aspect, herein is provided a method for treating a B-cell proliferative disease. In one embodiment, the method comprises administering to an individual having a B-cell proliferative disease an effective amount of a bispecific anti-human CD20/human transferrin receptor antibody. In one such embodiment, the method further comprises administering to the individual an effective amount of at least one additional therapeutic agent, such as given below. An "individual" according to any of the above embodiments may be a human.

In a further aspect, herein is provided a method for depleting circulating B-cells expressing CD20 in an individual. In one embodiment, the method comprises administering to the individual an effective amount of a bispecific anti-human CD20/human transferrin receptor antibody to deplete circulating B-cells expressing CD20. In one embodiment, an "individual" is a human.

In a further aspect, herein are provided pharmaceutical formulations comprising any of the bispecific anti-human CD20/human transferrin receptor antibodies provided herein, e.g., for use in any of the above therapeutic methods. In one embodiment, a pharmaceutical formulation comprises any of the bispecific anti-human CD20/human transferrin receptor antibodies provided herein and a pharmaceutically acceptable carrier. In another embodiment, a pharmaceutical formulation comprises any of the bispecific anti-human CD20/human transferrin receptor antibodies provided herein and at least one additional therapeutic agent, e.g., as given below.

Antibodies as reported herein can be used either alone or in combination with other agents in a therapy. For instance, an antibody as reported herein may be co-administered with at least one additional therapeutic agent. In certain embodiments, an additional therapeutic agent is a therapeutic agent effective to treat the same or a different B-cell proliferative disease as the bispecific antibody as reported herein is being employed to treat.

Such combination therapies noted above encompass combined administration (where two or more therapeutic agents are included in the same or separate formulations), and separate administration, in which case, administration of the antibody as reported herein can occur prior to, simultaneously, and/or following, administration of the additional therapeutic agent or agents. In one embodiment, administration of the bispecific anti-human CD20/human transferrin receptor antibody and administration of an additional therapeutic agent occur within about one month, or within about one, two or three weeks, or within about one, two, three, four, five, or six days, of each other. Antibodies as reported herein can also be used in combination with other interventional therapies such as, but not limited to, radiation therapy, behavioral therapy, or other therapies known in the art and appropriate for the neurological disorder to be treated or prevented.

An antibody as reported herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

In addition, the bispecific antibody may suitably be administered by pulse infusion, e.g., with declining doses of the bispecific antibody. The dosing can be given by injections, intravenous or subcutaneous injections, depending in part on whether the administration is brief or chronic.

Antibodies as reported herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

Lipid-based methods of transporting the fusion construct or a compound across the BBB include, but are not limited to, encapsulating the fusion construct or a compound in liposomes that are coupled to monovalent binding entity that bind to receptors on the vascular endothelium of the BBB (see e.g., US 2002/0025313), and coating the monovalent binding entity in low-density lipoprotein particles (see e.g., US 2004/0204354) or apolipoprotein E (see e.g., US 2004/0131692).

For the prevention or treatment of disease, the appropriate dosage of an antibody as reported herein (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.5 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate as reported herein in place of or in addition to a bispecific anti-human CD20/human transferrin receptor antibody.

The composition comprising a bispecific antibody as reported herein which binds to a B-cell surface antigen will be formulated, dosed, and administered in a fashion consistent with good medical practice. Factors for consideration in this context include the particular disease or disorder being treated, the particular mammal being treated, the clinical condition of the individual patient, the cause of the disease or disorder, the site of delivery of the agent, the method of administration, the scheduling of administration, and other factors known to medical practitioners.

The therapeutically effective amount of the antagonist to be administered will be governed by such considerations.

Beside the treatment of B-cell proliferative diseases the bispecific antibody as reported herein can be used in the treatment of autoimmune diseases. Examples of autoimmune diseases or disorders include, but are not limited to, immune-mediated thrombocytopenias, such as acute idiopathic thrombocytopenic purpurea and chronic idiopathic thrombocytopenic purpurea, dermatomyositis, Sydenham's chorea, lupus nephritis, rheumatic fever, polyglandular syndromes, Henoch-Schonlein purpura, post-streptococcal nephritis, erythema nodosum, Takayasu's arteritis, Addison's disease, erythema multiforme, polyarteritis nodosa, ankylosing spondylitis, Goodpasture's syndrome, thromboangitis ubiterans, primary biliary cirrhosis, Hashimoto's thyroiditis, thyrotoxicosis, chronic active hepatitis, polymyositis/dermatomyositis, polychondritis, pamphigus vulgaris, Wegener's granulomatosis, membranous nephropathy, amyotrophic lateral sclerosis, tabes dorsalis, polymyaglia, pernicious anemia, rapidly progressive glomerulonephritis and fibrosing alveolitis, inflammatory responses such as inflammatory skin diseases including psoriasis and dermatitis (e.g. atopic dermatitis); systemic scleroderma and sclerosis; responses associated with inflammatory bowel disease (such as Crohn's disease andulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type 1 diabetes mellitus or insulin dependent diabetes mellitus); multiple sclerosis; Reynaud's syndrome; autoimmune thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious amenia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; anti-phospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Bechet disease; giant cell arteritis; immune complex nephritis; IgA nephropathy; IgM polyneuropathies; immune thrombocytopenic purpura (ITP) or autoimmune thrombocytopenia etc. In this aspect of the invention, the ABMs of the invention are used to deplete the blood of normal B-cells for an extended period.

As noted above, however, these suggested amounts of bispecific antibody are subject to a great deal of therapeutic discretion. The key factor in selecting an appropriate dose and scheduling is the result obtained, as indicated above. For example, relatively higher doses may be needed initially for the treatment of ongoing and acute diseases. To obtain the most efficacious results, depending on the disease or disorder, the antagonist is administered as close to the first sign, diagnosis, appearance, or occurrence of the disease or disorder as possible or during remissions of the disease or disorder.

Aside from administration of isolated bispecific antibodies as reported herein to the patient the present application contemplates administration of the bispecific antibody by gene therapy. Such administration of nucleic acid encoding the bispecific antibody is encompassed by the expression "administering a therapeutically effective amount of a bispecific antibody". See, for example, WO96/07321 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the bispecific antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g. U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., J. Biol. Chem. 262: 4429-4432 (1987); and Wagner et al., Proc. Natl. Acad. Sci. USA 87:3410-3414 (1990). For review of the currently known gene marking and gene therapy protocols see Anderson et al., Science 256:808-813 (1992). See also WO 93/25673 and the references cited therein.

General techniques for conjugating additional therapeutic agents to antibodies are well known (see, e.g., Arnon et al., "Monoclonal Antibodies for Immunotargeting of Drugs in Cancer Therapy", in Monoclonal Antibodies and Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506

(1985); and Thorpe et al., "The Preparation And Cytotoxic Properties Of Antibody-Toxin Conjugates", Immunol. Rev., 62 (1982) 119-58).

III. Articles of Manufacture

In another aspect as reported herein, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition, which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody as reported herein. The label or package insert indicates that the composition is used for treating the condition of choice. Moreover, the article of manufacture may comprise (a) a first container with a composition contained therein, wherein the composition comprises an antibody as reported herein; and (b) a second container with a composition contained therein, wherein the composition comprises a further cytotoxic or otherwise therapeutic agent. The article of manufacture in this embodiment may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate as reported herein in place of or in addition to a bispecific antibody as reported herein.

IV. Examples

The following are examples of methods and compositions of the invention. It is understood that various other embodiments may be practiced, given the general description provided above.

Materials & General Methods

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991). Amino acids of antibody chains are numbered and referred to according to numbering according to Kabat (Kabat, E. A., et al., Sequences of Proteins of Immunological Interest, 5th ed., Public Health Service, National Institutes of Health, Bethesda, Md. (1991)).

Recombinant DNA Techniques

Standard methods were used to manipulate DNA as described in Sambrook, J. et al., Molecular Cloning: A laboratory manual; Cold Spring Harbor Laboratory Press, Cold Spring Harbor, N.Y., 1989. The molecular biological reagents were used according to the manufacturer's instructions.

Gene Synthesis

Desired gene segments were prepared from oligonucleotides made by chemical synthesis. The long gene segments, which were flanked by singular restriction endonuclease cleavage sites, were assembled by annealing and ligating oligonucleotides including PCR amplification and subsequently cloned via the indicated restriction sites. The DNA sequences of the subcloned gene fragments were confirmed by DNA sequencing. Gene synthesis fragments were ordered according to given specifications at Geneart (Regensburg, Germany).

DNA Sequence Determination

DNA sequences were determined by double strand sequencing performed at MediGenomix GmbH (Martinsried, Germany) or SequiServe GmbH (Vaterstetten, Germany).

DNA and Protein Sequence Analysis and Sequence Data Management

The GCG's (Genetics Computer Group, Madison, Wis.) software package version 10.2 and Infomax's Vector NT1 Advance suite version 8.0 was used for sequence creation, mapping, analysis, annotation and illustration.

Expression Vectors

For the expression of the described bispecific antibodies, expression plasmids for transient expression (e.g. in HEK293 cells) based either on a cDNA organization with or without a CMV-intron A promoter or on a genomic organization with a CMV promoter can be applied.

Beside the antibody expression cassette the vectors contain:

an origin of replication which allows replication of this plasmid in E. coli, and
a ß-lactamase gene which confers ampicillin resistance in E. coli.

The transcription unit of the antibody gene is composed of the following elements:

unique restriction site(s) at the 5' end
the immediate early enhancer and promoter from the human cytomegalovirus,
the intron A sequence in the case of cDNA organization,
a 5'-untranslated region derived from a human antibody gene,
an immunoglobulin heavy chain signal sequence,
the respective antibody chain encoding nucleic acid either as cDNA or with genomic exon-intron organization,
a 3' untranslated region with a polyadenylation signal sequence,
a terminator sequence, and
unique restriction site(s) at the 3' end.

The fusion genes encoding the antibody chains are generated by PCR and/or gene synthesis and assembled by known recombinant methods and techniques by connection of the according nucleic acid segments e.g. using unique restriction sites in the respective vectors. The subcloned nucleic acid sequences are verified by DNA sequencing. For transient transfections larger quantities of the plasmids are prepared by plasmid preparation from transformed E. coli cultures (Nucleobond AX, Macherey-Nagel).

For all constructs knob-into-hole heterodimerization technology was used with a typical knob (T366W) substitution in the first CH3 domain and the corresponding hole substitutions (T366S, L368A and Y407V) in the second CH3 domain (as well as two additional introduced cysteine residues S354C/Y349'C) (contained in the respective corresponding heavy chain (HC) sequences depicted above).

Cell Culture Techniques

Standard cell culture techniques as described in Current Protocols in Cell Biology (2000), Bonifacino, J. S., Dasso, M., Harford, J. B., Lippincott-Schwartz, J. and Yamada, K. M. (eds.), John Wiley & Sons, Inc., are used.

Transient Transfections in HEK293 System

The bispecific antibodies are produced by transient expression. Therefore a transfection with the respective plasmids using the HEK293 system (Invitrogen) according to the manufacturer's instruction is done. Briefly, HEK293 cells (Invitrogen) growing in suspension either in a shake flask or in a stirred fermenter in serum-free FreeStyle™ 293 expression medium (Invitrogen) are transfected with a mix of the respective expression plasmids and 293Fectin™ or fectin (Invitrogen). For 2 L shake flask (Corning) HEK293 cells are seeded at a density of $1.0*10^6$ cells/mL in 600 mL and incubated at 120 rpm, 8% $CO_2$. On the next day the cells are transfected at a cell density of approx. $1.5*10^6$ cells/mL with approx. 42 mL of a mixture of A) 20 mL Opti-MEM medium (Invitrogen) comprising 600 µg total plasmid DNA (1 µg/mL) and B) 20 ml Opti-MEM medium supplemented with 1.2 mL 293 fectin or fectin (2 µl/mL). According to the glucose consumption glucose solution is added during the course of the fermentation. The supernatant containing the secreted antibody is harvested after 5-10 days and antibodies are either directly purified from the supernatant or the supernatant is frozen and stored.

Protein Determination

The protein concentration of purified antibodies and derivatives was determined by determining the optical density (OD) at 280 nm, using the molar extinction coefficient calculated on the basis of the amino acid sequence according to Pace, et al., Protein Science 4 (1995) 2411-1423.

Antibody Concentration Determination in Supernatants

The concentration of antibodies and derivatives in cell culture supernatants was estimated by immunoprecipitation with protein A agarose-beads (Roche Diagnostics GmbH, Mannheim, Germany). Therefore, 60 µL protein A Agarose beads were washed three times in TBS-NP40 (50 mM Tris buffer, pH 7.5, supplemented with 150 mM NaCl and 1% Nonidet-P40). Subsequently, 1-15 mL cell culture supernatant was applied to the protein A Agarose beads pre-equilibrated in TBS-NP40. After incubation for at 1 hour at room temperature the beads were washed on an Ultrafree-MC-filter column (Amicon) once with 0.5 mL TBS-NP40, twice with 0.5 mL 2× phosphate buffered saline (2×PBS, Roche Diagnostics GmbH, Mannheim, Germany) and briefly four times with 0.5 mL 100 mM Na-citrate buffer (pH 5.0). Bound antibody was eluted by addition of 35 µl NuPAGE® LDS sample buffer (Invitrogen). Half of the sample was combined with NuPAGE® sample reducing agent or left unreduced, respectively, and heated for 10 min at 70° C. Consequently, 5-30 µl were applied to a 4-12% NuPAGE® Bis-Tris SDS-PAGE gel (Invitrogen) (with MOPS buffer for non-reduced SDS-PAGE and MES buffer with NuPAGE® antioxidant running buffer additive (Invitrogen) for reduced SDS-PAGE) and stained with Coomassie Blue.

The concentration of the antibodies in cell culture supernatants was quantitatively measured by affinity HPLC chromatography. Briefly, cell culture supernatants containing antibodies that bind to protein A were applied to an Applied Biosystems Poros A/20 column in 200 mM $KH_2PO_4$, 100 mM sodium citrate, pH 7.4 and eluted with 200 mM NaCl, 100 mM citric acid, pH 2.5 on an Agilent HPLC 1100 system. The eluted antibody was quantified by UV absorbance and integration of peak areas. A purified standard IgG1 antibody served as a standard.

Alternatively, the concentration of antibodies and derivatives in cell culture supernatants was measured by Sandwich-IgG-ELISA. Briefly, StreptaWell High Bind Streptavidin A-96 well microtiter plates (Roche Diagnostics GmbH, Mannheim, Germany) were coated with 100 µL/well biotinylated anti-human IgG capture molecule F(ab')2<h-Fcγ> BI (Dianova) at 0.1 µg/mL for 1 hour at room temperature or alternatively overnight at 4° C. and subsequently washed three times with 200 µL/well PBS, 0.05% Tween (PBST, Sigma). Thereafter, 100 µL/well of a dilution series in PBS (Sigma) of the respective antibody containing cell culture supernatants was added to the wells and incubated for 1-2 hour on a shaker at room temperature. The wells were washed three times with 200 µL/well PBST and bound antibody was detected with 100 µl F(ab')2<hFcγ>POD (Dianova) at 0.1 µg/mL as the detection antibody by incubation for 1-2 hours on a shaker at room temperature. Unbound detection antibody was removed by washing three times with 200 µL/well PBST. The bound detection antibody was detected by addition of 100 µL ABTS/well followed by incubation. Determination of absorbance was performed on a Tecan Fluor Spectrometer at a measurement wavelength of 405 nm (reference wavelength 492 nm).

Preparative Antibody Purification

Antibodies were purified from filtered cell culture supernatants referring to standard protocols. In brief, antibodies were applied to a protein A Sepharose column (GE healthcare) and washed with PBS. Elution of antibodies was achieved at pH 2.8 followed by immediate neutralization. Aggregated protein was separated from monomeric antibodies by size exclusion chromatography (Superdex 200, GE Healthcare) in PBS or in 20 mM Histidine buffer comprising 150 mM NaCl (pH 6.0). Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE, size exclusion chromatography (SEC) or mass spectrometry.

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® antioxidant running buffer additive) or MOPS (non-reduced gels) running buffer was used.

CE-SDS

Purity and antibody integrity were analyzed by CE-SDS using microfluidic Labchip technology (PerkinElmer, USA). Therefore, 5 µl of antibody solution was prepared for CE-SDS analysis using the HT Protein Express Reagent Kit according manufacturer's instructions and analyzed on LabChip GXII system using a HT Protein Express Chip. Data were analyzed using LabChip GX Software.

Analytical Size Exclusion Chromatography

Size exclusion chromatography (SEC) for the determination of the aggregation and oligomeric state of antibodies was performed by HPLC chromatography. Briefly, protein A purified antibodies were applied to a Tosoh TSKgel G3000SW column in 300 mM NaCl, 50 mM $KH_2PO_4$/$K_2HPO_4$ buffer (pH 7.5) on an Dionex Ultimate® system (Thermo Fischer Scientific), or to a Superdex 200 column (GE Healthcare) in 2×PBS on a Dionex HPLC-System. The eluted antibody was quantified by UV absorbance and integration of peak areas. BioRad Gel Filtration Standard 151-1901 served as a standard.

Mass Spectrometry

This section describes the characterization of the bispecific antibodies with emphasis on their correct assembly. The expected primary structures were analyzed by electrospray ionization mass spectrometry (ESI-MS) of the deglycosylated intact antibody and in special cases of the deglycosylated/limited LysC digested antibody.

The antibodies were deglycosylated with N-Glycosidase F in a phosphate or Tris buffer at 37° C. for up to 17 h at a protein concentration of 1 mg/ml. The limited LysC (Roche Diagnostics GmbH, Mannheim, Germany) digestions were performed with 100 µg deglycosylated antibody in a Tris buffer (pH 8) at room temperature for 120 hours, or at 37° C. for 40 min, respectively. Prior to mass spectrometry the samples were desalted via HPLC on a Sephadex G25 column (GE Healthcare). The total mass was determined via ESI-MS on a maXis 4G UHR-QTOF MS system (Bruker Daltonik) equipped with a TriVersa NanoMate source (Advion).

Chemical Degradation Test

Samples were split into three aliquots and re-buffered into 20 mM His/His*HCl, 140 mM NaCl, pH 6.0 or into PBS, respectively, and stored at 40° C. (His/NaCl) or 37° C. (PBS). A control sample was stored at −80° C.

After incubation ended, samples were analyzed for relative active concentration (BIAcore), aggregation (SEC) and fragmentation (capillary electrophoresis or SDS-PAGE) and compared with the untreated control.

Thermal Stability

Samples were prepared at a concentration of 1 mg/mL in 20 mM Histidine/Histidine chloride, 140 mM NaCl, pH 6.0, transferred into an optical 384-well plate by centrifugation through a 0.4 m filter plate and covered with paraffin oil. The hydrodynamic radius was measured repeatedly by dynamic light scattering on a DynaPro Plate Reader (Wyatt) while the samples were heated with a rate of 0.05° C./min from 25° C. to 80° C.

Alternatively, samples were transferred into a 10 µL micro-cuvette array and static light scattering data as well as fluorescence data upon excitation with a 266 nm laser were recorded with an Optim1000 instrument (Avacta Inc.), while they were heated at a rate of 0.1° C./min from 25° C. to 90° C.

The aggregation onset temperature is defined as the temperature at which the hydrodynamic radius (DLS) or the scattered light intensity (Optim1000) starts to increase.

Alternatively, samples were transferred in a 9 µL multi-cuvette array. The multi-cuvette array was heated from 35° C. to 90° C. at a constant rate of 0.1° C./minute in an Optim1000 instrument (Avacta Analytical Inc.). The instrument continuously records the intensity of scattered light of a 266 nm laser with a data point approximately every 0.5° C. Light scattering intensities were plotted against the temperature. The aggregation onset temperature (T_agg) is defined as the temperature at which the scattered light intensity begins to increase.

The melting temperature is defined as the inflection point in fluorescence intensity vs. wavelength graph.

Example 1

Expression and Purification

The bispecific antibodies were produced as described above in the general materials and methods section.

The bispecific antibodies were purified from the supernatant by a combination of protein A affinity chromatography and size exclusion chromatography. The obtained products were characterized for identity by mass spectrometry and analytical properties such as purity by CE-SDS, monomer content and stability.

The expected primary structures were analyzed by electrospray ionization mass spectrometry (ESI-MS) of the deglycosylated intact antibody and deglycosylated/plasmin digested or alternatively deglycosylated/limited LysC digested antibody as described in the general methods section.

Additional analytical methods (e.g. thermal stability, mass spectrometry and functional assessment) were only applied after protein A and SEC purification.

Example 2

Determination of Binding to Transferrin Receptor In Vitro

Binding of the bispecific antibodies to murine transferrin receptor is tested by FACS analysis on mouse X63.AG8-563 myeloma cells. If the Aβ antibody shows a certain tendency to non-specifically bind to Ag8 cells, specific binding can be quantified by co-incubation with a 20 fold excess of anti-mouse-TfR antibody. Cells are harvested by centrifugation, washed once with PBS and $5 \times 10^4$ cells incubated with a 1.5 pM to 10 nM dilution series of the polypeptide fusions with or without addition of 200 nM anti-mouse TfR antibody in 100 µL RPMI/10% FCS for 1.5 h on ice. After 2 washes with RPMI/10% FCS, cells are incubated with goat-anti-human IgG coupled to Phycoerythrin (Jackson Immunoresearch) at a dilution of 1:600 in RPMI/19% FCS for 1.5 h on ice. Cells are again washed, resuspended in RPMI/10% FCS and Phycoerythrin fluorescence measured on a FACS-Array instrument (Becton-Dickinson).

Example 3

Surface Plasmon Resonance-Based Binding Assay for Human TfR-Antibody Interaction The binding experiment were carried out on a BIAcore B 4000 (GE Healthcare) equipped with C1 sensor chip (GE Healthcare, cat.no. BR1005-35) pre-treated with anti-human Fab antibody (GE Healthcare, cat.no 28-9583-25) using a standard amine coupling chemistry procedure accordingly to the vendor's manual.

For kinetic measurements the sample antibody was immobilized applying a contact time of 60 seconds and a flow rate of 10 µL/min in phosphate buffer saline pH 7.4, 0.05% Tween 20 at 25° C. Recombinant His6-tagged human transferrin receptor (R&D systems, cat.no 2474-TR-050) was applied in increasing concentrations and the signal monitored over the time. An average time span of 150 seconds of association time and 600 seconds of dissociation time at 30 µL/min flow rate was recorded. Data were fit using a 1:1 binding model (Langmuir isotherm).

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A bispecific antibody comprising
   a) one antibody comprising two pairs each of an antibody light chain and an antibody heavy chain, wherein the binding sites formed by each of the pairs of the heavy chain and the light chain specifically bind to a first antigen, and
   b) one additional Fab fragment, wherein the additional Fab fragment is fused to the C-terminus of one of the heavy chains of the antibody, wherein the binding site of the additional Fab fragment specifically binds to a second antigen,
   wherein the additional Fab fragment specifically binding to the second antigen comprises a domain crossover such that the constant light chain domain (CL) and the constant heavy chain domain 1 (CH1) are replaced by each other,
   wherein the first antigen is human CD20 protein and the second antigen is human transferrin receptor, and
   wherein the bispecific antibody comprises a light chain comprising the amino acid sequence of SEQ ID NO: 1, a heavy chain comprising the amino acid sequence of SEQ ID NO: 2, a Fab fragment comprising a light chain comprising the amino acid sequence of SEQ ID NO: 3, and a heavy chain comprising the amino acid sequence of SEQ ID NO: 4.

2. The antibody of claim 1, wherein the antibody is monoclonal.

3. A pharmaceutical formulation comprising the antibody of claim 1 and a pharmaceutically acceptable carrier.

4. A method of treating an individual having multiple sclerosis comprising administering to the individual an effective amount of the antibody of claim 1.

5. A method of depleting brain sequestered B-cells expressing CD20 in an individual comprising administering to the individual an effective amount of the antibody of claim 1 to deplete brain sequestered B-cells expressing CD20.

* * * * *

SEQUENCE LISTING

<160> NUMBER OF SEQ ID NOS: 22

<210> SEQ ID NO 1
<211> LENGTH: 219
<212> TYPE: PRT
<213> ORGANISM: Artificial Sequence
<220> FEATURE:
<223> OTHER INFORMATION: 0041-LC1

<400> SEQUENCE: 1

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Arg
        115                 120                 125

Lys Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 2
<211> LENGTH: 448
<212> TYPE: PRT
<213> ORGANISM: Artificial Sequence
<220> FEATURE:
<223> OTHER INFORMATION: 0041-HC1

<400> SEQUENCE: 2

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
             85                  90                  95

Ala Arg Asn Val Phe Asp Gly Tyr Trp Leu Val Tyr Trp Gly Gln Gly
         100                 105                 110

Thr Leu Val Thr Val Ser Ser Ala Ser Thr Lys Gly Pro Ser Val Phe
         115                 120                 125

Pro Leu Ala Pro Ser Ser Lys Ser Thr Ser Gly Gly Thr Ala Ala Leu
130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 3
<211> LENGTH: 215
<212> TYPE: PRT
<213> ORGANISM: Artificial Sequence
<220> FEATURE:
<223> OTHER INFORMATION: 0041-LC2

<400> SEQUENCE: 3

```
Ala Ile Gln Leu Thr Gln Ser Pro Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Tyr Ala Ser Ser Asn
            85                  90                  95

Val Asp Asn Thr Phe Gly Gly Gly Thr Lys Val Glu Ile Lys Ser Ser
            100                 105                 110

Ala Ser Thr Lys Gly Pro Ser Val Phe Pro Leu Ala Pro Ser Ser Lys
            115                 120                 125

Ser Thr Ser Gly Gly Thr Ala Ala Leu Gly Cys Leu Val Lys Asp Tyr
        130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
            165                 170                 175

Leu Ser Ser Val Val Thr Val Pro Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys
210                 215

<210> SEQ ID NO 4
<211> LENGTH: 229
<212> TYPE: PRT
<213> ORGANISM: Artificial Sequence
<220> FEATURE:
<223> OTHER INFORMATION: 0041-Fab

<400> SEQUENCE: 4

Gln Ser Met Gln Glu Ser Gly Pro Gly Leu Val Lys Pro Ser Gln Thr
1               5                   10                  15

Leu Ser Leu Thr Cys Thr Val Ser Gly Phe Ser Leu Ser Ser Tyr Ala
            20                  25                  30

Met Ser Trp Ile Arg Gln His Pro Gly Lys Gly Leu Glu Trp Ile Gly
            35                  40                  45

Tyr Ile Trp Ser Gly Gly Ser Thr Asp Tyr Ala Ser Trp Ala Lys Ser
50                  55                  60

Arg Val Thr Ile Ser Lys Thr Ser Thr Val Ser Leu Lys Leu Ser
65                  70                  75                  80

Ser Val Thr Ala Ala Asp Thr Ala Val Tyr Tyr Cys Ala Arg Arg Tyr
            85                  90                  95

Gly Thr Ser Tyr Pro Asp Tyr Gly Asp Ala Ser Gly Phe Asp Pro Trp
            100                 105                 110

Gly Gln Gly Thr Leu Val Thr Val Ser Ser Ala Ser Val Ala Ala Pro
        115                 120                 125

Ser Val Phe Ile Phe Pro Pro Ser Asp Glu Gln Leu Lys Ser Gly Thr
130                 135                 140
```

```
Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
            165                 170                 175

Ser Val Thr Glu Gln Asp Ser Lys Asp Ser Thr Tyr Ser Leu Ser Ser
        180                 185                 190

Thr Leu Thr Leu Ser Lys Ala Asp Tyr Glu Lys His Lys Val Tyr Ala
    195                 200                 205

Cys Glu Val Thr His Gln Gly Leu Ser Ser Pro Val Thr Lys Ser Phe
210                 215                 220

Asn Arg Gly Glu Cys
225

<210> SEQ ID NO 5
<211> LENGTH: 297
<212> TYPE: PRT
<213> ORGANISM: Homo sapiens

<400> SEQUENCE: 5

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285
```

```
Ser Pro Ile Glu Asn Asp Ser Ser Pro
    290                 295
```

<210> SEQ ID NO 6
<211> LENGTH: 219
<212> TYPE: PRT
<213> ORGANISM: Artificial Sequence
<220> FEATURE:
<223> OTHER INFORMATION: 0039-LC1

<400> SEQUENCE: 6

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Arg
        115                 120                 125

Lys Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 7
<211> LENGTH: 448
<212> TYPE: PRT
<213> ORGANISM: Artificial Sequence
<220> FEATURE:
<223> OTHER INFORMATION: 0039-HC1

<400> SEQUENCE: 7

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
```

```
                65                  70                  75                  80
        Met Glu Leu Ser Ser Leu Arg Ser Glu Asp Thr Ala Val Tyr Tyr Cys
                            85                  90                  95

Ala Arg Asn Val Phe Asp Gly Tyr Trp Leu Val Tyr Trp Gly Gln Gly
                        100                 105                 110

Thr Leu Val Thr Val Ser Ser Ala Ser Thr Lys Gly Pro Ser Val Phe
                    115                 120                 125

Pro Leu Ala Pro Ser Ser Lys Ser Thr Ser Gly Gly Thr Ala Ala Leu
                130                 135                 140

Gly Cys Leu Val Glu Asp Tyr Phe Pro Glu Pro Val Thr Val Ser Trp
        145                 150                 155                 160

Asn Ser Gly Ala Leu Thr Ser Gly Val His Thr Phe Pro Ala Val Leu
                        165                 170                 175

Gln Ser Ser Gly Leu Tyr Ser Leu Ser Ser Val Val Thr Val Pro Ser
                    180                 185                 190

Ser Ser Leu Gly Thr Gln Thr Tyr Ile Cys Asn Val Asn His Lys Pro
                195                 200                 205

Ser Asn Thr Lys Val Asp Glu Lys Val Glu Pro Lys Ser Cys Asp Lys
            210                 215                 220

Thr His Thr Cys Pro Pro Cys Pro Ala Pro Glu Ala Ala Gly Gly Pro
        225                 230                 235                 240

Ser Val Phe Leu Phe Pro Pro Lys Pro Lys Asp Thr Leu Met Ile Ser
                        245                 250                 255

Arg Thr Pro Glu Val Thr Cys Val Val Val Asp Val Ser His Glu Asp
                    260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
        305                 310                 315                 320

Tyr Lys Cys Lys Val Ser Asn Lys Ala Leu Gly Ala Pro Ile Glu Lys
                        325                 330                 335

Thr Ile Ser Lys Ala Lys Gly Gln Pro Arg Glu Pro Gln Val Cys Thr
                    340                 345                 350

Leu Pro Pro Ser Arg Asp Glu Leu Thr Lys Asn Gln Val Ser Leu Ser
                355                 360                 365

Cys Ala Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
        385                 390                 395                 400

Asp Ser Asp Gly Ser Phe Phe Leu Val Ser Lys Leu Thr Val Asp Lys
                        405                 410                 415

Ser Arg Trp Gln Gln Gly Asn Val Phe Ser Cys Ser Val Met His Glu
                    420                 425                 430

Ala Leu His Asn His Tyr Thr Gln Lys Ser Leu Ser Leu Ser Pro Gly
                435                 440                 445

<210> SEQ ID NO 8
<211> LENGTH: 229
<212> TYPE: PRT
<213> ORGANISM: Artificial Sequence
<220> FEATURE:
<223> OTHER INFORMATION: 0039-LC2
```

```
<400> SEQUENCE: 8

Gln Ser Met Gln Glu Ser Gly Pro Gly Leu Val Lys Pro Ser Gln Thr
1               5                   10                  15

Leu Ser Leu Thr Cys Thr Val Ser Gly Phe Ser Leu Ser Ser Tyr Ala
            20                  25                  30

Met Ser Trp Ile Arg Gln His Pro Gly Lys Gly Leu Glu Trp Ile Gly
        35                  40                  45

Tyr Ile Trp Ser Gly Gly Ser Thr Asp Tyr Ala Ser Trp Ala Lys Ser
    50                  55                  60

Arg Val Thr Ile Ser Lys Thr Ser Thr Thr Val Ser Leu Lys Leu Ser
65                  70                  75                  80

Ser Val Thr Ala Ala Asp Thr Ala Val Tyr Tyr Cys Ala Arg Arg Tyr
                85                  90                  95

Gly Thr Ser Tyr Pro Asp Tyr Gly Asp Ala Ser Gly Phe Asp Pro Trp
            100                 105                 110

Gly Gln Gly Thr Leu Val Thr Val Ser Ser Ala Ser Val Ala Ala Pro
        115                 120                 125

Ser Val Phe Ile Phe Pro Pro Ser Asp Glu Gln Leu Lys Ser Gly Thr
    130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
    210                 215                 220

Asn Arg Gly Glu Cys
225

<210> SEQ ID NO 9
<211> LENGTH: 681
<212> TYPE: PRT
<213> ORGANISM: Artificial Sequence
<220> FEATURE:
<223> OTHER INFORMATION: 0039-HC2

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
```

```
                  115                 120                 125
Pro Leu Ala Pro Ser Ser Lys Ser Thr Ser Gly Gly Thr Ala Ala Leu
130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Cys Arg Asp Glu Leu Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Gly Gly Ser Gly Gly Gly Ser Gly Gly Gly Ser Gly Gly Gly
    450                 455                 460

Gly Ser Ala Ile Gln Leu Thr Gln Ser Pro Ser Ser Leu Ser Ala Ser
465                 470                 475                 480

Val Gly Asp Arg Val Thr Ile Thr Cys Arg Ala Ser Gln Ser Ile Ser
                485                 490                 495

Ser Tyr Leu Ala Trp Tyr Gln Gln Lys Pro Gly Lys Ala Pro Lys Leu
            500                 505                 510

Leu Ile Tyr Arg Ala Ser Thr Leu Ala Ser Gly Val Pro Ser Arg Phe
        515                 520                 525

Ser Gly Ser Gly Ser Gly Thr Asp Phe Thr Leu Thr Ile Ser Ser Leu
    530                 535                 540
```

Gln Pro Glu Asp Phe Ala Thr Tyr Tyr Cys Gln Gln Asn Tyr Ala Ser
545                 550                 555                 560

Ser Asn Val Asp Asn Thr Phe Gly Gly Gly Thr Lys Val Glu Ile Lys
            565                 570                 575

Ser Ser Ala Ser Thr Lys Gly Pro Ser Val Phe Pro Leu Ala Pro Ser
        580                 585                 590

Ser Lys Ser Thr Ser Gly Gly Thr Ala Ala Leu Gly Cys Leu Val Lys
        595                 600                 605

Asp Tyr Phe Pro Glu Pro Val Thr Val Ser Trp Asn Ser Gly Ala Leu
        610                 615                 620

Thr Ser Gly Val His Thr Phe Pro Ala Val Leu Gln Ser Ser Gly Leu
625                 630                 635                 640

Tyr Ser Leu Ser Ser Val Val Thr Val Pro Ser Ser Ser Leu Gly Thr
            645                 650                 655

Gln Thr Tyr Ile Cys Asn Val Asn His Lys Pro Ser Asn Thr Lys Val
            660                 665                 670

Asp Lys Lys Val Glu Pro Lys Ser Cys
        675                 680

<210> SEQ ID NO 10
<211> LENGTH: 695
<212> TYPE: PRT
<213> ORGANISM: Artificial Sequence
<220> FEATURE:
<223> OTHER INFORMATION: 0041-HC2

<400> SEQUENCE: 10

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

```
Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Cys Arg Asp Glu Leu Thr Lys Asn Gln Val Ser Leu Trp
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Gly Gly Ser Gly Gly Gly Ser Gly Gly Gly Ser Gly Gly Gly
    450                 455                 460

Gly Ser Gln Ser Met Gln Glu Ser Gly Pro Gly Leu Val Lys Pro Ser
465                 470                 475                 480

Gln Thr Leu Ser Leu Thr Cys Thr Val Ser Gly Phe Ser Leu Ser Ser
                485                 490                 495

Tyr Ala Met Ser Trp Ile Arg Gln His Pro Gly Lys Gly Leu Glu Trp
            500                 505                 510

Ile Gly Tyr Ile Trp Ser Gly Gly Ser Thr Asp Tyr Ala Ser Trp Ala
        515                 520                 525

Lys Ser Arg Val Thr Ile Ser Lys Thr Ser Thr Thr Val Ser Leu Lys
530                 535                 540

Leu Ser Ser Val Thr Ala Ala Asp Thr Ala Val Tyr Tyr Cys Ala Arg
545                 550                 555                 560

Arg Tyr Gly Thr Ser Tyr Pro Asp Tyr Gly Asp Ala Ser Gly Phe Asp
                565                 570                 575

Pro Trp Gly Gln Gly Thr Leu Val Thr Val Ser Ser Ala Ser Val Ala
            580                 585                 590

Ala Pro Ser Val Phe Ile Phe Pro Pro Ser Asp Glu Gln Leu Lys Ser
        595                 600                 605

Gly Thr Ala Ser Val Val Cys Leu Leu Asn Asn Phe Tyr Pro Arg Glu
610                 615                 620

Ala Lys Val Gln Trp Lys Val Asp Asn Ala Leu Gln Ser Gly Asn Ser
625                 630                 635                 640
```

Gln Glu Ser Val Thr Glu Gln Asp Ser Lys Asp Ser Thr Tyr Ser Leu
                     645                 650                 655

Ser Ser Thr Leu Thr Leu Ser Lys Ala Asp Tyr Glu Lys His Lys Val
             660                 665                 670

Tyr Ala Cys Glu Val Thr His Gln Gly Leu Ser Ser Pro Val Thr Lys
         675                 680                 685

Ser Phe Asn Arg Gly Glu Cys
    690                 695

<210> SEQ ID NO 11
<211> LENGTH: 219
<212> TYPE: PRT
<213> ORGANISM: Artificial Sequence
<220> FEATURE:
<223> OTHER INFORMATION: 0040-LC1

<400> SEQUENCE: 11

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 12
<211> LENGTH: 448
<212> TYPE: PRT
<213> ORGANISM: Artificial Sequence
<220> FEATURE:
<223> OTHER INFORMATION: 0040-HC1

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

```
<210> SEQ ID NO 13
<211> LENGTH: 695
<212> TYPE: PRT
<213> ORGANISM: Artificial Sequence
<220> FEATURE:
<223> OTHER INFORMATION: 0040-HC2

<400> SEQUENCE: 13
```

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Lys | Lys | Pro | Gly |
| 1 | | | | 5 | | | | | 10 | | | | | 15 |
| Ser | | | | | | | | | | | | | | |

Ser Val Lys Val Ser Cys Lys Ala Ser Gly Tyr Ala Phe Ser Tyr Ser
                20                  25                  30

Trp Ile Asn Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Cys Arg Asp Glu Leu Thr Lys Asn Gln Val Ser Leu Trp
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Gly Gly Ser Gly Gly Gly Ser Gly Gly Gly Ser Gly Gly Gly
450                 455                 460

Gly Ser Gln Ser Met Gln Glu Ser Gly Pro Gly Leu Val Lys Pro Ser
465                 470                 475                 480

Gln Thr Leu Ser Leu Thr Cys Thr Val Ser Gly Phe Ser Leu Ser Ser
                485                 490                 495

Tyr Ala Met Ser Trp Ile Arg Gln His Pro Gly Lys Gly Leu Glu Trp
            500                 505                 510

Ile Gly Tyr Ile Trp Ser Gly Gly Ser Thr Asp Tyr Ala Ser Trp Ala
        515                 520                 525

Lys Ser Arg Val Thr Ile Ser Lys Thr Ser Thr Thr Val Ser Leu Lys
530                 535                 540

Leu Ser Ser Val Thr Ala Ala Asp Thr Ala Val Tyr Tyr Cys Ala Arg
545                 550                 555                 560

Arg Tyr Gly Thr Ser Tyr Pro Asp Tyr Gly Asp Ala Ser Gly Phe Asp
                565                 570                 575

Pro Trp Gly Gln Gly Thr Leu Val Thr Val Ser Ser Ala Ser Val Ala
            580                 585                 590

Ala Pro Ser Val Phe Ile Phe Pro Pro Ser Asp Glu Gln Leu Lys Ser
        595                 600                 605

Gly Thr Ala Ser Val Val Cys Leu Leu Asn Asn Phe Tyr Pro Arg Glu
610                 615                 620

Ala Lys Val Gln Trp Lys Val Asp Asn Ala Leu Gln Ser Gly Asn Ser
625                 630                 635                 640

Gln Glu Ser Val Thr Glu Gln Asp Ser Lys Asp Ser Thr Tyr Ser Leu
                645                 650                 655

Ser Ser Thr Leu Thr Leu Ser Lys Ala Asp Tyr Glu Lys His Lys Val
            660                 665                 670

Tyr Ala Cys Glu Val Thr His Gln Gly Leu Ser Ser Pro Val Thr Lys
        675                 680                 685

Ser Phe Asn Arg Gly Glu Cys
690                 695

<210> SEQ ID NO 14
<211> LENGTH: 219
<212> TYPE: PRT
<213> ORGANISM: Artificial Sequence
<220> FEATURE:
<223> OTHER INFORMATION: 0042-LC1

<400> SEQUENCE: 14

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Val Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Arg
        115                 120                 125

Lys Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 15
<211> LENGTH: 448
<212> TYPE: PRT
<213> ORGANISM: Artificial Sequence
<220> FEATURE:
<223> OTHER INFORMATION: 0042-HC1

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Glu Lys Val Glu Pro Lys Ser Cys Asp Lys
        210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 16
<211> LENGTH: 229
<212> TYPE: PRT
<213> ORGANISM: Artificial Sequence
<220> FEATURE:
<223> OTHER INFORMATION: 0042-LC2

<400> SEQUENCE: 16

Gln Ser Met Gln Glu Ser Gly Pro Gly Leu Val Lys Pro Ser Gln Thr
1               5                   10                  15

Leu Ser Leu Thr Cys Thr Val Ser Gly Phe Ser Leu Ser Ser Tyr Ala
            20                  25                  30

Met Ser Trp Ile Arg Gln His Pro Gly Lys Gly Leu Glu Trp Ile Gly
        35                  40                  45

Tyr Ile Trp Ser Gly Gly Ser Thr Asp Tyr Ala Ser Trp Ala Lys Ser
    50                  55                  60

Arg Val Thr Ile Ser Lys Thr Ser Thr Thr Val Ser Leu Lys Leu Ser
65                  70                  75                  80

Ser Val Thr Ala Ala Asp Thr Ala Val Tyr Tyr Cys Ala Arg Arg Tyr
                85                  90                  95

-continued

Gly Thr Ser Tyr Pro Asp Tyr Gly Asp Ala Ser Gly Phe Asp Pro Trp
                100                 105                 110

Gly Gln Gly Thr Leu Val Thr Val Ser Ser Ala Ser Val Ala Ala Pro
            115                 120                 125

Ser Val Phe Ile Phe Pro Pro Ser Asp Glu Gln Leu Lys Ser Gly Thr
        130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
210                 215                 220

Asn Arg Gly Glu Cys
225

<210> SEQ ID NO 17
<211> LENGTH: 674
<212> TYPE: PRT
<213> ORGANISM: Artificial Sequence
<220> FEATURE:
<223> OTHER INFORMATION: 0042-HC2

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Gly
210                 215                 220

```
Gly Gly Gly Ser Gly Gly Gly Ser Ala Ile Gln Leu Thr Gln Ser
225                 230                 235                 240

Pro Ser Ser Leu Ser Ala Ser Val Gly Asp Arg Val Thr Ile Thr Cys
            245                 250                 255

Arg Ala Ser Gln Ser Ile Ser Ser Tyr Leu Ala Trp Tyr Gln Lys
            260                 265                 270

Pro Gly Lys Ala Pro Lys Leu Leu Ile Tyr Arg Ala Ser Thr Leu Ala
            275                 280                 285

Ser Gly Val Pro Ser Arg Phe Ser Gly Ser Gly Ser Gly Thr Asp Phe
290                 295                 300

Thr Leu Thr Ile Ser Ser Leu Gln Pro Glu Asp Phe Ala Thr Tyr Tyr
305                 310                 315                 320

Cys Gln Gln Asn Tyr Ala Ser Ser Asn Val Asp Asn Thr Phe Gly Gly
            325                 330                 335

Gly Thr Lys Val Glu Ile Lys Ser Ser Ala Ser Thr Lys Gly Pro Ser
            340                 345                 350

Val Phe Pro Leu Ala Pro Ser Ser Lys Ser Thr Ser Gly Gly Thr Ala
            355                 360                 365

Ala Leu Gly Cys Leu Val Lys Asp Tyr Phe Pro Glu Pro Val Thr Val
            370                 375                 380

Ser Trp Asn Ser Gly Ala Leu Thr Ser Gly Val His Thr Phe Pro Ala
385                 390                 395                 400

Val Leu Gln Ser Ser Gly Leu Tyr Ser Leu Ser Ser Val Val Thr Val
                405                 410                 415

Pro Ser Ser Ser Leu Gly Thr Gln Thr Tyr Ile Cys Asn Val Asn His
            420                 425                 430

Lys Pro Ser Asn Thr Lys Val Asp Lys Lys Val Glu Pro Lys Ser Cys
            435                 440                 445

Asp Lys Thr His Thr Cys Pro Pro Cys Pro Ala Pro Glu Ala Ala Gly
            450                 455                 460

Gly Pro Ser Val Phe Leu Phe Pro Pro Lys Pro Lys Asp Thr Leu Met
465                 470                 475                 480

Ile Ser Arg Thr Pro Glu Val Thr Cys Val Val Val Asp Val Ser His
                485                 490                 495

Glu Asp Pro Glu Val Lys Phe Asn Trp Tyr Val Asp Gly Val Glu Val
            500                 505                 510

His Asn Ala Lys Thr Lys Pro Arg Glu Glu Gln Tyr Asn Ser Thr Tyr
            515                 520                 525

Arg Val Val Ser Val Leu Thr Val Leu His Gln Asp Trp Leu Asn Gly
530                 535                 540

Lys Glu Tyr Lys Cys Lys Val Ser Asn Lys Ala Leu Gly Ala Pro Ile
545                 550                 555                 560

Glu Lys Thr Ile Ser Lys Ala Lys Gly Gln Pro Arg Glu Pro Gln Val
                565                 570                 575

Tyr Thr Leu Pro Pro Cys Arg Asp Glu Leu Thr Lys Asn Gln Val Ser
            580                 585                 590

Leu Trp Cys Leu Val Lys Gly Phe Tyr Pro Ser Asp Ile Ala Val Glu
            595                 600                 605

Trp Glu Ser Asn Gly Gln Pro Glu Asn Asn Tyr Lys Thr Thr Pro Pro
            610                 615                 620

Val Leu Asp Ser Asp Gly Ser Phe Phe Leu Tyr Ser Lys Leu Thr Val
625                 630                 635                 640

Asp Lys Ser Arg Trp Gln Gln Gly Asn Val Phe Ser Cys Ser Val Met
```

His Glu Ala Leu His Asn His Tyr Thr Gln Lys Ser Leu Ser Leu Ser
                645                 650                 655
Pro Gly
    660

<210> SEQ ID NO 18
<211> LENGTH: 119
<212> TYPE: PRT
<213> ORGANISM: Artificial Sequence
<220> FEATURE:
<223> OTHER INFORMATION: anti-CD20 antibody VH

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 19
<211> LENGTH: 112
<212> TYPE: PRT
<213> ORGANISM: Artificial Sequence
<220> FEATURE:
<223> OTHER INFORMATION: anti-CD20 antibody VL

<400> SEQUENCE: 19

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

<210> SEQ ID NO 20
<211> LENGTH: 122
<212> TYPE: PRT
<213> ORGANISM: Artificial Sequence
<220> FEATURE:
<223> OTHER INFORMATION: 299-023 VH humanization variant_DASG

<400> SEQUENCE: 20

```
Gln Ser Met Gln Glu Ser Gly Pro Gly Leu Val Lys Pro Ser Gln Thr
1               5                   10                  15

Leu Ser Leu Thr Cys Thr Val Ser Gly Phe Ser Leu Ser Ser Tyr Ala
            20                  25                  30

Met Ser Trp Ile Arg Gln His Pro Gly Lys Gly Leu Glu Trp Ile Gly
        35                  40                  45

Tyr Ile Trp Ser Gly Gly Ser Thr Asp Tyr Ala Ser Trp Ala Lys Ser
    50                  55                  60

Arg Val Thr Ile Ser Lys Thr Ser Thr Val Ser Leu Lys Leu Ser
65                  70                  75                  80

Ser Val Thr Ala Ala Asp Thr Ala Val Tyr Tyr Cys Ala Arg Arg Tyr
                85                  90                  95

Gly Thr Ser Tyr Pro Asp Tyr Gly Asp Ala Ser Gly Phe Asp Pro Trp
                100                 105                 110

Gly Gln Gly Thr Leu Val Thr Val Ser Ser
            115                 120
```

<210> SEQ ID NO 21
<211> LENGTH: 110
<212> TYPE: PRT
<213> ORGANISM: Artificial Sequence
<220> FEATURE:
<223> OTHER INFORMATION: 299-009 VL humanization variant_NYA

<400> SEQUENCE: 21

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Tyr Ala Ser Ser Asn
                85                  90                  95

Val Asp Asn Thr Phe Gly Gly Gly Thr Lys Val Glu Ile Lys
                100                 105                 110
```

<210> SEQ ID NO 22
<211> LENGTH: 215
<212> TYPE: PRT
<213> ORGANISM: Artificial Sequence
<220> FEATURE:
<223> OTHER INFORMATION: 0040-LC2

<400> SEQUENCE: 22

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asn Tyr Ala Ser Ser Asn
                 85                  90                  95

Val Asp Asn Thr Phe Gly Gly Gly Thr Lys Val Glu Ile Lys Ser Ser
             100                 105                 110

Ala Ser Thr Lys Gly Pro Ser Val Phe Pro Leu Ala Pro Ser Ser Lys
         115                 120                 125

Ser Thr Ser Gly Gly Thr Ala Ala Leu Gly Cys Leu Val Lys Asp Tyr
     130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                 165                 170                 175

Leu Ser Ser Val Val Thr Val Pro Ser Ser Ser Leu Gly Thr Gln Thr
             180                 185                 190

Tyr Ile Cys Asn Val Asn His Lys Pro Ser Asn Thr Lys Val Asp Lys
         195                 200                 205

Lys Val Glu Pro Lys Ser Cys
210                 215
```